US009492495B2

(12) United States Patent
Hillmeister et al.

(10) Patent No.: US 9,492,495 B2
(45) Date of Patent: Nov. 15, 2016

(54) THERAPEUTIC USE OF AGONISTS OR ANTAGONISTS OF BRADYKININ RECEPTOR 1 OR 2, FOR MODULATION COLLATERAL BLOOD VESSEL GROWTH

(75) Inventors: Philipp Hillmeister, Berlin (DE); Ivo Buschmann, Berlin (DE); Ferdinand Lenoble, Berlin (DE); Nora Gatzke, Luebben (DE)

(73) Assignee: MAX-DELBRUECK-CENTRUM FUER MOLEKULARE MEDIZIN, Berlin (DE)

( * ) Notice: Subject to any disclaimer, the term of this patent is extended or adjusted under 35 U.S.C. 154(b) by 169 days.

(21) Appl. No.: 13/697,745

(22) PCT Filed: May 16, 2011

(86) PCT No.: PCT/EP2011/002521
§ 371 (c)(1),
(2), (4) Date: Feb. 5, 2013

(87) PCT Pub. No.: WO2011/141188
PCT Pub. Date: Nov. 17, 2011

(65) Prior Publication Data
US 2013/0136717 A1 May 30, 2013

(30) Foreign Application Priority Data

May 14, 2010 (EP) .................................. 10075199
Aug. 18, 2010 (EP) .................................. 10075353

(51) Int. Cl.
| | |
|---|---|
| *A61K 38/22* | (2006.01) |
| *A61K 38/04* | (2006.01) |
| *A61K 45/06* | (2006.01) |
| *C07K 7/18* | (2006.01) |
| *A61K 31/401* | (2006.01) |
| *A61K 31/403* | (2006.01) |
| *A61K 31/404* | (2006.01) |
| *A61K 31/472* | (2006.01) |
| *A61K 31/675* | (2006.01) |

(52) U.S. Cl.
CPC ............. *A61K 38/043* (2013.01); *A61K 38/04* (2013.01); *A61K 45/06* (2013.01); *C07K 7/18* (2013.01); *A61K 31/401* (2013.01); *A61K 31/403* (2013.01); *A61K 31/404* (2013.01); *A61K 31/472* (2013.01); *A61K 31/675* (2013.01)

(58) Field of Classification Search
None
See application file for complete search history.

(56) References Cited

U.S. PATENT DOCUMENTS 6,015,818 A  1/2000  Oku et al.

FOREIGN PATENT DOCUMENTS

| CA | 2122429 A1 | 10/1994 |
|---|---|---|
| DE | 101 15 668 A1 | 10/2002 |
| EP | 0 623 350 A1 | 11/1994 |
| WO | 98/06417 A1 | 2/1998 |
| WO | 02/17958 A1 | 3/2002 |
| WO | 2004/069857 A2 | 8/2004 |
| WO | 2006/071775 A2 | 7/2006 |

OTHER PUBLICATIONS

Stone O.A. et al.: "Critical role of tissue kallikrein in vessel formation and maturation : implications for therapeutic revascularization.", in: Arterioscler. Thromb. Vasc. Biol., vol. 29, 2009, pp. 657-664.
Smith Robert S Jr et al: "Tissue kallikrein and kinin infusion promotes neovascularization in limb ischemia", Biological Chemistry, Walter De Gruyter GMBH & Co, Berlin, DE, vol. 389, No. 6, Jun. 1, 2008, pp. 725-730.
Chahine R et al: "Protective Effects of Bradykinin on the Ischaemic Heart: Implication of the B1 Receptor", in: British Journal of Pharmacology, Nature Publishing Group, Basingstoke, Hants; GB, vol. 108, No. 2, Jan. 1, 1993, pp. 318-322.
Emanueli et al., "Targeting Kinin B1 Receptor for Therapeutic Neovascularization," in Circulation, vol. 105, 2002, pp. 360-366.
Stone et al: "Mechanisms of hKLKI Induced Arteriogenesis", in: Arteriosclerosis, Thrombosis and Vascular Biology, XP-002620098.
Taraseviciene-Stewart, Laimute et al. "Treatment of severe pulmonary hypertension: A bradykinin receptor 2 agonist B9972 causes reduction of pulmonary artery pressure and right ventricular hypertrophy" in: Peptides, Aug. 1, 2005, vol. 26, No. 8, pp. 1292-1300.
Heitsch, Holger: "The therapeutic potential of bradykinin B2 receptor agonists in the treatment of cardiovascular disease" in: Expert Opin.Investig. Drugs, May 1, 2003, vol. 12, No. 5, pp. 759-770.
Frew, E.M. et al.: "Inhibition of the bradykinin B2 receptor protects against ischemic brain damage in normotensive and hypertensive rats", in: Society for Neuroscience Abstracts, 2000, vol. 26, Abstract No. -670. 7.
Nowak, K.: "Bradykinin in ischemia-reperfusion injury of the rat lung", in: Journal of Physiology and Pharmacology, 2007-11, vol. 58, pp. 513-522.

*Primary Examiner* — Michael Pak
(74) *Attorney, Agent, or Firm* — Joyce von Natzmer; Agris & von Natzmer LLP

(57) ABSTRACT

The present invention relates to bradykinin receptor modulators and pharmaceutical compositions thereof for use as a medicament for modulating collateral blood vessel growth of collateral arteries and/or other blood vessels of preexisting arterial networks. The bradykinin receptor modulators of arteriogenesis are applicable in the treatment and/or prevention of disorders associated with defective blood flow or blood vessel malformation. A preferred aspect of the invention relates to bradykinin receptor agonists for use as a medicament for the prevention of cardiovascular ischemic disease in a patient at risk thereof. Further, the invention relates to a bradykinin receptor agonist for use in a method for treating a cardiovascular ischemic disease in a patient in need thereof, wherein said cardiovascular ischemic disease is a peripheral limb disease.

16 Claims, 8 Drawing Sheets

SEQUENCE LISTING

<160> NUMBER OF SEQ ID NOS: 12

<210> SEQ ID NO 1
<211> LENGTH: 353
<212> TYPE: PRT
<213> ORGANISM: Homo sapiens

<400> SEQUENCE: 1

```
Met Ala Ser Ser Trp Pro Pro Leu Glu Leu Gln Ser Ser Asn Gln Ser
1               5                   10                  15

Gln Leu Phe Pro Gln Asn Ala Thr Ala Cys Asp Asn Ala Pro Glu Ala
            20                  25                  30

Trp Asp Leu Leu His Arg Val Leu Pro Thr Phe Ile Ile Ser Ile Cys
        35                  40                  45

Phe Phe Gly Leu Leu Gly Asn Leu Phe Val Leu Val Phe Leu Leu
    50                  55                  60

Pro Arg Arg Gln Leu Asn Val Ala Glu Ile Tyr Leu Ala Asn Leu Ala
65                  70                  75                  80

Ala Ser Asp Leu Val Phe Val Leu Gly Leu Pro Phe Trp Ala Glu Asn
                85                  90                  95

Ile Trp Asn Gln Phe Asn Trp Pro Phe Gly Ala Leu Leu Cys Arg Val
            100                 105                 110

Ile Asn Gly Val Ile Lys Ala Asn Leu Phe Ile Ser Ile Phe Leu Val
            115                 120                 125

Val Ala Ile Ser Gln Asp Arg Tyr Arg Val Leu Val His Pro Met Ala
        130                 135                 140

Ser Arg Arg Gln Gln Arg Arg Arg Gln Ala Arg Val Thr Cys Val Leu
145                 150                 155                 160

Ile Trp Val Val Gly Gly Leu Leu Ser Ile Pro Thr Phe Leu Leu Arg
                165                 170                 175

Ser Ile Gln Ala Val Pro Asp Leu Asn Ile Thr Ala Cys Ile Leu Leu
            180                 185                 190

Leu Pro His Glu Ala Trp His Phe Ala Arg Ile Val Glu Leu Asn Ile
        195                 200                 205

Leu Gly Phe Leu Leu Pro Leu Ala Ala Ile Val Phe Phe Asn Tyr His
    210                 215                 220

Ile Leu Ala Ser Leu Arg Thr Arg Glu Glu Val Ser Arg Thr Arg Cys
225                 230                 235                 240

Gly Gly Arg Lys Asp Ser Lys Thr Thr Ala Leu Ile Leu Thr Leu Val
                245                 250                 255

Val Ala Phe Leu Val Cys Trp Ala Pro Tyr His Phe Phe Ala Phe Leu
            260                 265                 270

Glu Phe Leu Phe Gln Val Gln Ala Val Arg Gly Cys Phe Trp Glu Asp
        275                 280                 285

Phe Ile Asp Leu Gly Leu Gln Leu Ala Asn Phe Phe Ala Phe Thr Asn
    290                 295                 300

Ser Ser Leu Asn Pro Val Ile Tyr Val Phe Val Gly Arg Leu Phe Arg
305                 310                 315                 320

Thr Lys Val Trp Glu Leu Tyr Lys Gln Cys Thr Pro Lys Ser Leu Ala
                325                 330                 335

Pro Ile Ser Ser Ser His Arg Lys Glu Ile Phe Gln Leu Phe Trp Arg
            340                 345                 350

Asn
```

```
<210> SEQ ID NO 2
<211> LENGTH: 364
<212> TYPE: PRT
<213> ORGANISM: Homo sapiens

<400> SEQUENCE: 2

Met Leu Asn Val Thr Leu Gln Gly Pro Thr Leu Asn Gly Thr Phe Ala
1               5                   10                  15

Gln Ser Lys Cys Pro Gln Val Glu Trp Leu Gly Trp Leu Asn Thr Ile
            20                  25                  30

Gln Pro Pro Phe Leu Trp Val Leu Phe Val Leu Ala Thr Leu Glu Asn
        35                  40                  45

Ile Phe Val Leu Ser Val Phe Cys Leu His Lys Ser Ser Cys Thr Val
50                  55                  60

Ala Glu Ile Tyr Leu Gly Asn Leu Ala Ala Ala Asp Leu Ile Leu Ala
65                  70                  75                  80

Cys Gly Leu Pro Phe Trp Ala Ile Thr Ile Ser Asn Asn Phe Asp Trp
                85                  90                  95

Leu Phe Gly Glu Thr Leu Cys Arg Val Val Asn Ala Ile Ile Ser Met
            100                 105                 110

Asn Leu Tyr Ser Ser Ile Cys Phe Leu Met Leu Val Ser Ile Asp Arg
        115                 120                 125

Tyr Leu Ala Leu Val Lys Thr Met Ser Met Gly Arg Met Arg Gly Val
130                 135                 140

Arg Trp Ala Lys Leu Tyr Ser Leu Val Ile Trp Gly Cys Thr Leu Leu
145                 150                 155                 160

Leu Ser Ser Pro Met Leu Val Phe Arg Thr Met Lys Glu Tyr Ser Asp
                165                 170                 175

Glu Gly His Asn Val Thr Ala Cys Val Ile Ser Tyr Pro Ser Leu Ile
            180                 185                 190

Trp Glu Val Phe Thr Asn Met Leu Leu Asn Val Val Gly Phe Leu Leu
        195                 200                 205

Pro Leu Ser Val Ile Thr Phe Cys Thr Met Gln Ile Met Gln Val Leu
210                 215                 220

Arg Asn Asn Glu Met Gln Lys Phe Lys Glu Ile Gln Thr Glu Arg Arg
225                 230                 235                 240

Ala Thr Val Leu Val Leu Val Val Leu Leu Leu Phe Ile Ile Cys Trp
                245                 250                 255

Leu Pro Phe Gln Ile Ser Thr Phe Leu Asp Thr Leu His Arg Leu Gly
            260                 265                 270

Ile Leu Ser Ser Cys Gln Asp Glu Arg Ile Ile Asp Val Ile Thr Gln
        275                 280                 285

Ile Ala Ser Phe Met Ala Tyr Ser Asn Ser Cys Leu Asn Pro Leu Val
290                 295                 300

Tyr Val Ile Val Gly Lys Arg Phe Arg Lys Lys Ser Trp Glu Val Tyr
305                 310                 315                 320

Gln Gly Val Cys Gln Lys Gly Gly Cys Arg Ser Glu Pro Ile Gln Met
                325                 330                 335

Glu Asn Ser Met Gly Thr Leu Arg Thr Ser Ile Ser Val Glu Arg Gln
            340                 345                 350

Ile His Lys Leu Gln Asp Trp Ala Gly Ser Arg Gln
        355                 360

<210> SEQ ID NO 3
<211> LENGTH: 9
```

```
<212> TYPE: PRT
<213> ORGANISM: Homo sapiens

<400> SEQUENCE: 3

Arg Pro Pro Gly Phe Ser Pro Phe Arg
1               5

<210> SEQ ID NO 4
<211> LENGTH: 10
<212> TYPE: PRT
<213> ORGANISM: Homo sapiens

<400> SEQUENCE: 4

Lys Arg Pro Pro Gly Phe Ser Pro Phe Arg
1               5                   10

<210> SEQ ID NO 5
<211> LENGTH: 11
<212> TYPE: PRT
<213> ORGANISM: Homo sapiens

<400> SEQUENCE: 5

Met Lys Arg Pro Pro Gly Phe Ser Pro Phe Arg
1               5                   10

<210> SEQ ID NO 6
<211> LENGTH: 11
<212> TYPE: PRT
<213> ORGANISM: Homo sapiens

<400> SEQUENCE: 6

Ile Ser Arg Pro Pro Gly Phe Ser Pro Phe Arg
1               5                   10

<210> SEQ ID NO 7
<211> LENGTH: 8
<212> TYPE: PRT
<213> ORGANISM: Homo sapiens

<400> SEQUENCE: 7

Arg Pro Pro Gly Phe Ser Pro Phe
1               5

<210> SEQ ID NO 8
<211> LENGTH: 9
<212> TYPE: PRT
<213> ORGANISM: Homo sapiens

<400> SEQUENCE: 8

Lys Arg Pro Pro Gly Phe Ser Pro Phe
1               5

<210> SEQ ID NO 9
<211> LENGTH: 27879
<212> TYPE: DNA
<213> ORGANISM: Homo sapiens

<400> SEQUENCE: 9
tttgcttttg cagcctttttt aatgtctttc agttcaaagt actcggcatg ccaagagcc      60 atatttgggg ctatcttttt ctgtgccaaa ccaacaacac caaaccagaa agaagcaagc     120
atagggaatc cagggcttca ctcaacccat cccttcctat gcttttcctc tatctccacc     180
ctgggagcaa ttttctttta cagaactaat gcaactgagc agagaaaggc tggcctgtcc     240
```

```
agagagcaga taggacgccc atatttatt ttcagttgtg ccaatgtcct gcatgggact    300
cctggaactc actggatgcc cctgtgcatg agcttcttag gcatgtaata gaattaacag    360
cagtctgctt ctatgcaggt aggtatcctg caaagaaact ttgtatgaaa tgtgtctgca    420
cattgtactc attcttgcat tgtttaccca tgtagtgacc ttcaaaaatg ctttgcaaa     480 agtcacaggg gaataaccga gttagtaggc acttgtttcc cctccttcat cagattctgc    540
tctgatttgc tacataaagt tgtataatca cctggaaata tgcactgtgc tgccacgtga    600
ttttcaaatg caaatgagca ggttaacaac cccagtgttg caatgttcta gctgtaaata    660
tgtttggata acccagcaga gccatttaac ctttgggaac aaggcaacta gcgtctggca    720
gcaggaatcc aaccagtgcc ctgagttctg aggcagagag gaggacagaa gaaacaagag    780
gctggagatt gtcaaattca gtatcccagt tggctcttga ttcttggtga aaccatccct    840
cagctcctag agggagattg ttagatcatg aaactaatta ccatccttt cctctgctcc     900 aggctgctac taagttaac ccaggaatca cagtccgagg aaattgactg caatgacaag     960
gatttattta aagctgtgga tgctgctctg aagaaatata acagtcaaaa ccaaagtaac    1020 aaccagttg tattgtaccg cataactgaa gccactaaga cggtgagtga attgtgttta     1080
accttgaagt cacttgggat ttgtactatc actaggagtc caggcctcac acacacacac    1140
acataccacc accagcaccc accaccacca cccaccaccc accaccatca cccaccacca    1200
ccaccacaac caccaccacc acccaccacc accaccacca tccaccacca cccaccaccc    1260
accaccaccc accaccatca cccaccaccc accaccacc accccacc atcatcaccc       1320 accaccaccc accaccatca cccaccaccc accaccactc gccaccatca cccaccacca    1380
tcacccacca cccaccaccc accaccacca accaccacca tccaccacca ccaaccacca    1440
cccaccacca ctaccacccc tcaccaccca ccaccaccgc cacccaccac ccaccaccat    1500
cacccaccac caccaccatc caccaccacc acccaaccac caccccac cacccaccac     1560 catcacccac cacccaccac cacccaccac ccaccaccca ccaccatcac ccaccaccta    1620 cacccacca cccaccacca ccaccaccca ccacccca ccacccacca ccaccaccac      1680
ccaccaccac ccaccaccac tacccacccct caccaccaccac caccaccgcc acccaccacc 1740
caccaccatc acgcactacc aaatatgtga tcatcaaagg tagaagctta caacttgtgg    1800
aaagacagat accactctct ggcctggggt gggaggacag agtatgactc gtcctcaggc    1860
aggttggctt cctggatgat cagagaagta gaatctaggg tgaaatgaaa caaaagtaga    1920
tggagaaatc tcaacaggac caagtagaga gggagaattt aggaattaag ttagactgca    1980
gcaaaagaat tcactgggtc tctggcccta ggctaaaaac tatagaactc caaacctta    2040 atgggagggg gtacttcatg ggcatgtct aagaggagtg aggaatgagg ttaatgtgat    2100
tctacggaat tagacagaag tctgtatggc tgaatgtact gggtttaaca gcaacgtttt   2160
agttagtttt tgatattatt gcaatgatgc actccagcag gagacaaatc ctggcaggat   2220
gcatggttca aagaaatacc aatctttcaa gagtatgttt aaacaaattt cactataaaa    2280
gactatatct ctgggaatgt caagcaattg gttactttag cagaaaaaa aaaactagcc    2340 atgtgacaac atggggataa aggaaaataa acacagtgga catgttattt tttctgaaag    2400
taaaatcgag ccatttcctt tcataatcta gtacagtcat gtgagaaatt ctgcttcatg    2460
gtgatctcaa gcaacagttt attggtggtg tggtacccaa tagattgtgg gtatggttgt    2520
aaatatacta aaaaacatta aattgtatgc ctttagtggg taaatttat ggcatgtaaa     2580 ttatatctca ataaagctgt ttaaaaaaga aaaagtagga aacaaaataa accaaataaa   2640
```

```
agtactaaaa tcacccataa ttaattccac catacagaga taactgttaa catttgttta    2700
aggttttctt gtttgctttt tctaatttgt aaaagtcata tacgttcatt aggggaaaaa    2760
gaccacttag aaatgtttgc ttgggccggg cgcggtggct catgcctgta atcccagcac    2820
tttgggaggc caaggcgggg ggatcacgaa gtcaggagat cgagaccatg gtgaaactca    2880
gtctctacta aaaatacaa aaaagtagcc aggcgtggtg gagggcgcct gtagtcccag     2940
ctactctgga ggctgaggca ggagaatggc gtgaacccgg gaggcagagc ttgcagtgag    3000
ccgagatcac gccactgcac tccagcctgg gcgacagagc gagactccat ctcaaaaaaa    3060
aaaaaaagaa atgtttgctt gaagaagaaa gtgaaagata attataatct caccactgac    3120
agacaaacat tttaacagct tgctgtgtat ctttccagac ttttaaaaga catagattta    3180
tatataaacc agttttgaca aaaatgggct aatactatgc atactgcttt gtaaccttta    3240
aaagtacatt gtgaatatat tataaacatt ctttcacata aatgtttatg atagaaatat    3300
aaatatattt taagtgaatg ctttgctctc aagtcaaaga tcaatattcc taactttacc    3360
ggaacccact agaattattt gctgttgggt cagttggatg aaccctaagt atctttggct    3420
gcttttcagg ttggctctga cacgttttat tccttcaagt acgaaatcaa ggaggggat    3480 tgtcctgttc aaagtggcaa aacctggcag gactgtgagt acaaggatgc tgcaaaagca    3540
gtaagtgtat tggccattct tgggccttct gttttctccg ttgaccctgc cagattttt     3600 tactgatgca gaaatgatgg ctactggtga gcctgtttat gagaaatgca aataaacatt    3660
ccaatgtgta gaaagtcag atgctttata tctgtgttct tgtatagaca gaaaaatcat     3720
ggagaagcca gcagttaaac atggagaaag ccttccatg agaagggggc tctagtgtcc      3780
agccagaaca tgtggctcag actccagaga gataacaaat tgacatttgg gccaagccaa    3840
agagctggcg aggggagggg gtgggtgctt ccattgcaca acgttaagtg caaatcttga    3900
ctctgccttc cattagctgt gtgatagcgg gggagctgtg acctctcaga actggcactt    3960
tctgctgtat atgggagata atattgacct catcaggttg ttggaggatg aaatcagatg    4020
aattatgcaa ataactttga taacaatggc tatcttaacc aaatgcctaa catataggcc    4080
tggcacacca tagctggttg ttgttttgct tttttttttt tttttttttt ttgagccaga    4140
gtctcgctct gtcgctcagg ctggagtgca gtggcgcgat ctcggctcac tgcaagctct    4200
gccttccagg ttcacgccat tgtcctgcct cagcctcctg agtagctggg actacaggca    4260
cccaccacca cgcctggcta attttttgtg tttttagtag agaccgggtt tcaccgtgtt    4320
agccaggatg gtctcaatct cctgacctgg tgatctgcct gcctcagcct ctcaaagtgc    4380
tgggattaca ggcgtgagcc accacgccca gccatggttg ttttgcttta attaagaaag    4440
atttcagaca gtatctgcct cagaagcaag cctctctttt catggattga ttcccttctt    4500
ttatgtcaga acataaaaga tgactgccag tcatctgcca ttaccaaaga gtactgaact    4560
ccaagtcagg agtctaggat tttgcagtgc tggttctccc ttctcagtca tctcatctgt    4620
aaggtgggga taagtagctg ctgtgctctg tactgcctgc ttctaggggc tgtgtggaca    4680
aagggaggtg tgctttatcc tgatggaata gtatctgtca cttagaatcc aatggatatg    4740
actgaagaat gaaaagacaa aacaaaacaa aaacactgtt caacaataac aattaaacag    4800
ctgcctatta ttaagtgcct gctgtgtggc gggcctctag taggcatttt gtgtgtgttt    4860
gcacacatac tgttcacaac aactctaaga gatagatgta tcccatcttc tacaagacgg    4920
gtaaactgag actccaagag tcaaggggac atgacagagt taacagctag caagtgacaa    4980
```

```
ggctggaact gaataacatt ttgatgccaa ggtccttgcc ctttctatta agttaaactg    5040
aagtttatgt gaacagtatt aactcactga agttgagtgg tagataagag gagtgtttag    5100
caggctggtt ctagacctct gcgtccatct tggttagaaa gaaatagctc cagagctcag    5160
ccaggtgcag tggctcacac ctgtaatcgt aacactttgg gaggccgagg tgattggatc    5220
atttgaggtc aggagtttga ccagcctg accaacgtag tgaaaccctg tctctaccaa    5280
aaatacaaaa ttagctgggt gtggtggcac gtgcatgtaa tcccagctac ttgggaggct    5340
gaggcagcag aatcacttga atctgggagg cagaggttgc agtgaaccga gagatcgcac    5400
tgttgcactc cagcctgggt aacaaaagca acactctgtc tcaaaaaaaa aaaaaaaaa    5460 aaaaaatagg aaacaaaaga aaaagaaat accctccagg gctcaaaaca aagactcaag    5520 cttttaaaacc tcatcattta cactgtcttt cctccagcat ctcatgaata tcagtggctt    5580
atataaagta atcattaggc tattaaaaaa atttattctc atgtctcaaa actcttttgg    5640
taaaatcttc acaagttttg ttttgttttg cttttttaagg aaagccacat ttagcaacag    5700
tattaggtag actttcccat ctgaaagatt aagataaatg atctctttct tttcttttta    5760
ggccactgga gaatgcacgg caaccgtggg gaagaggagc agtacgaaat tctccgtggc    5820
tacccagacc tgccagatta ctccaggtgg ctggtttatc ctctggcact gccctggtgg    5880
gaaattaacc atttctgtga gccaggaaca caatcttgac caggctctgc ttgctcccag    5940
agggtggcag tagtaaagcc atttgcagag ttagggagca ttgggtggag cggcagagcc    6000
cggaggttga gccaggcttg tgaccatcat ccccttagga ctatcccaac tcttcccgtg    6060
tgctgcattg tacccagtgt gtgcaagggc tcaacagaag gaccagaaga cataagacct    6120
gccctccatt gcaggcagca tcccagattg aggagcgcat aggctttgag ggcagacctg    6180
gcctggaatc tttcagagct ccttgccttc ttgcctctcc ttttccttgt ctagaaaagg    6240
gaggtaagag tacttcccac ttcacaggac tgttgtgagg ctgaaatgag atgatatgcc    6300
tggaggtaca atcataataa catactaaca tattaatcat aataacatat tagcaacaat    6360
caggataaaa gtaatagcta agatatattg agtccttatg tcccagccat gactcaaagc    6420
accttacatg tattatcttc ttttttcttt tttcttttac tgatacataa tattttacat    6480
atttatgagg tacatgtgag tgttttttac atgcattgaa cgtgtaatga ttaagtcagg    6540
gtatttgggg tatccatcac ctggaatagt tatcatttct atgaattggt aatatttcaa    6600
gtcctctctt ttagctactt tgaaatatac aatatattgt tgctaactat agacactcta    6660
gtctgctatg taacattaga acgtatttct tctatctaac tataattcag tacctattca    6720
ccaacctctt catttccccc ttctacccgc ttaccccgct cagcctctgg tatctgtcat    6780
tctcttctct tctctatctc catgtgatgg ttttagcttc cacatgtgag tgagaacaat    6840
gtgaagtttg tctttctgtg cttgagttgt ttcacttaac gacctctagt tctgtccatg    6900
tggctttaaa tgatatgatt tcaattcttt gtttacggcc aaatactatt tcattgtgag    6960
tatataccac aatttctttc tttttttttt tcatttgag acagagtctc gcactgtcgc    7020
ccaggctggg gtgcagtggc acgatctagg ctcactgcaa cctcccgggt tcaagcaatt    7080
ctccagcctc agcctcagcc tcctgaatag ctgggattat gggcatcgcc accacgcccg    7140
gataattttt gtgtttttag tagagatggg gtttcaccat gttggccagg ctggtctcga    7200
actcctgacc tcaggtgatc cacccgcctc ggcctcccaa agtgctggga ttacaggtgt    7260
gagccactgt gcctggtccc ccacattttc tttattcatt cacctttga tggacattta    7320 agttgatttc atatctttgc tattgtgaat actgctgcaa caaacctggg agtggaagta    7380
```

```
ccccttttgat aggctgattt actttcctct gggtagatgc ccagtagctg gactactgga   7440
tatatggtat ttggtgtttt cattttttga ggaatctccg cactattttc catagtggtt   7500
gcactaattt acattcttac caacagtgca ttagagttct cttttctcca tatcctcctg   7560
gctgtgttta ccgcttacat ggcaggcagc gagagctctg tggtgaagaa gtccaggctc   7620
ccagggggtc cctccaggtg tgccactcac tctgcagcta cgttcccttt ttatggactt   7680
tgcctctatt gaccagtagg ttagggctat ctgttatgaa cattacttga taatttaata   7740
caaactcttt ttaataatag ccattctaac tggggtaaga tgatatctca tctcataatg   7800
gttttgattt gcatttccct aatgcttagt gatactgggc attttttcac atatctgttg   7860
gccatttgta tgtcgtcttt tgagaaatgc ctactgagat catttgccca cttttttaatg   7920 ggattacttg gttttttttat tggtgagttg attgaattcc ttgtatatgc tggatgttag   7980
tcccttgtgg gatgcatggt ttgcaaatat tgttttttctt tcttttttttt tttcttttga   8040 gacacagtct tgctctgtcg cccaggctgg agtgcagtcg catgatctcg gctcactgca   8100
acctccgtct cctgagttca agtgattctc ctgcctcagc ctcagccccc cgagtagctg   8160
ggactatcac attcagctaa ttttttgtatt ttaaattttg taattttgta ttttttaggag   8220 agatgggggtt tcaccatgtt agtcaggctg gtctcgaact cctgacctca ggcgatctgc   8280
ccgcctcagc ctcccaaagt gctgggttta caggcatgag ccaccacgcc cagcctcttc   8340 tttgttttagg gcagtgtatg cgaatgctga ttgcgatcat taatgctgtg ttttttgtctg   8400 ctctttgtta agccgagggc cctgtggtga cagcccagta cgactgcctc ggctgtgtgc   8460
atcctatatc aacgcagagc ccagacctgg agcccattct gagacacggc attcagtact   8520
ttaacaacaa cactcaacat tcctccctct tcatgcttaa tgaagtaaaa cgggcccaaa   8580
gacaggtttg ttcttttaatt ctctaagtag cacagtatta ctaaaatttg ttagatctttt   8640 acatttaaaa tgtatgattg catggctggt ggtgttttca tgtgactagc acaggaagcg   8700
aagagctttc tccttagtca aagtgagtcg gatagtgcaa tatgtaaagt gagaaaagat   8760
gtcgaatcag accccccttcc tttgatgttt gattttaaca aatgggtaat cgtcattaca   8820
ggctcttcct agagacagtg aaaaggaaaa gtcataccgg ccttaggatt ttttttttttt   8880 ttttttttgag acagagtctc tctctgtcgc ccaggctgga gtgcagtggc gcgatctcgg   8940
ctcactgcaa gctccgcctc ctgggttcag gccattctcc tgcctcagcc tcctgagtag   9000
ctgggactac aggcgcccgc caccacactg gctaatttttt tttattatta ttattttttag   9060 tagaggcggg gtttcaccat gttagccagg atggtctcaa tctcctggcc ttaggatttt   9120
aagaaaacta tattatcacc tagccatcat gacttaaaca cagctccaaa atattaaatt   9180
gtgtctaaaa tggtcggcat ggctttctgg gtacccacta agttacagtt cccatatcat   9240
cagaaaaaaa aaagtatata tccgtaattt ttttttttttg acagtctcgc tctgttgcct   9300
aggctggagc agtggcgcga tcttggctca ctgcaacctc tgcctcccag gttcaagcaa   9360
ttctcctgcc tcagcctccc aaggaactgg gattacaggc gctcatcacc atgtcttgct   9420 aattttttgta ttttttagtag agacgaggtt tcaccatggt ggccaagcgg gtggtctcaa   9480
actcccaacc tcaagtcatc ctcccacctc ggcctcgcaa agtgctggga ttacaggcct   9540
gagccactgc actcagctac aaatcttctt aatgattcag tacacccaga cttttcttct   9600
tttttttttt tttttttttg tttttgagg aagagtcttg ttctgttgcc caggctggag   9660
gctggagtgc agtggtgcca tcttggttca ctgcaacttc cacctcccaa gtttaagaga   9720
```

```
tctcctgcct cagtatccca agtaactggg attacaggca cccaccacca cgcccggcta    9780
attttttgtat ttttggtaga gacaaggttt ccccatgtcg gccaggctgg tcttaaattc   9840
ctgacctcag gtgttcctcc cgtctcggcc tcccaaagtg ctgggattac aggcatgagc    9900
caccacgccc gcccctccca gacttttctg atagttgact gggtctcttg tatttcagcc    9960
tcttattatg agtgattccc tttggttagt aacattctct gcatttaata aaccttacaa   10020
cttgctttca tgcgagcatg ctttactcaa ttatgtccgt atagtgctat cagggtggga   10080
gaggcccaga ataaagtaga agaaatctta ctacttggta acctgggagc ctgaggaccc   10140
aacagtaaag accactcccc tctaaagttt tctttatccg tctagaaggg cattattatt   10200
ttatgaaatt cagtaaacat ttctctctgc agcctggcag aggaaatatt gttaggattc   10260
acttaaggaa atccatgttc caaaactggc tgaaaaatag aaaaatatat atattgcttg   10320
tcattttcag atggctagcg gtgtatgtgt gtgtgtgtgt gtgtgtttgt gtgagagata   10380
tgagactctt aaggtgctca atgtttattc agcattttt tgcctagtaa taataatatt    10440
ttatatttct tgggcactta tatattgcc acactgtttt ctaaactcct cataacattc    10500
atatcccaca gcgaataatg tttaaactgc cctttaaata ttcaatctga aattgtttca   10560
ggtggtggct ggattgaact ttcgaattac ctactcaatt gtgcaaacga attgttccaa   10620
agagaatttt ctgttcttaa ctccagactg caagtccctt tggaatggtg taagtaggca   10680
aaaatttaat gataaagttc ttagcatttt gtttacattt tgtggtaact atcaagctgg   10740
gtgggaagac tgtcacgaaa agtttagatg acattcagca attcatattc acatttactt   10800
gggaagacta aagctcacgt cactggtcaa gctgccttac ctaactggcc aaagaatctg   10860
cacagctagc aataagtatt tttttataac tttattttat tttatttatt ttttgagaca   10920
ggatctcaat ctgttcccca ggctggagca cagtggtgtg atctcatctc actgcagcct   10980
ccacctcgca tgttcaagct attctcctgc ctcagcctcc caagtagcta ggactacagg   11040
cgccaaccac cacgcatggc taattttttgt atttatagta gagacagggt ttaccgtgt   11100
tagccagagt ggtctcgaac tcctgacctc aggtgatccg cccaccttgg cctcctaaag   11160
tgctggtatt acaggcatga gccaccgtgc ctggccagca ataagtattt acagagcata   11220
accagggact acgaatagat aaaatgcttg aacggtcaac tgtatctttg ttatgtctcc   11280
acactttccc atttccttt cttccccagg tgctcaatgc ccatatggtg ttcccttgct    11340
ctacccaggg ttattcttca tgtcaaactt ttctctgttt gttttctcat cttcccttcc   11400
ctacctttat ctttaataaa cagacccctga gtctctagcc cttagtggtc cttcttagca   11460
tcgtatcttg ttatctgaac caaaattata ttaaaatggt atatctcaag gtagtagtag   11520
ctagcgaatg ttaagatggc gaagacatga tatgtgccca gggatgtttg catttgagca   11580
gaagactgtg ctttagccaa ggaaatgctg caagtccttt gatctagtaa ttctgcttct   11640
aattcattta tatgggaaat ccagaccata agatgttaat gtcagttgtt ttttaataga   11700
aaaatattgt aaacaaatag tttatgcaac attacagaat ggttaagtaa attacagtat   11760
atccatacag tagaatatga tacagctatc aaaaattttt agttttagt gacatagtaa    11820
aacggttaca atgttaagta aaaaacaaaa aaagtgggat acaaaactat acatacggat   11880
ttatttaaat atgtaaaata aatgtaaata caaaaagtga tggaaaacaa attatgacaa   11940
aatatagaat gtagttaact ttcagttgga attgtgggtg cttttctttt tttgagaaga   12000
ggtcttgctc tgtcacccttg gctggagtgc agtggtgcga tctcggctca ctgcaacctc   12060
tgcctcccag gtttaagcaa ttctcatgcc tcagcctccc tgagtagctg ggattacagg   12120
```

```
cgcccgctgc aacgccaggc taattttttgt attttgggta cagatggggg ttttgccacg   12180
ttggccaggc tgttttcgaa ttcttgatct caggtgatcc acccaccttg gccttccaaa   12240
gtgctggtat tacaggtgta agccactgca tccggccgct ttttctgatt ctttatattt   12300
tttggaagtt tttgatattt cccgagtttt ctaattgagc atgcatttat tttataattg   12360
gagaaaaaag taaaaggac actatcaaga gagtaaaaat acaacccaca gaatgagaga   12420
aaatatttgc aaatcatgta tctgataaga gtttaacatg cagaatatat aaagaacctc   12480 ttttttgttca taaaataaca agtattagaa agggcatgga gaaattagaa cttttgtaca   12540
ttgctggtag gactgtaaaa tgctgcagcc attatagaaa ataatttggc aatttctgaa   12600
aaacttaact atagaattac tatgtgaccc agaagttgca ctcttaggta tatgcccaaa   12660
agaactggaa atgcatattc aaacacgtgt ttatacatga atttctatag cagcaaaatt   12720
cataatagcc agaaagtcaa acaaccccaa gtgtctatca ataggtgaat ggataaacaa   12780
aatgtgctat tatatataca caatgaaaca ctgttcaccc tttaaaaga atgaaattct   12840 gatacatgct acaatgtgga tgaagcttga aaatatttatg ttaagtgaaa taagccagac   12900
acacacaaaa aatattgtat gattccactt atataaaaca cctagaatag gcaaattcag   12960
tcagagacta ttggagttgc tagaaatgta atgtaggctt ttctttttt ttttgagact   13020 gagttttggt cttgttgccc aggctggagt gcaatagcgc gatcttggct cactgcaacc   13080
tccgcctccc gggttcaagt gattctcctg cctcagcttc ccgagtagct gggattacag   13140
gcatgtgcca ccacggccgg ctagttttgt atttttagta gagatgaggt ttctccatgt   13200
tggtcaggct ggtctcgaac tcccaacctc aggtgatccg cctgcctcag cctcccaaag   13260
tgacttatca cacagcacct ggctatgttt gtttattatt ctttttttccc ctcacttctg   13320 gagacctagg cataggtctt tctatttgtt tgttctattt gtttgttcta tttgttttc   13380 tccctctgtt tttaaattat gaaatcatgt cgagtcaaaa attaacttag aatgctgttc   13440
taataacatt atatggaatt ctcattttg ttattttgtt tttttttcc ttatccaaga   13500 aagaccctaa cttttattggc aagcatgttt atatttccaa gtatattgtt tttgtttgtt   13560
taaacatgtt atgaattttt agagattatt ttttctttt ggtgctgagg tgaaagaaca   13620
taccctgtat tgtttctgct ttgtaaaatg tattggatct ttttgtgacc tggtgtaaaa   13680
acaattaaaa atatttgtat gatactggcc gggcacggta gctcatgcct gtaatcccag   13740
cattttggtg ggtggatcac ttgagatcag gagttcgaga tcagcctggc caacatggca   13800
aaacctcatc tctactaaaa atacaaaaaa attagccggg tgtggtggca gacgcctgta   13860
atcccagaca cttgggaggc tgaggcagga gaatcacttg aatccaggag gcagaggttg   13920
cagtgagctg agattgcgcc actgcactcc agccttggcg acaaagagag actccatcac   13980 aaaaaaaaa aaaaaaaaa aaaaaaaat atatatatat atatatatat atatatatat   14040
acacacacac acacatatat atatacacat atatatatac acatatatat atacacacac   14100
acaaatacat acaaattagt atgatactta tgaaagtatc atttaaaatc atatgtagca   14160
tatgaaaata ccatttaaat aaatcttaa tatgttattc aaatcttcta tgttcttgtt   14220
tattttttat tcacttgccc tgtcttagat ttgtaattgc atactaaatt ttcccaccat   14280
attattctta tccatttcta ttcacgtgta atttttcta ctttaggtat tttgattcca   14340
tgccttctgg tctatgcttt tgaaaaataa aatgatcatt tttactacct ttaggaatga   14400
gtgttttgtt ctcgtgaatt ttactttgtc caatattact aatactgtag ttcctgctac   14460
```

```
gtttatattt gtctcacgta gctttgttca tctgttattt ttaagcttta tacattgttt    14520
ttatcataag atgattcttg aaactgtaat acattgattt ggtgttttaa cagtgtgaaa    14580
gtcttacctt atttttttag aaatttacct ttttacttac atggctgtta tttctgtact    14640
agatcttcct gctttccatg tgctcatgta tatgcatgta tttgttgatg ctattgatac    14700
tattacctta gtatctcttt tgcagtaaga ctatgttttg cttctttctt ttttttctat    14760
gcaatgattt ggaaagtaca cgtcctattc ttcaatttta ctagttgttt acttttaaga    14820
ctctaaaaaa tgtttttaac tgagcactta tatgcttttt aaaaaccagg ataccggtga    14880
atgtacagat aatgcataca tcgatattca gctacgaatt gcttccttct cacagaactg    14940
tgacatttat ccaggtaagg aataacacat gttggcaccg caatagagga atagtggtcc    15000
cagacaactg gctgagtctt ttcctataag ttgggttttg gttcccgtga tatactccaa    15060
agtctgtgta acctgcagac acagatgcac cccttgatga gaacactgta ccccttcgct    15120
gcccagttgt gctgcagctc agactgttct tgtcagaatg gtttatgaag acagaaggga    15180
aatgtatgac ccctgggcaa agttggcctt tgggtacaat gccatctggt ctctcttctc    15240
tgtaagttgt ccttaagtca gatgttgtaa gttgaagaga cctgtatttt atttctaagc    15300
actcagaaca aaacccttc aattaaggtg gttttttcct gcatgttata atgggaagaa    15360
atggagatag tgtgagtttg tggtcaggtc agtgtttctt ataacaaggg tgtgcttttc    15420
tcatagttgg aaaacgtttg tatgcgttcc atgagtagtc tgaagctgcc tgttcatcag    15480
aaccatagca cttaaacttt tctcatgaga gtcactcctt taaattaagc attgcttttt    15540
acagtttcca tcaaaaatgc aaaaattcag gaaaagtgta gcgttttgtt ggagttactc    15600
gcactttcct attgaaaatg tttccctaag tacactgtgc tctgaggagg agaaaagaag    15660
agaggcagga agtgaaagtc agacagacaa ccttcccca ctcactactg ggcctgggct    15720
cccatgtagc cccttataca tgtggatgct ggttcttgtg caggagggat gctaggccag    15780
gctgctactt cagtgtacat gttgacttaa aacctgatcc tttcagggaa ggattttgta    15840
caaccaccta ccaagatttg cgtgggctgc cccagagata tacccaccaa cagcccagag    15900
ctggaggaga cactgactca caccatcaca aagcttaatg cagagaataa cgcaactttc    15960
tatttcaaga ttgacaatgt gaaaaaagca agagtacagg tgtgtaaact atactacaaa    16020
agcagtaaca ctatagtcta tgtgcaaatt gctgactaat tttgccactg atcttggctc    16080
tggattggga aaccatacat ttgataatgt gatttggtgc attagatttg gtaaattaag    16140
tgccaatctc cctgtatgct tcatcccgga caagtatttt acaacattct ctctgttttc    16200
tatatgtaaa ggactgaggt gaggatcaaa taagttaata tatgtcaaat cactttttca    16260
aactctaaaa tgctatataa atacaatagc agctgggcgc ggtggctcac acctgcaata    16320
ccagcacttt gggaggccaa ggcgggtgga tcacaaggtc aagagatcaa gaccatcctg    16380
gccaacatgg tgaaaccctg tctctactaa aaatacaaaa attagccggg tgtggtggtg    16440
cacacctgta gtcccagcta ctccagaggc tgaggcagga gaatcgcttg aacctgggag    16500
gcagaggttg cagtgagccg agattgcgcc actgcactcc agcctggcaa cagagcgaga    16560
ctctgtctaa ataaataaat aaataaataa ataatacaa tagcaaccat gatataatta    16620
ataaaattca gggctagggc caggaagact tacgctatgt cttctggac tcatctctca    16680 ttataacatc acataatgtc ttgggctcag ccatatcagt caatccatca ttgccaaggc    16740
tccacgcttt cttgcctcca tgtctttcac ctactgttct ctctgcctgg gatcccgctc    16800
tcctgcaaat gtaccctctg gggattcatc tctcctttca tgccctatca atagaagact    16860
```

```
gacaggagtg tcttctggga gtcaggagac tcagttccac catagcatct gccgctcaca   16920
tcccagatca ctctgggtgg tcattcaaac gttctaagcc tttgtggccc cgtctgtaaa   16980
atgagtgact gtattagaag agcctacatt ttgccgggca gagtgcctca tgcctataat   17040
cccagcactt tgggaggctg aggcaggcag atcacctgag gtcaggagtt cgagaccagc   17100
ctgaccaaca tagagaaacc tcatctctac taaaaataca aaactagcca ggtatggtgg   17160
tacatgcctg taatcccagc tactcggaag gctgaggcag gagaatcact tgaacccggg   17220
aggcggaggt tgcaatgagc cgagaccgtg tcattgcact ccagcctggg caacaagagc   17280
aaaactcctt ctcaaaaaaa gagaagagcc tacatgtcta gcaactccaa tagtctctga   17340
ctgatgtcat tatggacaga cccctatttt agagactaaa aattggcttc cctaaataca   17400
agctaaataa aaataatcaa aatagagcca aattgttaca gcaagccaac ataatcctca   17460
taatctggtg aaaaaattct cactaaaaag ttcatacttt tggctcagaa ttgaatttct   17520
aggaatctaa agtaggagtc tttatataca atgatattca ctgcagtttt aagtataaca   17580
gcaaaaatag taaactgtca aaatgattaa tatgagaatg attagatcat gtctggcata   17640
tcctcagaat agagtgttaa gcagcaactt aaaagcatct ttgtgcggag ctcttgatat   17700
ggggaatgtc ttgtgttata atattcagtg aaaaaaagga ggcataaaat tgaatataca   17760
tgatgttatc agttgtgtta ttttaaagta cagaaaataa tgtgggaaaa aaaagtggct   17820
cacgcctgta atcccagcac tttgggaggc cgaagtgggt ggattgcttg aggtcaggag   17880
tttgagacca gcctgggcaa catggtgaaa ccccatctat aatattaggt tggtgcaaaa   17940
gtagttgtgg ttttttgccaa agtaatggca aaatcacaat tacttttgca ccaacctaat   18000
aaaaattcca aaattagcag ggtgtagtgg tgcacacctt caatcccagc tactcaggag   18060
gctaaggcac aagaatggct tggacccggg aggcggaggt tgcagtgagc cgagattgtg   18120
ccactgcact tcagcctggg cgacagagtc agactccacc tggaaacaaa caaaaaaacg   18180
aatgcctcat agtcatagtg gtgattttta ggtgatggaa taacactact ttaatctttc   18240
taattttctg tattactttt gtaactgaaa aaaagtaaac aaactagatt aaagtaaatc   18300
aaaactgata ctttgatctc tctgctactt gagcacttgt ttctatccca gacacaacca   18360
ccctctctct ctgatttcat tgccatatga ccacgttagg tttacttgaa agggacgcca   18420
atctatgcta ttcatgcttt tttcagcttt aacttctcac tttatatttc tgctttcttg   18480
tgaaattatt ttattctttt ttcgttgttg ttttttaaga gagacgcggg ccagacatgg   18540
tagctcatgc ctgtgatccc agtactttgg gaggcagaga caggaggatc acttgagccc   18600
aggagcgaga ccagctggag caacatagca agaccctgtc tctacaaaaa aagaattaaa   18660
ggccaggcgt ggtggctcat gcctgtaatc ccagcacttt gggaggccga ggcaggtgga   18720
tcacctgagg tcaggagttc gagaccagcc tgaccaacat ggtgaaaaac catctctact   18780
aaaaatacaa aaatcagctg ggtgtggtgg tgggtgccta atcccagc tactcggag   18840 gctgaggcag gagaatcact taaactcggg aggcggaggt tgcagtgagc aaagatcatg   18900
ccattgcact ccagcctggg tgacaagagt gaaactccat ctcaaaaaat aataaaaaaa   18960 aaaagaatt aaaaaattag ctgggtatgg tggtatgtgc ttgtagtccc aactactttg   19020
ggaagctgaa gtaggaggat tgcttgagac tgggaggtcg agactgcagt gagctgtgat   19080
cgtgccactg cactctagcc taggtgatag aacaagaccc tttgggcaac agagcaaaca   19140
aaaagagaga gagatggggg tctcactatg atgcccaggc tggactcgaa ctcctgggag   19200
```

```
caagcaatgt gcccatctca acctcccaag tagctgggat tacaggcgca caccaatgca    19260
cccagctccc ttattctttta ttctgaatgt tgtaggaata ggccaccatg tattgtatgt    19320
cagaggtttg ccatcaaaaa cagaaccact cattctcaag catgaatatc tagtcttctt    19380
agtagttaca gttttctctg tggattaatg aatcaacatt ctagtatgca tatgtgtcta    19440
cattaaggat gtcaggggga cacaaagagg taacccatca gatagctgcc aagtcaatct    19500
gaatattgca agaatttcaa acttacttta gagagataaa tctttactaa ttttttgcatt   19560 taaagagagc aatttggttg cttggacata gtcacccaag gcagccttga tggaagcagc    19620
caatttactg gaaatcaatt aaacatatga tgaatttgct aaaagctagt ctccaaaatg    19680
accaatttgc caaattgcta aatatttata gttttaatct tgccttgggt ttgcacattt    19740
agtcctgttt ggatgcatgt tgattccacg ttgggttcat atttcagata tgaaacactt    19800
cctgaatctt ccatttttcac acattagtga ttacagtttc atataagttt tattttgccc    19860
taccaccact gctgctgtcc ccaaggctgt tgatgctcct gtctgcctct gctgagatga    19920
ataaacttcc aagatctgtg tgtgcacatg cagaaatttt tcctttgaca aagtcctagg    19980
aatgtcaaat aatatgtaga tatataagac ttgatgcaaa ttgccagaat caccaaatat    20040
ttgcaatgat gccaatttac attcacatca cctgggtata agacaccagt tgaggccagg    20100
cgtggtagct catgcctgta atcccagcac tttgggggggc cgaggcgggc ggatcacctg    20160
aggtcaggag tttgggacca gcccagccaa catggtgaaa cctcatctct acaaaaaaca    20220
caaaaattag ccaggtgtgg tgacacttgc ccgtaatctc agctacttgg gggcgctgag    20280
gcaggagaat cacttgaatt taggaggcgg aggttgcagt gtgtgtcact gcactccagc    20340
ctgggtgaca gagtgagact ccgtctcaaa aaataaaaga aaaagacac cagttgagga    20400 tcttaatttg aattctcttc ctaccagcag tgactgaggc tgcttgattc ctatgcctgg    20460
ccaatgccac gtatcatcaa ttttttgtttt catctttgcc tgcatggaag gctaacaatg    20520
atgtctcatt gctttttttaa tgtgcatgtt tttgtttatt aatgaagtta aacttttttt    20580
taggcttaat gaccgtttta acttctctga aatacctgct catggctttt gtccatttttt   20640 agtgttgggc tttatattca tacagacatt gattctatat catagttttc ccagcttgcc    20700
tttctacttt gcttattgtg attttttcaga agcagttttc attttttctct agtcaagttt    20760 tagtattttc cccttccttc agatttcttt cctctgcttt tcacctaaga aaggccttcc    20820
tcatcctggg ttttggtgaa tatttattta tttgtttagt tgttttttgt ttgtttgttt    20880
ttgttttgtt ttgtttcccg aaacagagtc tcactctgtc acccaggctt gagtgtagtg    20940
gcgtgatctt ggctcactgt aacctctgcc acccaggttc aagcgattct cctgcctcag    21000
cctcccaagt agccgggatt agagatgctt gcaaccatgt ccggctaatt tttagtattt    21060
ttaatagaga cagggattca ttatatgtta gccaggacgg tctcgaaccc ctgacctcag    21120
gtgatctgcc cgcctcaggc ccccaaagtg ctggaattac aggcaggagc cactattccc    21180
ggccaacaca tttaaatact atgatttaat actaaataat ttggttgaga aattgggcca    21240
caaatatttt aatggaagat agtgttgagt agtgattaaa actgttgcta gagattaaaa    21300 taatttttttt ttcttttttga dacagagtct cactctgtca cccaggctgg agtgcagtgg    21360
catgacctca gctcactgca acctccgcct cctgggttca ggtaactccc ctgcctcagc    21420
ctgtcaaata gctgtcaaat tacaggtgtg catcacaaag cccatctaat ttttatattt    21480
ttagtagagg tgggggttttca ccacgttggt cagattggtc ttgaacagct ggccttaagt    21540
gatccacccg cctcagcctc ccaaagtgct ggaattgcag gcatgaacca ccacgcccag    21600
```

```
cctaaaataa tttcttaata ttaaaaatag taagagaaca ataaaaaccc caaataatttt  21660 ttctaattac aaaatttaat ccacataatt tctatagtag tactaactca gtatttcacc  21720
aattcaagat ttggcaggac aataaggcat atttaaaaac attttaagtt tttcttccta  21780
ttcctgttag attattagat attcaacttg agcccttga attactagtg aatttaacag   21840
ctgttggaca ataaaactca aataaataca taaataaata aaaattatag gccaggcatg  21900
gtggctcatg cctgtaatcc cagcactttg ggaggccgag gcaggtggat cacctgaggt  21960
cgggagttcg agaccagcct gaccaacatg gagaaacccc atctctacta aaatataaa   22020 attagccagg cgtggaggtg ggcaactgta atcccagcta ctcaggaggc tgaggcagga  22080
gaattgcttg aatccaggag gcggaggttg tggtgagccg agatcgtgcc actgcactcc  22140
agcctgggca acaagagcga aactccatct caaaaaaaaa aaataaagaa aattatagct  22200
tgcttatttc ttcccccact tagaaaagga aatgggacca accgatagcc aaatatttta  22260
aatatgcatg ccaagcttta atgccaaacg tgtacttttt tgtatgtaac tctctaagtt  22320
ggtcaattaa aatttcaaga ttctccctta acatttctta aagataaatg atttattatg  22380
caaatatttt taagcgttta ctttgtacta attaattttt caggtggtgg ctggcaagaa  22440 atatttatt gacttcgtgg ccagggaaac cacatgttcc aaggaaagta atgaagagtt   22500
gaccgaaagc tgtgagacca aaaaacttgg cgtgagtagt catgcacctg tctactttt   22560 cactggaagc ctatttgatg ttttagaat catttgttta aatgtctcgt gaataacact   22620
gtctctcttt cgacttctgt tttcatggat agcaaagcct agattgcaac gctgaagttt  22680
atgtggtacc ctgggagaaa aaaatttacc ctactgtcaa ctgtcaacca ctgggaatgg  22740
tatgattcta attacagtca gcgtggggtc agttctgctc attctgaaaa tccatatttg  22800
ggggctgaaa atgaaccatt actgaaatga attggggagc tatctttttt aaatggggag  22860
taactctcac acttctgtgc tgatctctgt ttaatggcta gaaagaagag taacaatcct  22920
cctgatcact tctcacacat tgtcagtgtc tcagtgaagc ttctatagac tctctcctag  22980
tgcactgcag tcctgctgtg ggggagcaac attggctatg ccaggtgtac ctgaggccag  23040
atacagcact ccactgcatt ctgctgacat gcaaggacca tgtgaaaaat gcatggctgg  23100
gcgcggtggc tcacgcctgt tatcccagca cttgggagg ctgaagcagg cagatcacct   23160
gaggtcagga gtttgagact agcctggcca acatggtgaa accctgtctc tactgaaaat  23220
acaacaatta gctgggtgtg gtggcgcctg taatcccagc tactcagggg gctgaggcag  23280
gagaatccct tgaacccagg aggtggaggt tgcagtgagc cgagatcctg ccactgcact  23340
ccagcctggg caacaaagag cgaaactttg tctcaaaaaa aaaaaagaa aagaaaaatt   23400 cagactcgca aaccccactt cacagctacc gaattttaac cagatcccca ggggattcat  23460
atgcatgaat caagtttgaa aagcattcgt tgatgtcatc tttctttttt aagtcttaaa  23520
agaactctgg gaggtagtaa cactttcct attgtcaagg atgagacact aaaaattaga   23580
aagactctga ggtcctgagt gaataatgac attatcaaat gcttcctctg tcccaggcac  23640
tatactgaag gtttcaccca cattttcgag tcctccttat aactctgtga ggcaggtgct  23700
gttattattt ctatttttaca gaaaggaaaa gtgaagctga tggcacttgg attcaaatct  23760
tggtcaattc agagtctacc ctttccatca cgatgctgat taccagtagg gtctggccgg  23820
actccaatga ccatgttctt tgcatcacca gacactgctt ccaattaaca cattctcaca  23880
ggtagcaaaa gtgtaggtag aattaatcca cagatcgaca tatttgaagc aggttacctc  23940
```

```
ttttccctct tttctgattt ggtcttttgt catgtgtagg tatgtagatg gtgtaacaca    24000
aacattgtcc tcaggttgca tttcaagctt gcgaatatgt cctaatgtgc ttcagcacaa    24060
caaagtgatc atggatacat gctccctata tattcagttc ataaagccac ttagggcctt    24120
ttaggataaa agcagtgatg gtggtaataa cagtagtatc aataattaaa tactgtgctc    24180
agtaaaaaca taggctcaga agctacccta gagattagct agttcaacca tccagatgaa    24240
gcaaaaacac tccagcttat tttacagttt tttttgttgt tgtttggctg ggttttttttg    24300 tttttttttt gttgttgttg ttgtttgttt tttgttttttt ttgacagagt cactgtcgcc    24360
taggctggag tgcagtggcg ccatctcagc tcactgcaac ctccacgtcc tgggttcaag    24420
caattctcct gcctcagcct cctgagtagc tgggattaca ggcatgtgcc accatgccca    24480
gctaattttt gtatttttag tagagatggg gtttcagcat gttggccagg ctggtctcaa    24540
actcctgacc tcaagtgatc tgctcgcctt ggtctcccaa agtgctgaga ttacaggtgt    24600
gagccaccat gcctggctat tttatggtat tattaacaac aataattaat gtccacaaat    24660
tttaagatca atcaaaagac aaaaaaaatt attcatcctt tctggaatgt taatatagca    24720
tttaaaatct ggcaaacacc tcccccattg taaactaaga taacattgcc agatctcagt    24780 gttttttttct atcatcaata gcatgatttt tgcagtaata cattcatctt aatattttct    24840
gtttagatct cactgatgaa aaggcctcca ggttttttcac ctttccgatc atcacgaata    24900
ggggaaataa aagaagaaac aactgtaagt ccacccccaca cttccatggc acctgcacaa    24960
gatgaagagc gggattcagg aaaagaacaa gggcatactc gtagacatga ctggggccat    25020 gaaaacaaa gaaaacataa tcttggccat ggccataaac atgaacgtga ccaagggcat    25080
gggcaccaaa gaggacatgg ccttggccat ggacacgaac aacagcatgg tcttggtcat    25140
ggacataagt tcaaacttga tgatgatctt gaacaccaag ggggccatgt ccttgaccat    25200
ggacataagc ataagcatgg tcatggccac ggaaaacata aaaataaagg caaaagaat    25260 ggaaagcaca atggttggaa aacagagcat ttggcaagct cttctgaaga cagtactaca    25320
ccttctgcac agacacaaga gaagacagaa gggccaacac ccatcccttc cctagccaag    25380
ccaggtgtaa cagttacctt ttctgacttt caggactctg atctcattgc aactatgatg    25440
cctcctatat caccagctcc catacagagt gatgacgatt ggatccctga tatccagata    25500
gacccaaatg gcctttcatt taacccaata tcagattttc cagacacgac ctccccaaaa    25560
tgtcctggac gcccctggaa gtcagttagt gaaattaatc caaccacaca aatgaaagaa    25620
tcttattatt tcgatctcac tgatggcctt tcttaattta agtggctatg ggtatttctt    25680
tcatacttta ttaaagtatc aatatccctc tctccattgt ccagatgaaa atatcctgat    25740
ataatgcacc aaaaaccatg cagcttcgga acagtctaaa gagaagtggt gagactccca    25800
gtggagacac catcagtctc cacggactgc ataaaattgt gtgccacaat tctaactctt    25860
ttctgaatct tcttcccaag ttttctaaac tagcacagta aacagacaaa ctaatgtgcc    25920
gtatggcctg ctgcaattgg cttctctgat aacaaatatg taccttacaa catatgtcat    25980
gaatttgcat acaaagattc ttgtcattct taataaactg tggcacttgg tatttgaatg    26040
tgtgtgaaaa taagggaagt caagagatta aatgctgaac ttattaatgg aatagaaata    26100
ataaggaggc tgaggctgga gaattgcttg aacccgggag gcggaggttg cagtgagccg    26160
agatcgtgcc actgcgctcc agcctgggca tcagagcaag attctgtctc agaaaaaaag    26220 aaaaaaaag aaataataag aaaaacttcc agatttcaaa gtaacaagaa agaagacagg    26280
ttggccaaag ggaggaaagg ggggacataa attaattgac tttctattcc caaaatgggc    26340
```

```
tagttatatc aaataaatac tcccactgcc ctttctgagt gagagtgttt ctcataagtc    26400
aaaaatttct gtttactcat taactactct ttgcaacagg ctttcatata gaagtattct    26460
gtttattttt gctgagccta gattgagtaa ttcttagttt acagaagctc cgagcttaat    26520
gataaggatg aaaagcagag ggagcaatat agaagcaggc ttgctaataa aactttttaa    26580
ataattgaca agggaatatt atggaatgtg atgcaaagtt tgttccgaaa ttttatgagg    26640
aaattactct ctagtctcac tttatagtct ttttgctatg actttgaaga ccattgattt    26700
ttgagaagca gaataatagg attgcctttc attgccctat agtgcaaaga aggtatatgc    26760
tttataacca atgttgtact tttgcctaga aaaacaagat atggctttaa atagctacaa    26820
tcatctttgg atgtatatgt cactgctgct tcaagttatt ggatgcattt gaacctctga    26880
gtttgtcttt cattttaaat attgtctgtt cttttaaata aacaaccaca gatgtcagga    26940
aaaagtctta ccttgtcaac tggttgctcc acttttaaaa aatgattgaa tgataacatc    27000
atattaactg cgttttacta tacttacaga gtcacctaag gtcctgcgag tacaagggtc    27060
gacccccaaa ggcaggggca gagccagcat ctgagaggga ggtctcttga ccaatgggca    27120
gaatcttcac tccaggcaca tagccccaac cacctctgcc agcaaccttg agaggaagga    27180
caagaagaaa gatgggatag aatttaaata gagaagaatg ccattttatc actctgcctc    27240
tgggtgaaat aaagatcagt cttgatgttc taactctaat tcacagtggt ctcctttcag    27300
ccctacccat tctgcagcaa attccagctg gtcagagagt cagtgctgtg gctctgccat    27360
ggaggctcat aacccaacac tggaacattc cctagccaag gcagaagtcc ttaggcggga    27420
cttccttacc accacgggtg ctaaaagaag agttagtagg tcatgcttct accagtaatc    27480
taaggactct ctccttctct tcttcctctt tctccagatt tccaagcctt agctaagagt    27540
aatttggctt gtttagtatt gttttcttat ggtccagtta attaccaaaa atatttttaa    27600
aatcatctct gttaatagaa tgtctaccaa cttctcacta tcagaaaata ctcaacctcc    27660
aaacaatttg aaattatctt tctgatccag gtaaagaagc aaattgaaaa tcaataaagt    27720
aaaaagtgac ggagatttta aattttctgt aataaaaaca cttattgggt tgggcatggt    27780
ggctcacgcc tgtaatccca gcactttggg aggccgaggt gggtggatga cctggcgtca    27840
ggagttcgag accagcctgg ccacatggcg aaactccat                          27879
```

<210> SEQ ID NO 10
<211> LENGTH: 9737
<212> TYPE: DNA
<213> ORGANISM: Homo sapiens

<400> SEQUENCE: 10

```
tgaggtcttg agtagttcaa cttgacccat gcagacataa tttgagagac gccaaggagg      60
attaggaaaa aatgtatctg gtcttactca actctgaaca ttgcatgagt caaacgtttt     120
cctagctctc tgtttgtgtg atgggtccac tctgatggat tcttggcgat gtatctttca     180
tgaccaaaat tcaaagagg ccattcgaag tggctcccac aaaagctgct gcagagcccc      240
agacattcag aagccaatag tgaaggggcc aaaagccatc cctcaatgtt cactgacact     300
ttgcgagcct tggggcaagt tggcgatgtc aaaacatgtt tttagggcgt gtttgccaac     360
atacaggtct tgggcaggat tgcagacctc tgcagatggt accaaagtaa aggggagat      420 ggtagctgaa taatctctta tcatcccctaa agtgcaaagt gaaatgagag tggatttttc    480
cttccaaatc cacttggagt gagtcccgaa agactcactt ttgcggcaat ccccacaatg    540
```

```
acatcactgg agcggaggtt atataattta aagcaaccac atctccacag cacttcccag      600
aagagaaaac tcctccaaaa gcagctctca ctatcagaaa acccaactac agttgtgaac      660
gccttcattt tctgcctgag taagtaaatg accaccttt tttttctt tatgagagta         720 caatatgaga ggaaatctgt gtctcttaga aaaacaaaaa acttccttt acacctacct       780 attggcaaaa ttttccactt ctgtgagggt acttttaaa ataattcta aatcaattta        840 agagactttt atttcatgcc tagtttgggt cttaattgct tttccagaac aggaggagga      900
gggaaaggtt ttagaactcg taggaaggtt ccagtagctc cttatatcaa agtcaggtga      960
aacatgtcag ggctgaatgc agccaccaga gttcgcatgg actgaccagt tacagcctgc     1020
aaattctgaa tcataaaaat taaattagtc tctctgggat ggcttacaag atttcataag     1080
accaataact ggttgggtta ttcgtggctt gaaagtagca tcttactatg tgaccgtgct     1140
gatggtcttt aacatctgtg gctgaatttc caatgccttt aacatcacca tgctgttgaa     1200
attggagtta atttgaagaa ttaactaatt tgttgaagaa agtcacactg tctcatagcc     1260
taggttaaaa tgtgcagaat tcagaaaata ccacacagga attacagaat tgccatctct     1320
tgtagacttg cccagtgccc cttctgagtt cttcaaatag ggtcacatat tactaacaat     1380
atccagagat attgtttatt gagcacctac tatgttccag gcaaatatca gagctaaagc     1440
tgaaaactgg caaggaaga tttctcctct ctagccaact ttataaacac agacagcagc      1500
aggtgaggac aatcccttta aaaataagcc ccatgtgagc agacacatgc tgtggctgca     1560
gtggccccag ccacctcccc gtcctgggga tggggcggt gtccactgac ctaatcaggt      1620
tcgagctaaa gtccctgcgt agctggtcgt ctctggcttc ctgggcaggg tgcagcctca    1680
cccccgtgct ggtttcctaa ggctgctata attaattatc acaaagtgag tggcttaaaa    1740
cgatgcaagt tattatctta cagttctgga gatcaggagt tcaaactcag tctcgctgag    1800
ctaaagtcaa gatattggct tggctttgtt ctccatcccc atgattcaat tatctcccac    1860
caagtccctc acacaacacg agagaattat gggagctaca actcaagatg agatttgggt    1920
ggggacacag ccaaaccata tcagtgctca acaccctccc atctcttctc aaactctcaa    1980
tgccccagcc cctccaccac aggtcaggac ctcgcctcct ttctccctga gaaatcccaa    2040
ccaatcgccg gggaattcta cagattccca cctgccagcc tctgtcacca tagacctcag    2100
cttcctggcc atcatcagag atagctagga gagggatggt caggccatgt gtgtgcacac    2160
tgccggggca ccccaatagt caaaaattat ttccccccaaa aattagtatt tacaggtaga   2220
aagagagagg aaagaaggaa ggaaggaaag aaggaaggga aggaaggaag gaaggaaagc   2280
aggatgggag ggagggaaga agggagggag gaagggaggg atggaggaag gaaggaagga   2340 aggaagggaag gagggtaggg agggaaggag agaaggaggg aatgaaggga aggaaggaag   2400
gaaggggaaa aaatccaaca aaatggttat attatattga tggtgttata aagtagttct     2460
agataaaaac tattttcaaa aaagtcttta aatatatatg catacaccta tgaatattaa     2520
agcaaaagaa aacatgttta tgttaatcaa ctgaacattt aaaaataaga taagcaaaat     2580
aattgttctt gttgtatatt cacatgctac agtttcttgt acctgactga taccctgtca     2640
ctggcatttt tcacaagaat gtattttctt cagtggggtc ttgttatttt taattttcc      2700 atataattgc ctgaaatctt ttttccacaa atttttacaat taacaaattt aaattagtac    2760
cttcaattga ctcttctctt gaaccataat atattgagaa aatgttccct gtgcaggttc     2820
tgagtgataa gctctcagca aattctgcca ggcagaggct gttctcaagt ccaattcttt     2880
gcatatggaa ttgcataaat attttagccc agatattttc acaggtgctg tctttgtgcc     2940
```

```
ttagtttgga atgtagtggt gcgatcttgg ctcgccacaa cctccgcttc ccaggttcaa   3000
gcaattctcc tgcctcagcc tcctgtgtag ctgggattac aggcgcctgc caccatgccc   3060
ggctaatttt tgtgttttca gtagagacaa agtttcacca tgttggccag gttggtcttg   3120
aactcctgac ctcatgtgat ccacctgcct cagcctccca aagtgctggg attacaggca   3180
tgagccacac cgtgcccagc ccacacgtat tttttttaa ccagattaaa cctttcaaat    3240
aagttgtacc tacttataag ttttgaatgt tttgtcagat tcagatactg caaaaaaaa    3300 aaaaatcatt ggctttctca atttcatctc atttcataca gaacatgaat ttatccaatt   3360
aaaaagattc ttcccacaag ctgaaatgtt ccagagctca ttttagaatt tcaaaattaa   3420
ctcttgtaca gcatttgatt ttgatcattt tctgatacat tttataattt ttctgcatac   3480
cagctttgtt ttcaatattt ataattcact aaaagctttg aaagttgacg ttttgctgct   3540
ctattcattg ataacttga ctaaatattt ccaactgatt tggaacaaaa ttcaacgaaa     3600
atttatagat ctgttttaat acactgttta ataacatttt aggatgctga gactcaatgt   3660
ccactaaaat tgattgataa tgggaaaata aaagagaaaa cacatgtgaa agtccagttt   3720
tttaaaaaaa ttcatgaaca actttatcac aagtttgtag ttcagtaaat ctgtgcatat   3780
gttttaacat tttgtaaatt ttgtcacgta cgtctataaa tgtcaattta tagaatattg   3840
acatttattt atatgcaata acaaattgtg tgtgcaccat gacctgttcc aatcacattt   3900
ctgtttcatt agtgtcttaa tttagtagga atattattgt taccatgacg ctggactcca   3960
ccacaatttg tgttttatcc tcacaaaaat gcaatgactt tatttccaat gtggaaaatt   4020
taaacaactt aaatagcatt cacaaaaagt cagttgtttc actttgccag aatgaatgtc   4080
ccaaagccct gcttggcttc catgagctga atgaaagaat gaattgtgat tggaattaac   4140 aggttttct gtctgaagag tccgaggata ctggtgttga gctggcacca ttttgctttc    4200
tgtgatgttc ttcttatgga gccaacacac agtcagccat cacttccact gttgcacgtg   4260
cacaagaaaa gctggaatta aatgtgagct gagttaactt aaagaacagt catttgatct   4320
aagggaaaag tcatgcctct cagaatgatc ttatatcagc atcttttgca gctacatgga   4380
tgagaaccgt gtcttagggt gcaatttttt tttttttttt tgagacagag tctcactctg   4440
tcacccaggc tggagtgtac tggtgcgatc tcagctcact gcaacctctg cctcctaggt   4500
tcaagcaatt ctctgcctca gcctcccaag tagctggaat tacaggcacc tgccatcaca   4560
cccagctagt ttttgtattt ttagtacata cagggtttca ccatcttggc caggctggtc   4620
ttgaactcct gacctcatga tccacctgcc tcggcctccc aaagtgctgg gattacaggc   4680
ttgagccacc acgcccagcc tggtgcaatg ttcttaaaat tactaatttc taaagtagca   4740
gctctgtgtc ttaggttttc ttgcaatcag tgaaattgct acagacccca tagtgatgca   4800
aatgtcaaca aacgttctat gcaagctatc tgctcatcaa caacttcctt gagcaacaga   4860
agtgcagtac ttaaatttcc attaaatatt tgttttttag ctcattactc caaagggtt    4920 tatttcaaat tctttaagta ttgccaaatg ataaaataca catagttttg gatttatgcc   4980
ctgcaaaaaa tgaccaaact attgtaacaa gagcctccag cctcctccat attatgctct   5040
gggtggggac tgctcagctt ccatgtgcca tggacatttc acaaccacca aatcataatt   5100
tcccatgtct cctgttgatc tgtcaaccgg cagctgtgca acttctgctc ttttatctac   5160
tctctccctt ggtgatttca tccagccttg tggcttaaaa tgccattcct atagttacaa   5220
ctcccagtta ggtctcatca tcccagatct tgtccctgaa taccacactt gtctacctaa   5280
```

-continued

```
ttgcctgctg gatgtcccca tgtgatgtcc aatttatatc tcaaccttaa caattccaaa      5340
gttgaactcc tgttcttccc cacccccac aaaaaaaact gcttcatctt cattctgtca       5400
ccttcatttc agctgatgac aacttcatac ttcccagtgt tcagtccaaa aaccttggca     5460
ttgtccgatt tctcctttct cccacccaga tccaactgaa aatcacggtg ttactacctc     5520
caaaacacct ctagagtttg atcacttgat cacttctcac cacctgccct gctactctcc     5580
ccagctgtca cccgccagca tgtttattta gtgtgtgtat tgtttatcaa cttcttcctc    5640
ctgctaggct tatacgcaca ctgagagcag ggattttgc ctgctgtatt cactgctttg      5700
tcctaaatac ctagaacagt gcctggcaca tagtacattc tcagtaaata cttgttcagc    5760
aaataaataa ctggaggaac cagtgaatta taccccggtg tgaataactc catgtgagtg     5820
acatgacaga atgtcagagc tagaagggcc tcttgaggac atcatgtctt ccttagatga    5880
ggaaagtcag gctcagagac atgaactgac tctcctgagg ttacacagcc aaatatgctc    5940
ttccaaggtt aattctctgc tacacaatag cttttgttgg tatctgtgag gctttgcggg    6000
gttgaaggaa tctcaggtgt cacccattaa taacaatcat gacagtgaca actaatgttt    6060
gccacgtgct tacaataagt caggaaccct gccaagcacc gggcgtatat taacctatcc    6120
aagctgggga agaatgttta ggctctgaag attgtctgga gccgcataaa tcccgcagtg    6180
taggcagctg ctcattctgc agatagtatt ctgtggatcc ctgagttggc tgtggccggt   6240
tttgccagca ggaggccacg aagccatgag cacaggatgg gatctacccc ttgtgggatc    6300
gcagagggct gggagatgca gtcctcccta tggaaagaga cagagctttc tatccctctc    6360
ccggtgaaac tcagcatggg agcatggagg cagtcagc tgcgtggcta tgaacatgag      6420
ctatggggtg catgcagacc aaggttcata gtgtacactg tacccaccag ctgtagctcc    6480
tccagcaagc gtgggaggcc agtcagctgc atggctgtga gcacggcctc tggggtccat   6540
gcagaccaag gttcctggcg tagcactgta accaccacct aggtcttctc cgacaagctg    6600
gttaacttct ctgagcctgg cttttgtcatt catcgcgtgg ggacaggtgc agcagaagag   6660
agcagacaga agcacaggat ctcaatcagg ctcttgaatc agactgcctg ggtttgaatc    6720
caggccctac tgaccagctg tgtgacctca gacaggcgac tccgggtctc agcactcaat    6780
tttctaattg gccaactgga gatgacaatg gcccctacct tgaatggctg ccaggaagat    6840
taaatgagaa aatacttaaa tgtgaaacac ttagaatggc gcctggaaca cagaccatta    6900
ataccatcta acagatgtta gttgttatcc ttatttatta ctcatgcttt cctttctctt   6960
ttttcttttc tctctctctc tctccttttt tttttttttt ttttgttgt tgttgttgtt     7020 gttgagacag ggtctcagtc cgtcggccca gactgaagtg cagtggcaca atcatagctc    7080
gctgcagcct cgaccttcca ggcttaaacg attctcccac ctcagcctct cgagttgctg    7140
ggaccacagg tatgcaccac catgcccagc taatttttgt attttttgta aagacaggat   7200
ttcaccatgt tgcccaggct ggtcttgaac tcctgggttc atctgatcca tctgccttgg    7260
cctcccaaag tactgagatt acaggtgtga accaccacac ccggccaata tcatgttttt   7320
tcaagcctgt aagaggaacc tcctagcact gtccccaccc cggccaccac actggtccca   7380
gccccaacag gtcagcttcc tttgctgttc ccgggcttcc ctcagctcta tctcaagcca    7440
tgacctctgc ctccatgtct gcagccccat gaggctgggg ctgctctgtc ctgcatatct   7500
ccagtgcctg gcaaggggct ggcaagaggt agaggctcat taaatgcctg ttaaaaccct    7560
aatagtaata ataataatgg tacagttgtt actaagacta atcactacct tccaaagtct    7620
ttcctctatg caaggcacgg agctaagcac cctgtagatc ctgacaacag ccctcccgtg    7680
```

```
atcccacaag agagacacga ttctctccaa tgtttaaaaa ggaaagtaaa agtcaatggt    7740
tctaagtagc tcacactgag tgattgtacc gggatttgga ctcaggcacc atcccttaaa    7800
ccagaggtca gcaaactttt cccctcagg aacagatggt aaatatcttc agctttgcaa    7860
gccagacagt ctctgttaca agcgctcgac tcccccttgt agcatgaaca cagctgtaga    7920
taatacgtcc aggaatgggt gtggctctgt gccaataaaa ctttattgtc caaaaacagg    7980
tgacaggttg gtttggctca taggctgtag tctgccactt cctgttttat tctaccttct    8040
gttcatttca ggtcactgtg catggcatca tcctggcccc ctctagagct ccaatcctcc    8100
aaccagagcc agctcttccc tcaaaatgct acggcctgtg acaatgctcc agaagctgg    8160 gacctgctgc acagagtgct gccaacattt atcatctcca tctgtttctt cggcctccta    8220
gggaaccttt ttgtcctgtt ggtcttcctc ctgccccggc ggcaactgaa cgtggcagaa    8280
atctacctgg ccaacctggc agcctctgat ctggtgtttg tcttgggctt gcccttctgg    8340
gcagagaata tctggaacca gtttaactgg cctttcggag ccctcctctg ccgtgtcatc    8400 aacgggtca tcaaggccaa tttgttcatc agcatcttcc tggtggtggc catcagccag    8460
gaccgctacc gcgtgctggt gcaccctatg gccagccgga ggcagcagcg gcggaggcag    8520
gcccgggtca cctgcgtgct catctgggtt gtgggggcc tcttgagcat ccccacattc    8580
ctgctgcgat ccatccaagc cgtcccagat ctgaacatca ccgcctgcat cctgctcctc    8640
ccccatgagg cctggcactt tgcaaggatt gtggagttaa atattctggg tttcctccta    8700 ccactgctg cgatcgtctt cttcaactac cacatcctgg cctccctgcg aacgcgggag    8760
gaggtcagca ggacaaggtg cggggccgc aaggatagca agaccacagc gctgatcctc    8820
acgctcgtgg ttgccttcct ggtctgctgg gccccttacc acttctttgc cttcctggaa    8880
ttcttattcc aggtgcaagc agtccgaggc tgcttttggg aggacttcat tgacctgggc    8940
ctgcaattgg ccaacttctt tgccttcact aacagctccc tgaatccagt aatttatgtc    9000
tttgtgggcc ggctcttcag gaccaaggtc tgggaacttt ataaacaatg caccccctaaa    9060 agtcttgctc caatatcttc atcccatagg aaagaaatct tccaactttt ctggcggaat    9120
taaaacagca ttgaaccaag aagcttggct ttcttatcaa ttctttgtga cataataaat    9180
gctattgtga taggctaaat gattactccc gtagattggg gggtacctaa tccctggact    9240
tgatgaatgt taccaaatta agggtcttga gatggggaga tgatcctgaa ttatccaagt    9300
gggccctata taatcacaag ggtccttata ggagggaggc aggaggctca gagtcaggag    9360
atgtgactat ggaagcagag gccagaggaa ttcaggacgg ccactacgag ccaaggattg    9420
caggcaccct ctagaggctg taaagggcaa ggaaatggct tctcccctgg agcctccaga    9480
aggaatgggt cctgccaact ccctgtcttc agcccaggga aacagattta ggatttctgg    9540
cctccagaac tgttagagga tacatttgtg ttttgttttg ctttgtttgc tttgctttgc    9600
tttgcttttt tgagatgggg tctcgctctg tcacccaggc tggagtgcac tggcacaatc    9660
acggctcact gcagcctcaa cttcccagac tcaagggatc ctcccacctc agcctcctgt    9720
agctgagact acaggtg                                                   9737
```

<210> SEQ ID NO 11
<211> LENGTH: 40851
<212> TYPE: DNA
<213> ORGANISM: Homo sapiens

<400> SEQUENCE: 11

```
actgggccca ctcttatctg ttctcttctg aaggaagggt tttaaggctt caaaaaaaaa      60
tgttttgaaa gtccctgccc tttccagctc ctaccgtctc agccctggga gtgtaaagtg     120
ctgcagatag ttagtaagtc tttgagcaaa actgagaaag ccagcctgag ccttgacatg     180
ggagaaacct ccgccataca tctccgaaga acggccgcg tgtctcaggg gagcgcaaac      240
acccgtaccc aggaaacagg acagcttctg ccactgtcgc ccttgggagc cgtacgtggc     300
atacaaagaa atcccaggac tccgcctgcc cacctggcca ccctctgttt acaccttccg     360
cgtaaacgcc cactgtttac atccaaaact cagacacaaa ataaccacct caagaagata     420
aataatgata agaaataaat gttacgcgag gcaaatttat tcacatgggg cttcccaggc     480
cactttgtgg tcagccggga gggacgtttt tgccgtccca cgactccaac gggcagccgg     540
gctacgcaaa catggaaatc ttccaagagc ctccctggcc cccagggctc agagggtggc     600
agagcggaga gcgaaggtgg ccgcagcctt cccggcccca cagccagcct ggctccagct     660
gggcaggagt gcagagctca gctggaggcg gaggggaag tgcccaggag gctgatgaca      720
tcactaccca gcccttgaaa gatgagctgt cccgccgcc actccagctc tggcttctgg      780
gctccgagga ggggtgggga cggtggggac ggtggggaca tcaggctgcc ccgcagtacc     840
agggagcgac tgaagtgccc atgccgcttg ctccggagaa ggtgggtgcc gggcagggc      900
tgctccagcc gcctcacctc tgctgggagg acaaactgtc ccagcacaga gggagggagg     960
gagggcaggc agcggggaga agtttccctg tggtcgtggg gagttgggaa aagttccctt    1020
ccttccggag gggaggtctg acaggcgatg gggagaaggg ttcccagcag gaggaatcgc    1080
cctgtttgtc tgttgtaggt ttctcttctc tgaatcaagg tgacagacag gcttgtgtgt    1140
gtccagtgtg tgagggattt cgtgattgga ttttcacata ctttgagtgg acaccttgga    1200
gtaaggcagc gaggtgtgtg tggtgcagca gggacgggtg ctgggtggag gctccagaac    1260
ctggcttttc acccacagct gtgccactcc ttggccctgt gtgaccctgg acaagctatt    1320
caacctctct gagcctcagt ttctctgtct gcaaagcagc cagctcgctg gctccctggg    1380
ggtggcaggg ttaaatcaga agcaggcggg ggtgggggg tttgtgaatg ttggctgatg     1440
cgcctccagg aggcaggtgg tagtgactac ctcagatggg cttagagacc ctcttcccac    1500
ggtcctggct gaccagggca gggggatagg atggtgcagg ggttccaagc accggctttg    1560
catccggccc aggttgcagc tccagccctg ctctcaccct gtgggtgacg tttttgggcg    1620
agttattttg tcctgtctcc tgagctataa agaagacctg gaagttcctc tttatgcaaa    1680
gatagaggta ggctcttgcc tgtgaagcac cacgtatgtc ataggcacta aataaatggc    1740
agccgtgatt cgagttgctg agagtaggtc gtttccgcag cctgggtgga ggtgaacagc    1800
aggtgttgct gttccaggca ggtcagaatg tgcctcactg agtcacaggc cgcctgtggc    1860
tccccagcct acaggaagtg ggagccctgg cctgggtgtg gggtgatggg ggcctccctg    1920
gccaaccccg cccctaattc catttctgag ttggagaagg gcttaggtgg tgggggaaca    1980
ggtaagcaac cccagaggac attgcaaaga ggccctgccc gaggttctct ggagaaaaaa    2040
ctgtgctgcg tccttcgggc cctggcagca gcaagagaca ttccacagtt gtgagcccca    2100
caagcttgga ggaagcattt gctgtttccc ctgcttgggg tgagagcagg gacagccaa     2160
gagaaggcgt cttttggatga aaaagaggaa gcatgcgtgc tgtccccaca ggcagcaccc    2220
caggcctcat cccagctctc cctgcaaccc tgcactccaa gcctctcact gcactgatga    2280
ggaaactgag tctcagaggg ggaacatgac ctcagccagc ccttcgctca gtgtccaggg    2340
aaatgcctca atctctttgg gattccctcc cttgcaaacg gggaggttcc catggttggg    2400
```

```
cctgcatgat ggatctgagg actttgaaag tggtatttgc ctgccggtgg gacccaacct    2460
ggaaatatta ggttggtgca aaagtcatct cggttcttgc cattagaagt aatgccaaaa    2520
accgcaatga cttttgcacc aaccgaatag ctgtgccacg tggttttttgc taacacagtg   2580 actggctcag taacaagttt ggtggctcca gaggtaacat tagggcggcc tcctcacctg    2640
tgctgcttgt ggtcagggag gggcccacct gggcgcggtg gggggagccc tgcagatttg    2700
cccagtgtca tagcctgttt gagctgctat aagaaatact ttagactggg taatttatca    2760
aaaaacagac atttattgct ctcggtgctg gaggctggga agcccgagat caaggcactg    2820
gcagattggg tgtctggtga ggacctagtc gtcatagatg gcaccttcta tgcatcctca    2880
tatggtggaa gggtgaacac gctctcccag gcctccttta agaccacca atcccattca     2940 caaggagggg gacctcatga tctaatctcc ccccagaagt ctcaccttt aatatcacca     3000 gcttggagat taagtctcaa caggtgaatt ttggagggac acaggcattt ggatcatagc    3060
accgggggac tctggttttc agaatgaaag taggggcctt gtctatccgc tcaagctgcc    3120
tcctctgcac tgaaaacgat gcctagccca acatggatgg atcagtgttt gctgaaatgc    3180
tgaatggtta aatgaataaa taaatattgc tcatatagca ggcaataaaa aagcatacag    3240
aacctatcac taagtgaatg aagctactct gaaaaggcat atgctgtatg atttcaacta    3300
tatgtgacat tctggaaaaa ggcaaaacta tgaagacagt aaaaaataaa aaaaatcagt    3360
ggttgccagg aattagggga gggaggagag aatgggagga gcccagagac ttttagggca    3420
gtgaaacttc tgtatgacac tgtaatggta gaggcatgtc attgtgcgtt tgtgcaaacc    3480
cacagaatgt ccatcaccaa gagtgaaccc tgatgaaaac tatggacttt gggtgatgat    3540
gatgtgtcaa cgcaggttca tcaattacaa caaattgact gctcttgtgg gggatgtcag    3600
taacggggga ggctacgtat gtgtaggcac agggatata tggtaagtct ccgtactttc     3660
tgctcaattt tgctgtgaat ctaaaactgc tcttttaaaaa aaaaaggca cacagagcag    3720 atctgcatgt tgttttgagg attcagaagg cacttaggac aattacggta cctcagggtc    3780
atgagtcaaa caatcagacc tgccaagact tgacacccca aatgcatcac ttctgacatc    3840
cattgggtcc aggaatcccc tgcctcatga atatccatct tagtgtgcat gcctccaaga    3900
atggggagct cactactttg cgaggcagcg cattccatct taggagagtt ctactgttta    3960
aaagctcttc ctccaactgc ccccactgag caatgggtcc actttcattt ccttggggtt    4020
tgtaccattc tagtcctatt gcttctctct gagctaaata tccacagcta ctaaatctgc    4080 ccccttgaa aagtgttaaa tcctcaattc ctcctctgag ctcctctggt tttcctgggg     4140
acctaaggct ctgcttcccc aaaacaccca ctccagggtt gttttctaga caaacgtaa     4200 ggcatgaagt atttctttga ctctttcatc acagtgggtt ctggaagatt ctggaggctg    4260
gaaacatatg tgcctccccc tccccacaca cattccaaaa aagtcatcac agcagaaagc    4320
acggtggaac aaacagctct cggttcgaat tcaccgtcac ttactggcca ggaaagttat    4380
ctgagcctca gtttcttctc ctgtacaatg gggagcatca ttcctatttt tgaggaccac    4440
taggaggctt acctctgttt gtgctgatgt agtgaaaggg gatgtcaggc acactgcagg    4500
agctcaggta ccagacggac tgtctatgga ggcaggagtg agggcctggg gcggtcacag    4560
aggttgcatt tgctttgcag taaggccatg gccgcttaag ggtgtccaga aaaagccct    4620 gtccgacatg cacacactcc tgtgtccagg caatgagcct gtgggcactg acagcaagag    4680
tccttctcac gcttctcttc agggctcaaa ctttagattt actccggcct gtcccatccc    4740
```

```
attcactgcc aaccnctctg agcctctctg atctgtgcca ccggtgaagg gcagtcgtgg    4800
ggcacagaga agtggcccag ctgagtgaca tctggaaatg agcagtgcct gaggggacgc    4860
ccgtggggtg ttgtgacctg tacagtgcca ggctccagca cagccccgtc gcttctgtgg    4920
ttcttatcat ggtcatgagg tcgcttctcc tcttccctgc gggttttccta agtggtcaca    4980
ctccagtggc agggtggtct gccggagaaa gaccaaaatt tgtcatactt tagaatcacc    5040
tggagactgg tcacccacgc aggtgcgggg gtcctgctct ggggactgtg atttgaagtc    5100
tgggtactat tcactgaaat gacagactgc ggcaaatctc aatcaatcaa ggttcatcga    5160
gttgataaac ttcaattgac atttatcgag agtttgaggg tgcacctggg aaaaacatga    5220
gccacagaaa atgtgtgtgg cctatgctct ccgaagagtc atgagactta gtgttgtaaa    5280
tcaaagagaa actgactgaa gcaggtctca attattttg aagtttattt tgccaagatt    5340
aaggatgcac ccaggaaaga gggacacgaa atcacaggaa acatctctgg cccatgcttc    5400
tttcaaagaa gggtcttcac tattcaaagg gaaaaaagca ggcagtaggg gaaagaagga    5460
aaaatcgggg gaaggtggcc aaaagaggca agcagttgca ccccttttgag cctttccatt    5520
aacttcactg aatgcacatt tttcatgtga aagaagcagg tggaggaatc atcaattccg    5580
cattcacctg gtgctcagtc aatctgcatt tttatataag ataaaataat catagggctg    5640
ggcacggtag ctcacaactg taatcccagc agcttgggag gccaagttgt gtggatcacc    5700
tgaggtcaag agttcgagac cagcctgtcc aacatggtga aaccctgtct ctactaaaaa    5760
tacaaaaact agccaggcac ggtggtgcat gcctgtagtc ctagctactt gggaagctga    5820
ggcaggagaa tcatttgaac tcaggaggca gaggttgcag ggagctgaga tcacaccact    5880
gcactccagg ctgggtgaca gagcaagact ctatctcaaa ataataataa taataataat    5940
catcatcatc atcatcatag catataggaa gctgtcagct atgcactcgt tcaggtgag     6000
cagagggatg actttgggtt ctatccttg ttccatacct gtgaagctaa gctgttaatt    6060
tatatcatga gggtgaaata caacagagct gcttgaaggc aaagatcctg ggcccacaa     6120
ggaattcac tgtgagcaaa atgtgaggga agtaaatagt tatccattta gacacaaaac     6180
gggaggcggg ttgcatgacc cagctcccag ctagactttt ccttttggct tagtgcgttt    6240
ggggtctggg gatttaattt ttattttct ttcacagtat ttacacatgt ccttgaagtg    6300
gagaaagcat gtaggaagag gaggttaggc agaaggaggc ctgatctcat cttgcctttg    6360
tcttgctttt atgctgtacc tggggagatc agcaccatca gcgtgactct aacagacttg    6420
agtgtgagga gctaggcttg gattgcagac ctcaagttac aattgatgtg tccttgttt     6480
gtggtaagat ccacatcttg aaaggtttca cccagcaaag aacaatttgt gggggcagtc    6540
atggggagat atccgaggcc ttttcctttc tgtgggggtc tggctaatgt ctaaggttgt    6600
ggagtaacag ctgtcattag gaataaggat gacaatgttg gctgactcag tctccaggct    6660
taactttccc tttggcataa agagtttggg ggtcccaaga tttctgtttt cctttacagt    6720
actcaaggac ttgctaatat ctcagggat ttcagccaca ctttgaaaca agctaccta     6780
gcaaatggtc tgtcctggac ccaaaagcca ctctcctcag gcccttcctc ctagtcccac    6840
cagccaaaaa acttggggac cccaaacctg ttcttcactc tctggcacct gtgctcatgt    6900
gcctgctgcc tcaggaaagg acagaaaccc tccccgatcc aagttattag caaactgccc    6960
atctccacaa aaatttaaat ggacagattg ttaaatgcac acagctcaca gccagctcct    7020
ttcaaggtag atttgggccc aaacatttcg ggaagcatca ggctgtgccc cgccatccct    7080
accaaacagg aatcctctcg agggaaaaga ctgggccttt ccctcagccc ctagcaccca    7140
```

```
ctcatgcttg gcacctgctg tgctctaaga gtgcaggggt cactccctga ccacagaggg    7200
aggctctctg gggttctccc ggagcctcgg agattgcacc ttgtgcatgc gctgctgcac    7260
ctggggtaca tcaccccac tctggagccc actggccggt tagcaaagtg agaggtgaga    7320
gaaggacctc ttggtcttct ttgaacagaa agatccagaa agcaatggct agaacacaag    7380
aacaggtcag gggaggcagg agagggtctg cacacctgct acaggtgtgc tcacacgtgg    7440
gccagggcct gcagatgagg gatctgtgct gatcatttgt gatagccaaa agtagtgaaa    7500
acctgggggg actcctcaaa tgaactgtag cacattgggg agatggactc tgtgaagatg    7560
attcctctct ccacccactt cccttctccc tcctcctccc gctcctcctt tttcggaagc    7620
caggcacagg gattgaatcc caccccattc ctcccctgct gtgtgaccta gggcaagaga    7680
tgtggtctct gggatccttc ggttccttca gctataaata gtagtagaat tgcaaactac    7740
ctacgaaaac tgggaactcc ctgcgaaggc cggtgcatta cagggcagtc ctactctgaa    7800
atactgtgag gctattgaaa agcaaggtgg gtcgacagat tgttaaatgc aaagaggtga    7860
ggacacagcc ggcggtgcat ttagggtgct tctgcaggcg tccttataca tggatatgtg    7920
cacatctgct cctgaaagct cagaagatgt ctggaaagca acaggagaca ccagtgagcc    7980
tggctgtctc ttgaggcaac aggcagggac agaatctgga gggagaccta ccctcactg     8040 tattcttttt cgcactctga aatgttacca tgaggatgca tatctctttg caaaaattta    8100
aatataaaaa gcaaaacaaa cttgaataga aataaactac ttgaaaattt tagaaaacac    8160
tgttacatca aagagacaga tcatcaaaac tgaaattata gatatttgag aaacaactaa    8220
ctataagaac actgcttacc aaacttatgg gatgcagcca aagccatagt caggggatga    8280
gtcatgcctt taaattttta aattattaaa ccaaaaagat tgcaaaaaaa aactgttcaa    8340
ttcaataaac tagataataa tgatccaaaa aagtagaaga aagaaaagaa ttacaaaaac    8400
aaaatgacaa gttagaaagg taaaaagcat taatgtcagt aggccatcta aggatggctc    8460
tttgaagagc agacaggaga agggcaatcc caggaagtgc tatgtgctat gcagagaatt    8520
agaataagtt gatggcagag atcagtgggt ggcggctcac ttgggtggta aagagtagcc    8580
tgcagccaaa gttgggcaca gcagtgcagt cttcactggg ggaatgcctg ggaaacaaga    8640
tttgcctggg taggagtttc catcagcacc cccagaaagg tctcctttct accctggccc    8700
ccagttcttt gatgggtttt gctgatgctc ctgtgtctct gaacagcagg cgcctcacct    8760
atagaaaggt aggatagcag gagttaacgc ccccctccccc attccatggc ccctgcctgg    8820
gattctacca tctctgcttc atatgctttta taggagttcg gtctgagccc acaacccaaa    8880
caggctcaca gatgtgctag ctatttcgcc accagtattt ttttaatagt caatatttag    8940
aaattggcac caactggccc gattgttcaa cagtcctggg ttaggttact aggccaatta    9000
cttgctgagt aacccaggac aggtcactga cctctccgaa cctctccttt tcacctgtg     9060 tgataaagac tactgctgtg ccaacacaat aggactgtgt atgaaagtac ccagactgtg    9120
cctagactca ggaagctggt ttattccttc ctcccctaac cacttactga gagactgctc    9180
agggctcccc tcagctcaga gatctttccc cacaaggagc tgagagcctg gtgggagaga    9240
caggcagaga cccaagtggt tctaacacag ctctctgaat ctgtaacccc aagtcccatc    9300
cccagaggac actgggacag tcacactgat ggtttgtccc taagcctcca gcatcaggag    9360
ccatgtggca ggatctccac tcttcttctt cctgggcctc tgtctggacc gacccaaaca    9420
cacacacaca cacacacaca cacacacaca cacacgtgta cacacacaag ttgcttcttt    9480
```

```
gctgcctgca tgtcctcaca ccagcttatg acacacctac aatgtttgat gtgtcattgt    9540
gggcaggttt caagttggag gacctagacc taggtaaagt agagggtctc cctaagtaag    9600
ggagggtgca cagtggagag aaagggtagg ggagactgcc cagtgccatt gacatatgcc    9660
tgagccccag ggcacccttg gccccccaaa acaatcacaa gtatcccccc cgacaaacct    9720
gccaagtagg cattgtgtct ccacttgaca gttgaggaaa tggtccctag aggggagaca    9780
gagctagcta gagactgggc tggccctgga gcctggcctg ggtcttccca tcgcatcctg    9840
cctccctaca taagcaaagg tcgagaggtg ggaactccca aagatgctca ggcagggcca    9900
ggggagacca gtggggcagg gaggggacag gaggggaagg aggagctggg gctggagaga    9960
tgggtaggag catgagtccc ttgcctgggc ctccccatgg tgggcggtga tccaaaagcc   10020
ccagtcagag ccctctgccc tgtgacgggg gcaccctgca tgtcccctca ctccctgccc   10080
tccagtcccc gccagtcctc atgttttcca tgaggatgag tacagccgca gggactttcc   10140
ctgcaagtgg tctgggccat atcttccggg agtctgtttg gactgtggtg tctgtggctg   10200
agggggtgga ggtgagggca cccaggccca tcacttgaca gaacaatctg tggatttggg   10260
ggaaagagga ggcgactgtc attcctgaga ggacgggga accaacagga aggattcctg    10320
agtgccaggg atgaccacac tggatcctca caacagccct cctgccgggg acaatgctcc   10380
ttatcccaca gcggggacc tgggctctga caggaggcca cacacttaca gtccctccct    10440
tagtgaccgg cagagctggg atttgaacac ccctggtgag actccctcgt ccagacccct   10500
tcgttgtaca gcaggtttgc ctcacatgcc agagtcgggg tggcctcagg gcacagccag   10560
gagatgtccc caaatcccga aatgtggttt gagtcccagt ccctcatctc tccagcctcc   10620
aagccctcac ctatgcaatg gtgccttgcc cggctcacag gttatgaaaa ggggtgagac   10680
gagacagtgt cccctaaata catctgacag cacttttgaa tggaaagag aaaaagaaaa    10740 tactataagc atccagattg actggaggtt ggggagttgg tgggggcggg gacaggcaat   10800
ccataaagca agaaaaatca ggctgggttc aggcttttct gcagcagcga atgcatcaga   10860
gctgccaggg gggcagctgt agacctaaga gagttccttt aagcacaaat tggctgatta   10920
tcttttttac gtaaataaac ccataattca ttccaaacac ttggcttatt taaatatttt   10980
tattgccaaa ggaatatatg ttcttcacag aaaacttgga taccatgaca aacagtaaag   11040
aaaacccaaa agcaacctat gatcccatgc tcaaagacaa ccagcgccag taataatttg   11100
gtattttgcc ttctcaactt tgaactttg ttgtatgtac aatttggtta cccagctttt    11160
tgttccccta acatgttatc agaaacattc tctcattttt ggtgaactct tagaagcatc   11220 ctttttttcat gtctgcttga catttgttga atggatataa gatcatgtat ttaaccaact   11280
gcctggtcct aaacatttag gttgtttcct gtgaccctc ttctgcatga tgaggaacat    11340
ctctgtgcat aaagcttttc ctgtcctttt gattattttc aaaaatgcca aacaaaaaa    11400 aaagggaggg ggttgaaggt tctgggtttt cttcactgaa ttatccaaat attaaatgat   11460
ctagagacag gtttgggagc cactaaaccc tctcctcctg tctgaccta ttcagagaag    11520 acattggaag ctgccatctg ctttcctctc acagtctgta agtggctcat taaatacttg   11580
caaactagat tatttttatg ttgtcttggc tacaggagtt tctgcaggaa tcagaaacag   11640
gaagaaaagg caggtccttg gagacagagg agctggcatc tcatcagatg caatttctta   11700
ttaatagtca tccctaacat tgattcggca tctactaata atcaatccct tcttacagat   11760
aaggaaactg agtagcaata atctatccca tcttacagat aaggaaactg agactcagag   11820
aggttaaggg cactgcagta agcgcagaca cagagctatg actcccgttc tccctgtgtc   11880
```

```
agcccctgcg cagtgcgagt gggaggtgag ccactgttgc gtgccctctg ccagacacag   11940
gcctgcaggt cagactcaca ggagccaagc agagcatctg ggaggatttt gtttctggct   12000
ccaaaaatga ataccaagg aaagtaggca agctcatgca tgtcagaatc ctcaatctca   12060
gctcaggaag taggaatttt ccacctttgt tagcagcaga gatgacaaac cccagggccc   12120
cacatatagc ctgtgcctta gtcactgcct cgggccaggt tgcaagaccc ctcctaccaa   12180
ctgagctaca aatcacagtt cctggagggt gggcctttat ataacaggga acagaactct   12240
tctgtacctc ccacctcccc gcaagaagta ggccaggcat ggtagctcat gcctgtaaat   12300
gaagcatttt ggtagaccaa ggtaggaggg tcacttgagg ccaggagttc gagacaagcc   12360
tgggcaagat cccatcttta aaaaaaaatt taaaaattag tgagctgtgg tggcaggagc   12420
tgtggtccca gctgcttgga aggatgaggg gggaggatcg cttgaacccg gtgggtagag   12480
gctatggtga gttataattg taccactgca ctccagcctg ggcaacagag caagatcctg   12540
tttcaacaaa agaaaaagaa gagagaagag gaagaaagaa ggaggagaag aggaagaaga   12600
aggaggagga ggaggaagga ggaggaagga ggaggaagag gaaggaggag gaggaaggag   12660
gaggaggagg aaggaggagg aggaggagga aggaggagga ggaggaggag gaggaagtag   12720
gagaagaaga aggaggagga ggaggaggag atcctacagc actgtttgga agattatggg   12780
aaaattaggc ccacacatct gatatacaat cggcacatcc tacaaatgta aaatgtgtgt   12840
cttgaaccag aaagcccaag gagtgagggg ctgtggcatt gagtggggta gctatacata   12900
gccctagggc ttaaatctat agaatttaag taatcctggt ccaaattcac cagaaacatt   12960
gcctagactt tacttgaata cctttagtga cagggaacta actactacca aaggcaacta   13020
actcagctca gcaaacattc agtgatagct gcgcttcccc aggaccagag attcagataa   13080
gcaaacaccc tgttctgtgc tcaagggact gatggtgtgt gacaatcgag atagtgtgaa   13140
gaaaaaggac agcatatgtg tgtctctgtg catgcatgtg caaacactga cactgcagta   13200
tgtattcaga ggaagtcact acaatggtga ggcccacctg gcaccagaat gaacagattt   13260
aagaaagcta gtcaccgcag acggtcacag ctggaaggat tttacaaaat aatctatctt   13320
atcatcctcc tttgccctag agatggggaa actgaggccc aaagagtgaa agccacctgc   13380
tcaaaggcat attgttgagt ctaataataa aaataaccat agcaatagca acactgaggg   13440
cagctgtccc agatggacgc tggctccatg ccagcccctg ggctaggcgt ctggtggcac   13500
tacctcattt cactgccata acaactgggt ccccatctt gcagatgagg aagcccaggt   13560
tcagagaggt gaagtggggg gctgggggtc tatcccagac cttgttgtca cctcctcact   13620
ctcccagtag cgccagccag agcacctgtc ttgggagccc cgaggcaggg acaggctatg   13680
catccaggaa gccccaggc tctaaggagg cggccctata actgctggat gaccaaaaat   13740
caggcagcga tccctaagtc ccttctgagc cccaggctcc agactcctcc aaccaggtct   13800
gccttacgct tttgaccaca atcaacccgg ctctttctcg gttcttttca tctctctggt   13860
ggttttgtat gcagagtcac ccaggtcccc acttacgagc ctgtgagatg ggataaatca   13920
cttccctttg ctgagcctca gttccttcac ctgtaaatgg gcataacaag ttcctccagg   13980
acaatcgtga ggctcaggga aaggactgtc gtgcaaaccc accatggcat gagctgtcga   14040
gtgcagtgcc cgctgccact aaggaatgag tgccactctg ggattgtgga aagtgcagac   14100
gggcagggtt gagatgctcg tgcatgactt tggacaggtc acctcccctct cagaggttta   14160 gtttccttac ttgttaagct tggactaaaa atatctaaat ggtgagattt ttccaacttc   14220
```

```
tttggctcta gcatgtctgt ggtccttgat ggtttacaaa gcgcttttgc acttgagacc    14280
cctaagtgct aattctacca catcccatc cacttcatag tgggatgacc ttagccaagg     14340
ctcttcacct aaacctccat aagcccctcg ctggaatttg agcctgtttt gctttttaa    14400 agtgagggca atgctactgg ccccacccat cttacaggac aagggaagcc caaggacatg    14460
agagctttct gagctgcatc ccaggccctg ctctgccact gactcgctga ggctgggttt    14520
ccccatctgc aaaataagga cataaaaacc catctagagc tgggcatggt ggctcatgcc    14580
tgtaatccca gcactttggg agtccagggc aggcagatca cttgaggtca agagttcgag    14640
accagcctgg ccaacatggt gaaacccat ctctactaaa aatacaaaat attagccagg     14700
tgtggtagct catgcctgta atcccagcta ctaggaaggc tgaggcagga taattgcttg    14760
aacccagggg acggaggttg cagtgagcca agatcacgcc actgcactcc agtctgggtg    14820
acagagcgag accccatttc aaaaaaaaca aacaaacgaa ccaaaacaaa taaaaaccca    14880
tctagagtgt tgtgggatt aaatgagtta atatctgtga agtgctttga acagagctgg     14940
cacggccggg cacggtggct cacgcctata atcacacgcg tttgggaggc caaggcaggg    15000
atcacttgag cctaggagtt caagaccagc ctgaccaaca tggcaagacc ctgtctctac    15060
taaaaataca aaaattagca gggcgtggta gcatgctgct gtaatcccag ctactcagaa    15120
ggctgaggca ggagaatcgc ttgaacccag gaggcggaag atgcagtgag ccaagattgc    15180
gccattgcac tccagcctag gtgacagagc gagactctgc ctcaaaaaac aagaaccaaa    15240
aaccccttaa gagaaatggg gttttctctt atgagaaaaa taaatatctc cggtgtttcc    15300
tctgacttgc ccagggctgc acagctcaca ggggaggggt ggggaccggg acctggcact    15360
tggctcctgc tgctctgccc tatgcccttg gggacttctg gacaagggtg ggcttctctg    15420
ggctgacaga ggagacagag gcaatggtgt gctggtaaat ggttaacaac tggctctctg    15480
gaaaaaaatg ccctaactgt agcaaaaaaa aaaagagac tagaactggc acattgcaga     15540 tgataggc atttgctgtc actatcagca tcagcatcat tacttgtcct ttcaacaaat      15600
atttcctgag cccctgtcgt aggccaggcc cagtgctaag aggtggggac acagtggagg    15660
gaagacagaa agttaagtgt gctgtttcca taaagtgtgc tgacagccat ataggagcac    15720
tggggctggg gtgtctctac ggtgcctggg agggtctcct agagaaggtg acatcaagca    15780
ggttctgaag gatgagtagg agttggaagg agttggaaga gctcctgccc tttgtggagc    15840
aggagaggga ggtggtccag ggacctttct ggccgaccaa gcctagagcc aattgcagtg    15900
agccattgtg acattggact tgaaactggt cactgcgaga gtatttatac catagaaatt    15960
tgcaaatgct acggttaggg catttttttc cagaaagccc gttgttaacc atttaccagc    16020
accccactac ctctgtctcc tctgtcagcc caggaagcg caccettgtc cagaagtccc     16080 caagggcata gggcagagca gcaggagccc aagtaccagg tcccagcccc cacccctccc    16140
ctgagagttg tgtggtcctg ggcaagtcag aggaaatgcc gggggtattt attttaaaaa    16200
gtgtctatca ggactctaca ttatgccagg ggtctcaaag gtgaaagagg catgagtttg    16260
tccctcaagc agctcaggag gagctggagg aggtttccta ggcacgagct tatccacacc    16320 atgcacata gaccctgaag tgtttttaaat caattacaaa aagcaaaaat acaaggaagc    16380
tgacagatct ttactttggg agaagtggag gcttgggaac aaatgagatc atcaaggtct    16440
ttttgtccgt tttctaagga gttggggtca ttggctgaga tcctgcagat ctggaggtac    16500
caacatgaga ctccgagggc cacctcctct gcccctccct ccccacccc tttaaggccc     16560 tctctggaat ccatcccttt tcctccatct ccccagacct ggctgaggcc tccgttgtgc    16620
```

```
ctctggtctg gtgcctcagc cccctcgctt cctgcttcca gattttgcca actgcccccc    16680
acctttgacc atgtccaggc atcctggctc aaaagccaag atgagatcta tacttgagag    16740
cgtatatgag agggatgcaa ctgaggctac ctggagtgcg tggacacagc catggcctca    16800
ggtcatcatc tcccccacga agcctccac acctcctgtc cccaacttgg cacacttcc      16860 caccacctgg gagaccctg agggcaggca ccatctgtcc ttcaccacta tatcccccta     16920
taaagagaga taatgcagtg aggtgccggg gttcaaatcc caactccacc catcaccagc    16980
tgtgtgactc tggacaagcc acctctgtgt gactctggac aagtcacctc actgctctat    17040
tcctccaatt tttataaaat tgggatagta ccagtgcctg catctaaaat aggtgtggat    17100
tacatgaatt atttcatgga aagtgcttag aacattgctt ggcattcata gtaagcctcc    17160
aaaaactgaa gctattatta ttccctggtt gctggcccag actaagcact cataaatttg    17220
ttgaatgaat gcaatgtaaa cagggaaatg ctctgtaaat gctggtgcaa gctcatcagc    17280
ttcgttgtcg tcatcagcat tgtcctgatg ctattcatgg tgggtgtcct gtctggagcc    17340
ctgctggctg tagaccacca atgtgggcac agtcctagcc cctcgctcaa gtagggtatg    17400
cgaggactca ggagacgtca acagacattc acagtattta cactgggacc ttggaaccag    17460
tgtggttgag tagacacccg gaggacagag ttctgagttt atttgggagg ggttgccggg    17520
gagagtcagc tgtctggaaa ggcttcctgg aggaggaaga tttgctagag gtgcttgagt    17580
ggttggtgca aggggggcttg tggggaacca gagcgtcctg gtgtttagag cagcaaggaa    17640
gaggctgggt aaggacaaag gacattggga cagacagaaa gcctgactct agaaagaagg    17700
ggccaaggtc actggagagg agagagagga aggattaagg acgattgagt gggtcatagg    17760
ggttgagggc tctgtgtagg gaaaacagtt tcccactcaa tcctttcgat gccactgtga    17820
ttaaatgtgt gggtttattt cctcagaaat tgtcttacaa ttccgttcag ttctgacatt    17880
atctgcccgg aggcagcaca ggataagagc tcagtcccac aagactgccg ccacttcaga    17940
acccatcgca agtctcaagt ggcctgcact tctgaccaac cagctgtaag gcagggttcc    18000
cacaaccccc tccacgggtt cagtaatttg ctaggatggc tcacagcatc agggaaacat    18060
ttacttacat tactgactta aataaaaga caccactcag ccacagccag gtggaagaga     18120
ggcacagacc cacacgtggg gcaggggcct ggagcttcgg tgctgtctct ggggcacca    18180 ccagctcagc acttccctgc gttcaccaac tcggaagctc tcccaatcct gtcttttagg   18240
gattttgatg gaggcttcat catataggca tgatggataa taaattcaat ctccagcccc   18300
tcttcccttc ctggaggatg tggggtgaaa gttccaagct ttgtatcatg gcctggtcat   18360
tctgatgaca gcccccatcc tgagcctatc cagccaccac caagagccac ctcattagaa   18420
caaaagatgt gcctatcatc tagaaatgtc aaggagtta ggagctccgt gtcaggaact    18480
ggtgtcaaag accaaatatg tatttcctaa tatatcacga tatcacaggt tgtgagaaga   18540
atgcaatcaa tggtcaaact ccagagctgc acactctcca atatggcagt gaccagccac   18600
atgcagtcac caagcacttg aaaggtggct gcttcaaact ggtatgctaa gtgtaaatac    18660
acactagatt ttgaagagtt agcaggaaaa aataataata taaataact caatgacttt     18720 ttgtattgat tacatattaa aataatgttt tggatatatt tgattatatc tcatatataa   18780
ccaaaattga tttcacctgt gtcttttac ttttttttaat gtggctacta gaaaatttga    18840
agttacttct gtggctaact ttatagttct attggacatc accgaccgct ctaggctatg   18900
gaaaattctg tagaacaaac aactggaagt tggaagaaaa gacagtaaga aatagcaagg   18960
```

```
aagggtgtgc tgttgggagt tgcttggagg ttggcggcac agggctgaag gctagcaaac    19020
cgagcgatca tgtcacacaa acaaattcac tattcggaca gatacgacga cgaggagttt    19080
gagtatcgac atgtcatgct gcccaaggac atagccaagc tggtccctaa aacccatttg    19140
atgtctgaat ctgaatggag gaatcttggc gttcagcaga gtcagggatg ggtccataat    19200
atgatccatg aatcagaacc tcacatcttg ctgttccggc gcccaccacc caagaagcca    19260
aagaaatgaa gctggcgagc tacttttcag actcaagctt tacacagctg tccttacttc    19320
ctaacatctt tctgataaca ttattatgtt gccttcttgt ttctcacttt gatatttaaa    19380
agatgttcaa tacactgttt gaatgtgctg gtaactgctt tgcttcttga gtagagccac    19440
caccaccata gcccagccag atgagtgctc tgtggaccca cagcctcagc tgagtgtgac    19500
cctaggaggc acaatgtgct ctgtatccag aacacacttg gcagatggag gaagcatctg    19560
agtttgagac catggctgtt acagggatca tgtcaacttg ctgttttttgt ttttttcctgc    19620 ctggtgttgt atgtaaggtc acttgtggat ttatgtttca gcgtactgga aactttccat    19680
tttattcaag aaatctgttc atgttaaaag ccttgattaa caaggaagtt tttataatct    19740
aaaaaaaaaa aagaaatagc agggaaggct gtaggtgaaa agaaacttaa gagacctatc    19800
aaacaaccca atgtgtaaag tcatttgcat tctgattcaa gaaaaccagc tgtgaagaaa    19860
gtagcgtgaa attcatatga ttgaaagttg taatacttcc tggatagttg atgccattta    19920
ggaattattg tcagtttctt cgagatgtga taatggttgt ctagttatgc tttctgaaat    19980
aagagtcctt agcttttaga gaagaatagt gaaatattta cagatgaaat gacagacatg    20040
caggatttac tgcaaatatt acaggagggg taaggtaggt ttgggcatag agaaaaagat    20100
tggctgcgag ttggtaatta ctgaagctgg gtgaagtatg tggagtttca ttatgctagt    20160
ctatctactt gtgggtatat tccaaatttt ccataataaa aagttaaaaa gcaaaaaaaa    20220
gaaccatcat ctccacctga ggttctggcc cagactgctt atgttcaaat ctcaactcta    20280
gtcttgctag ctgtgcctct gtttgctcgt ctgcaaaatg gggatgataa tattagtccc    20340
tacattgcag gggtttctct gtaatgtgct taaaaatatg gaaacaatat aaatgaaatg    20400
aagatatgtt gcaggcactt tgcacattgt cacggtgctc ccagtgcctt gttccaggga    20460
ggttatcctt atttaccaag aggttaagtc acctgcccta ggtcttccag tcagtggagg    20520
caaagccaag acatgtcccg agttcatctg acttctgagt tcaggcatga cctgaatgtt    20580
cttgcctcgg gctcagggct caacatttcc tgtcttctct gcttctccag tcctgagaga    20640
ttctgggccc gtttccctgc agatcagctc taaggaacat gcttctctcc tgctcctttc    20700
tagaaaaggc gtaacattgg cagaaccagg aactctggaa ttctgaaggt tgactccctc    20760
aattccaagg ggctccacct cctgagcgga attggataga agacaaaggt cacatggcta    20820
gggtgaggct ttgagatggg cgagactgtg agcaggactg acaggtcagg gccaggaccc    20880
aggatcttca gaagccacag ggagcaaggc agggagcagc ctcctttgtg ccacacccag    20940 tgaagggaa cttgctaaga cagatttgtt cctcccatct ccagaagagc cgttggatgc    21000
caatgggtga ggagctgaac ctctgcagac tcagtgtgct gatcccattg cctctgcttg    21060
catgcctctc aggatgggga gttcactgca tccccctctt taaagacatt acggttgtac    21120
aaaggtctcc agaatcatct gttacatccc ctcattctcc caatgaggaa attaaagctc    21180
agagatgccg aggcatttac ccaagggcac acctggtcct gggcctacga cccttagaca    21240
atattccttc cacctctttg ctatagagtc tcagactagg gatcttggct ggctgagaaa    21300
tcagggaagg cttcttagag gaggtgagat tggaggtggc ccttgtaggg tggcactaag    21360
```

```
atgtcgcttg atatcctaat tttttttttg gccctgccca ccatgtgtgt gcctgtgctg    21420
ccatgtcaca ctaagcagag taaaatgaag gaaggaacgg atgaaagggg caggaaagcg    21480
actcccagga gctgaaaggg caatagtata ggtcccttca gcacctagga tatgttgtgg    21540
gaagcccttr gaccccagat actaccctgt gcagataggg ataaaactcc acctgtccca    21600
gctcagtgct ctccccggct cctctggcct gcttgctggg cagggcccaa accagttcag    21660
gattcctttt tctctgtgac ctaccagtta gggttctctg tttactgtgt ctcctcctcc    21720
ttgttttgta tacccagctg ggtgggaaga aggtcacagc ccaggtttgc acgtggtgga    21780
ggagcagggc cagtaactgg ttaggcagag accccgccca ccaccctcca ctcccaccct    21840
agcagggcct gtgccatccc caggacaccg gagaccacca gggggctgga gaggctgcgg    21900
gagaaacagc cttcctggac acacccagct acggctcact tcccagcctg agctgttcct    21960
taggaattgc ttttctggga aacacaccct cttccagacc tgcagccttc ctttctatgt    22020 ggttttggt tttgctctct ggtgagggtt tctatttttt cctggtatac atgaatggca    22080
tgcaggaaag tggaatgagg acatcatgac caccatgcaa aggccattgc tcttaaggtt    22140
tgatgtaagc tccccactct cccaccccac taccctctg cctcggcctg ggtatgagg    22200 tcttggtttt gacaatcaga caatgttagc acactgctgt gtcttccacc tgcaatggag    22260
cactgtagga cgattttaaa aagcaaagtg gcaggccagg tgcggtgact caagcctgta    22320
atcccagcac tttgggaggc tgaggcgggc ggattacctg aggtcgggag ttcgagacca    22380
gcctgaccaa catggagaaa cccccgtctc tactaaaaat acaaaattag ctgggcgtag    22440
tggtgcatgc ctgtaatccc agctacctgg gaggctgagg caggagaatt gcttgaacct    22500
gggaggcaga ggttgcagtg agccgagatc gtgccattgc actccagcct gggcaacaaa    22560
agtgagactt ggtctcaaaa aaaaaaaaaa ttacaaagtg gctgaatacc aagatcctag    22620
gaactaggtt cagccaaact ggctgtgtgt cctggtagaa tgcccaccct ctgtctctgg    22680
gcctccatgc ccatctctgt agcatgaggg attctgatga ataatttcc aagagccctt    22740 cccacactaa tactccagga ttctgtaagg ttaatttggc aagaattcca acggcggaag    22800
aaagatggag ggaggaatat gtccagtcta ataaccctat gctcaagtca gaaagcccct    22860
cgggcagtgt ccgagagggc tacagccctg gccccagaac ctgagtccct ctaacctggg    22920
tcaaacccct aaaagccact ccagcaagag acaggcaaag cccgggctct tgctccaggc    22980
tggcattgcc ttgccgtgtg gctgtagaca tcgtttcacc tctcgaggcc tcagttttcc    23040
cttctgcaaa agacaggctg ggggaggttg ggcattttct tcttaactac caggagtctt    23100
tcctccaata aaattgtgat ggaaaccgga tgtcacacaa agggaaagga aacactggca    23160
tttctggagt gtttgaagca tgtgaagtat tgtttaaggg cttttgcaatc attaatgtac    23220 tttgtgctca cattaacccc acaaagtagg tgctattatt atccccattt gacacatgaa    23280
gaaactgagg ccctgaggag ttaagccact tgtccaaggt aaagagtggg agctgggctt    23340
ctgataggga gtgggcctca gtcatgaaac cacaagactt gtgtagttcc aacccctgg    23400 ggacatctcc aggcacttga cccatgctct tccaacattc atgtatgcac gcacacgtgt    23460
acacacacgt gcacacacaa acacacacat gtgtgcacaa acacatgcat gcacacacaa    23520
acacatgcat gcacacacaa acacacacac atatatacac acaccaacac aaacacacat    23580
gtgcacaaac acacgtgtgc acacaaacac acacatgcac acacacacac aaatgcacac    23640
acatgcgtgc acactgtggc tactcctctg tagcctgctg gccacactcg gctcaagccc    23700
```

```
caaatcaaag gtgactagca agattgcgag acagatttct ggagatggga aactgcgtca  23760
tcaaattgtc tcagggacgg aacacccatc agagccctgg gggagagaag agacacgggg  23820
tggctgccaa ttttgctgac ctatgctgct gactttccag cagccccga ctcctgtggc   23880 cagctgagcc caggtccaag ctgcccctg cacagggctt gttccctgga gggctataag    23940
ccacagcatc ccctccaaga cagccagtcc tgtgaacctg ctcaatccct cactattcct  24000
tggggcctgc cctgggagaa gggagagttc cctggacccc ttcttgggac ttgcggtgac  24060
aggggtgtgg ctcacttgct caaatccctt gtgtgagggg aagcatgcaa gcaagtgggt  24120
gctggggccg gggcaagcgc ttttgggctc tggccctaca gtaccgtcta ggttgtgtt    24180 acaattaatg ctcttttaga agttgccatt cactgatggc taagtgttaa ccaactcagt  24240
ggagagtgag ggtgacagcc ttttacaccc tgccctcttg gtacctgggt ccttgtctgg   24300
catccaggaa gaatcaggtc acacggactt gaaggatggt gaatgcagag gttttattga  24360
gtgatggagg tggctcttag tcgggtgggg agctggaaag gggatggagt gggaaggtac  24420
tcttccagat ggctgaactc ttctccaact gtccagctgc ctcttccaca ttcagacact  24480
tcttctcttc tctccttctc tgccatgctg ctctgctcct ctgccagtgg agtttggggt  24540
ttttatgggt ataggatggg gggcatggtg gccagggtg gttttggcaa aagcaacact     24600
caggtgggaa aacaggaatg tgaagttctc atttagggcc gtgggcccag gcttgtgggt  24660
ggggcttttg ccagagagct gtcctcctct acccagtatt ccctgcctc ctgtccatat    24720 cacctgcacc aagaacctca ctgggtggga gccaatccag agccagagaa aggacttgac  24780
acttggcctc aggcagaccc aggcttgaat cctggccctg cctctgatga gcagggtgac  24840
ctgaactgtc tcaggttgcc tcgctgactc tgctttccca tctggaacat gggaatagca  24900
atgcatcagc cactcagtgc agtgttgagg ctggaacagg tggggcacac tgtgagctcc  24960
atttcctttt gcctccaccc agcaattatg tctgctgggg agaagaggag aaataaggat  25020 cacccctgc cctctatcag tcagtcaacg accatttatt aaacacctac taggtgtcag    25080
gcacttgaca gagaaatgaa ataacaacac aagcaactct tatagctata ccctataata  25140
aatgttatag aagcaggagg caggtagagg tggaagagaa ccttctgctt gcaggggat    25200 atcagtcaga gaaacagaac caataggaga cacagattaa gagatgtatt gcaaggaact  25260
ggcttatgtg attgtaggga tgactaggca agtcagaagt cgcttgggaa tgccagaaca  25320
ctcagccttg gaccgaagct cctgcccgca agctgaattt cttcttcttc caggaaacct  25380
cagatctgct ctaagtcctt tcaactgatt gactcaggcc catgcaggga gttgaggaca  25440
agcttcctta gtgaaagcca gctggctgtg gctgtcacc acacagacaa actgcttcac    25500
cccaacacca agattagctt gaaatggaat aactggggcc tgtcatccag ccaggtggac  25560
ccacagactc accgcagcag agcacctaga ggcggccacg gagggttagt gacagagcag  25620
aatcaggcag ggcacccggg caggggcag acccagcaaa ggctcctagg gcagattgta    25680
gaagaggtcc ttggagatca gggagtacag caacgtggct gtggcactat taaattaaat  25740
taaattaaat tgaaaataaa attaaattaa aaaggattgg tggctcacgc ctgtaatccc  25800
agcactttgg gaggccgagg caggtggatc atgaggtcag gagatcaaga ccatcctggc  25860
taacacggtg aaaccctgtc tcttctaaaa atacaaaaaa aaaaattag ccaggtgtgg    25920 tggcgggcgc ctgtagtacc aactactcgg gaggctgagg caggagaatg gcgtgaaccc  25980
gggaggcaga gcttgcagtg agccgagatc atgccactgc actccagcct gggctacaga  26040
gcgagactcc gtctcaacaa aaaaaaaaaa ttaaaaagga ttggaataaa ggaatggttt  26100
```

```
agtaaacaaa aataaacaaa tgcaatgcct tttttgaagg cgtcattact acagccatga   26160
tggagcaaca cggataaatt cccatgacag gaggtttcat gtaaaaccac ggtgacagaa   26220
catagttgga tgtggcatac ataaacagct gtgcccaggg atggaactct gggagatttt   26280
cccattagtt ttaaatgctc tttcatgtag ttattctttt attttttatgt ttttgagacg   26340 gagtctcgct ctgtcgccca ggctggagtg caacggtgcg atctcggctc actgcaacct   26400
ctgcctcctg ggttcaagtg attctcccgc ctcagccccc caagtagctg ggattatagg   26460
cgcccgccac cacacccagc taatttttat attttttagta gagacggggc ttaatattag   26520
ttttaaatgc tctttgctgt agtttttttt tttttttgag atggagtctc gctccgtcac   26580
ctaggttgga gtgcaacggt gggatctcag ctcactgcaa cctctgcctc ccggttcaag   26640
cgattctcct gcctcagccc cccaagtagc tgggattata ggcacccacc atcatgccca   26700
gctaattttt gtatttttgt agaagtgagg tttcaccatg ttggccaggc ttgtcttgaa   26760
cttctgacct caggtgatcc acctgccttg gcctcccaaa gtgctgggat tacaggcgtg   26820
agccacagca cccagcctag ttatttattt atttatttttt tttttaaaga gagagatgtt   26880 attttttta agggaatga gtggtattag gatgtcaaat gaaattgctt atttaataaa   26940
actgaaaagc ccagtttggg gaaagaaaca aaacacactg agcagaataa tctaaccaca   27000
gtgaacagga aaaaaagcca agaataaaat aagttccggg gtatccaagg gtgagcaaag   27060
ccaggccggc aggcctcctc ctcccttgca gaaagcagga tggatgaggg gctctgcttc   27120
tccaggctcc ctcatgtccc cactgaaagt gttttccagaa cattccaggc ccataaagtg   27180
tccaaatgct ggaaggactt acatgtatat gtctgggatt gaatcaaatc ttctgactca   27240
attctctttg ggagttctga gaatggaggt cacttcccag aacccgtct tccccctaca   27300 gacagctttg gccttctttt cagggaagaa aagaaaaggg actcttggaa accctgctga   27360
gggccacgca gctctggttg ttgaggctca tatggtttat gaggcgccat caccccttc   27420 cgccaccccc tgcctgctgt ggcctgaggc ttaccttcgt gactgccta aaaacagcat   27480 ccagactcag taaccacgtc aatcagcttt tagaggaaaa catttattct ggggaggtgt   27540
cagggaaagg attcaggaga tcttggttct ttctagctct ggccttgaca tcgacttgct   27600
gggtggtctg aaggatttca cttatttaca gagcgaatat tgttcaagag tttgggatgt   27660
gcaaaactca gctgcaggcg tgatgcaggg tgggaagatg agcaaggcag ggtcctcctc   27720
tccaagtaca gcgaatatgg tgggacagat gcacatgcac tttatgcacg catgcacgca   27780
caccatgtgc tcagctgcca ctgagaggag ataggagatg cagagggaga gggagaacag   27840 ccgcccctctg actaaggatg gagcccagct gtctcaagag ctctcctgga tggacagact   27900
ggtggcgtcc cagcaaaatc ccccatctct ccatccggct gtgtaatgaa tgactggaaa   27960
cctcagctgg cctgtgagca ggagatctgg ccaggtggaa gggaatccct gacaccccac   28020 agccctggt gtagctaaag cagacgggcc tcctgggctg gtgcaggaag aacagcttat   28080
gttctcgaac acattgacca cgtgctccat gcatctgaca cacacggact cgtctactcc   28140
acacagcacc ctaggagatg gggctgttta aaataccaat ccccactgta tagttgaaaa   28200
aaacgaggtg caatgaggtt aaataacgag ctctagagag gaggactcaa ttcacagtca   28260
gcttccagag cccatcggcc taaccgccag gctggcttcc cgtccgtaat gcacgtttcc   28320
agctagaggc tttcaggctg tgtttcccac acttagccat tgacattcac gttcacagtt   28380
tttgccacat ccatgtcacc tgtacaacca tttctttagt agtgacttac ttttgaactg   28440
```

```
caacttcatg tcaccaattt aaatggaaaa tgagtatcac ttatcataaa aaagatgata    28500
actgtacaaa ataaaagcaa tagaatgtga acaatgctat tagagcctgg gtagattcgg    28560
ggaccagcca aggctctgaa cctgctcagt ctgttgaaaa aggagattac gcacatagaa    28620
aggcgttgaa gtgcacggac accacgctga gacgttcttg ttggcctaat caggaggaac    28680
gactagatta ttcaattcaa ggttgtttac caggccaaac tacttccctt gctgggaaat    28740
gcttcccagc tctaacgtgc agtcagaaaa tacgggacac aagttgacat ccgaaggaaa    28800
aatatctttt ccttctccac ttccgagttc ttggttgggg ccctgaaac aaaaaacaga     28860 tgaacaagag aaaagtgaac aaattaattt aatgtaagtt taatgtgaca tgggaacctt    28920
cataaggaaa tgaagtgatt aagcctgagt gccttttgt ttttttgaga cagagtctcg     28980
ctctatagcc caggctggag tgcagtggtg cgatacggct cactgcagcc tcgatcaccc    29040
cgggctcagc tgatcctccc acctcagcct cccaggtagt taggaccagg actacaggtg    29100
tgtgccacca cgctcaccta atttttggt acttttgta gacacagtct cggctgtgtt      29160
ggccaggctg gtctcccact cctgggctca agcgatccgc ctgcctcagc ctcccaaagt    29220
gctggggtca caggcatgaa ccactgtgac cggcctgagt gtttccatta gatgtcatga    29280
acagtggaga atcatggggc tgtggtggga ccaggggca cgagcgaagt acagagaact      29340
ggagaaacag caaggcctgt cggggctcct ctcagtgtcc ccagtgctcg gagtggacgg    29400 tgccccttc ctctggctgt ggagtctggt gtcctgcttc agggaacaat cacatagtcc     29460
ttctgcgcct gctgtttctt ggattctttc cacttaaaat attcaacatg cgaagctgcc    29520
acattttggg gtagcgtgcc ctgaatcatt ggctacaagg tcgcgggccc cacatgaggc    29580
acagttggcc cttgagacag tgacactatg tatttcgtgg aggccactgc ttcaaaggcc    29640
ctaaggtgtg gattcctggg aaaccaaaac aggctgtctc caaggctcaa gtggaattga    29700
tttctaacag cccaggccca cggtgtctgt gcgagtaaat gaagaaagtg ttttacagt     29760 aagtcttctt ggatagaatt ctgagggaga gagagaatga gtgaatcaga atgttggatg    29820
ttccctctaa ggcatctgtt taaaaaatca ggggaaaaac ccaggagcag agtcatcacc    29880
tgtccccagc tctgaggatc tgtgtctgtg aggcacatga gtccaccctc ctagctctgt    29940
agacaaggaa actgtggtcc agagagatgg agatcccaca gacaacggcc cacctggagc    30000
accccctccc cgcctgactt tatattccca ggatgcattc atcagggtct cagtaaaaaa    30060
aagagggcac attccaattg ggtaatagga agaggatgtt aatgaagcgt ttctttacag    30120
tgctgtaggc agcatattgg ggttctgcga agagcaggca gcaccctggg tgcctcaggg    30180
ctggtacggc aaagcctcag caccctccct acctccttcc cccctcgcga tcaggcccct    30240
gataaaagca gtgaactctg ctccaggtct ggccagcata aaggccccca agagaggagc    30300
caacaacacc ccatcctccc tctcaccctc cctcaggctc ctgctggggc tcccactggc    30360
caaacccaaa gagaagccgg aaggcaaaga gctccgtggt acccatcagg gctcccaagc    30420
aggggccaca gaggagaagc caggaggtga cctggagcag gacacagcag ctccctgaca    30480
gggatcctca cccagggcac gcctctagag cagatggaga aaacaactca gtagacttca    30540
gactcccaaa ttctcccagt tcctcaaccc gcctgccctc tggacttcgg gagaaagttg    30600
agagggaaag ccctcaactt tgttttgaaa atgagagcaa tgtttacagc cactagcaag    30660
caattaggat ccagctgggc tgatgtggcc agatctgggg acacccagcc aggtagatgc    30720
acaacagacc cataatggag gccagcgagg aaacgctgga cacgtccccc atgactgagc    30780
tgtgaggacc tgacttatct gtgcggcggt cactgtcgtg tagaaatgga agctgtacat    30840
```

```
gcaggctgag gcttctcagc tggacagttc agcccgagtg agccccaaga ggacagggga    30900
ggctggtctt cattcttccc ctctgaatca ccagcaaatg atagaccgtc aataatttgt    30960
taaatgcttt ttaaaatgaa tgctttaagc cgggtgcagt ggctcacatc tgtaatccca    31020
gcactttggg aggccgaggc gggtggattg tttgaggtca ggagttcgag accaacctgg    31080
ccaacatggc aaaacctcat ctctaccaaa aatacaaaaa ttagccaggc atggtggcag    31140
gcacctgtga tcccagctac tcaggaggct gagacaggaa aatcgcttga acccgggagg    31200
cagaggttgc agtgagccaa gattacgcca ttgtactcca gcctgggtga cagagagaga    31260
ctccgtctca aaaaaaaaa aaaaaaaaa aaaaaattac gcttcaaaca catgatctct    31320
caccactgtt gaattttctt tctatgagcc caggagggcc tctcagagag gaaagctcct    31380
aggtcttcct ttccctctgc aaactccctg ccttgaagga tcagaaggac tgtgctgctc    31440
gttgcatcct ttgcaagttc caaaccctga tcccagctgt gcttaggggt tcctgcaaac    31500
cttttccagg tgttaattac ctcccacttc atttcctgtt taccaactca gcttttttgtt   31560 ttagtgtgtt tgaattccct gaactgaccg ttgtctgatc tccacctccc aactgaatta    31620
ggggagctgg gcttctggaa acccaggtgc cgggtgttgc agagtggctg aaagctggga    31680
tgtggcagat ccgtggctac attcatgcac acacacacac ccacataccc acacatgcac    31740
acacacacac acacctgcac tcacacactt gcacatgcat agaccacagc tttccacacc    31800
cttcctagac aggggtcact tggtgtcctg gagagagtgt gaagtctgga agggaaagag    31860
gggggattaa gccccacctc tagccatggg actgagacaa gtcacccccca cccatctgcg    31920 ccttgtttcc tcctctgtga ggcaagcaca gagcccatgc ctccctccct ggatgggagt    31980
gatgtgaaac ttgaagaggg gtagagacaa gggtcgtcaa tggaagcccc ttgggcaaaa    32040
aggccctttc aactagggc acagaggagg ccctgggctg agaacttgac agcacccttgt    32100 attggtaacc agccggaggg actggaaata ctcagatgtg tctgtctccc ttattaggtt    32160
caaagtccct cgagaccctg tctccatcac agtgctccag tccagacccc tcctctgagc    32220
tccagaccct gctggaccca acagccatcc ccatccccac ctgccctggaa ttctccaaag    32280 aacctcccct ttaacagttc cagcctttaa cagttccagt ctaaacacat gacctttctc    32340
ctctaaatca gccccccatc tctgcctttg caggagatgg aagccatgac acctgcctcg    32400
cccctgtcct caccccatcc atgtccaatc aagcactagg catgtcaggt ttaccctcta    32460
aactcctctg gaatccagtc tctcagtctc catcatccca ggtcgaagct aatgggctaa    32520
ctggtccttg cttccactct accccactg cagtcctgac ttcctgagca gcagccaggg    32580
cctaatccat attcacacca agcgccttcc tgactgagat atcctcctgc accatcatcc    32640
ctccaccctg tttagttctg ctcaccctca gtgttctcat caataatcca ctcgccctca    32700
caggcgcgtt tgggacccca tgttctatgc tctcacagga ccttttgctt gatttttcac    32760
tgtactcagg tcagtttgca gttattaagt gactgagcaa tgtctggctt ctccagtaga    32820
ctgtcagctc ctagccattg tatccctagc accgctgtgt gggagcactt cacaaacgtc    32880
cattgagtca gggactcagc agtctccatt tctcctccct gctggagaat gcgtgtattt    32940
tgcaatcccc agccctgtg ccatctaacc atctttctt ctctgttcag cccaggtgtg    33000
gcctcactca catcccactc tgagtccaaa tgttctctcc ctggaagata tcaatgtttc    33060
tgtctgttcg tgaggactcc gtgcccacca cggcctcttt caggtgagtc aaagggattc    33120
ctcagttcac tagttagggg aggtgggcag acaccctgga gaactccctg gaaagctcaa    33180
```

```
ctctcatgcc ccggacaaca gttgaaggaa ccagtgatgt taagcccaaa gacaaaacct    33240
ctcaggtgtc caagtccctg taggcctgtt gggagcagag ggaatgttct gcggaactag    33300
aggaagaggg gctcagggag aagaagggca cattcctggt tgtcatatgt gatctatccc    33360
agatgaactt ggaagtgaag ggaagagagt taaacattaa agtaaatacc cagtggatca    33420
gacagcaatg tgccagattg ccttggagac aaaatatctc caacacatgg ctgacatttg    33480
gtgggagatc agaacaccct aaagagagaa tttaagggga gggggaggag gacctgagcc    33540
agagtagaag cagaggatag ggagatctgt tcttggggac agcatttgca agaaacaagg    33600
ctgaggggtc cactccaacc tctccaccct gctgcaggtg ctgcctatga tgaagatgag    33660
cagatggcca tctcagctgg ggccacagtg cactggacct atagtttcca attccgcact    33720
cagcaggcat ctttctgatg atccgatggc ttctcagagc cagggatggg ccaggatcca    33780
tccccttggc tactgtcttg ctgagaaatt aataagcagc atctggtgct atactttggt    33840
ctctagtgag ttagctcatg aaagatgaca gactctccaa gccaggggta tgcaggaaat    33900
gggttttctg tagctacaga aatggggttg agggttggac caaggggact acccagggga    33960
agtcttacct tcagaggact ctggaaagga ggctgcaagt tttcatgggt caagaattca    34020
gagcccagta gagacagctt atctctgttc caagatgtct ggggccttgg ttggaagatt    34080
caaaggctag gaaaccagga gccaccaaaa gcgtaactgg ggccagagga tccactttca    34140
aggtggcaag ttggttcccc ccatgtggct gcttgagtat cctcacatgg cggctcacat    34200
ccttccaagt aagcaatgca aaaggccaag aaagatgctg caaagcatgt tatgacctag    34260
cctcagaaat cacacaccat ccctgccacc attagtaaga agtccagccc acgtccagga    34320
gaagaggaag cagattcctc cttttgaaat gaagaatatc aagtaattcg gggggcatat    34380
gaaagccacc acacaccaca gggatctttt tagagcatac ttcttatacc atcactgtag    34440
ttccttaaga ctcaggggca aagcctcact tccttagcac ccagtgaaga ccacgcttac    34500
tccctcactc aacctcttgc tacttcccac ctctcctgtc aacatctag  tgtcactttc    34560 cagaacatac caacagcttc cccagttctg tgcctctgct caggctgttc cccctgcctg    34620
gtccacttgt cctccttctt gtcccgtcaa aatgcttctt atccttcaag cccagctct     34680 agagtcacct ccaaccccctt acccaccagc cccctctcca agtctgtgtc ccacaacccc    34740
cctgctccct ccagggcacc ctccacccct gggccacag ttgtcaggag tcaggcaggg    34800
caggggccgg gtggtgtctt ctttgtgttc ttgcactcag ggcagagctc agcacagagc    34860
agacgctcaa aaaacattta aaggataaa gcattgattt gtgggtcccc cagtctggct    34920
ccaggatgcc agccagctgc tcctagaagc aaacggactt ttcctgggaa atcccagagg    34980
tgatgatcag tatctctccc gtgactcgta gttcagctct tcctccatga gcctgactat    35040
cagtggacct tccagaaaga gccccttttc cttctctcac ccacagcaca gggcactggg    35100
aaaatgccca atgagtcctg ccctctgggt tgtgctttgg acttttcagt gtgtcttcgc    35160
atccactctt cagcttgaat gttgcaacag ccatgaaaaa agaaatgcaa agcgattcag    35220
gatgagagca ataccctact ccaaagaagg caaaatagaa gctcagagag gtcaagcatt    35280
ttgcccaaga ccacacagct aggagtgaa ctcatggctg tccaagcccc acgcctctgc    35340
tgaaggtaga gatgaattac agcaacaagt ctagaaaggt gcctgcccta tggtctgtga    35400
gtcttgccta agaatgaaag aggagccagt gggttaaaga tgaggtcacc aacaaacggt    35460
ggtgttggag tttaccactg gttatttta tgggtttgca agaattgtta attactaatg    35520
tttattgagc ctagtgcagt gcttggggca ttttgcacat tgtctctgat ccctatcaca    35580
```

```
accctgagag gtagtttttt taactcccat tttacaggtg aggtcattgt ggttcaagga   35640
cgttaagtaa cttccccagc gtcacacggc ttataagtaa ggcagccagg atgtgaaccc   35700
agtaggacta tctggctgca aagtcccac cctccctcgc catctgtatc ctccaatcat   35760
cttcagtgct ttgctgatag aaggtacgga aatacgatgc cacagactgt ccaggaagac   35820
agaaactagg cagatgggct ggccatggtc tccaagccag actggaatct ccaggtctgg   35880
aatgatatca tttttctctt ttaataaatt aactcaccca ccacacggct ttgagaggct   35940
caaaggtgac caactccctt ggggggccc cggttgataa ggaaggaatg tgaatcctcc   36000
catcacggaa gcttcaagga ggtcaagggt ccaacacttg agattgttag tgctgttggt   36060
ggatactggc caaggaaata tcccagtgga gcctcgagat gaagaacatg aggcccccgt   36120
ttagatccaa ggatcagagg gggctctgta agacccaggg gagtcaggtg cactggagcg   36180
cgggctgcag aaaacagcct gagctccacc tcggcttctc cttgccctgg ctggttgtcc   36240
ttaacccctg tctccttctg gaccagtttt tgtccttccc ttgtgaccct gaggggtaac   36300
agcctctttt ccactttctt tcagcgccga catgctcaat gtcaccttgc aagggcccac   36360
tcttaacggg acctttgccc agagcaaatg cccccaagtg gagtggctgg gctggctcaa   36420
caccatccag cccccttcc tctgggtgct gttcgtgctg gccaccctag agaacatctt   36480
tgtcctcagc gtcttctgcc tgcacaagag cagctgcacg gtggcagaga tctacctggg   36540
gaacctggcc gcagcagacc tgatcctggc ctgcgggctg cccttctggg ccatcaccat   36600
ctccaacaac ttcgactggc tctttgggga gacgctctgc cgcgtggtga atgccattat   36660
ctccatgaac ctgtacagca gcatctgttt cctgatgctg gtgagcatcg accgctacct   36720
ggccctggtg aaaaccatgt ccatgggccg gatgcgcggc gtgcgctggg ccaagctcta   36780
cagcttggtg atctgggggt gtacgctgct cctgagctca cccatgctgg tgttccggac   36840
catgaaggag tacagcgatg agggccacaa cgtgcaccgct tgtgtcatca gctacccatc   36900
cctcatctgg gaagtgttca ccaacatgct cctgaatgtc gtgggcttcc tgctgcccct   36960
gagtgtcatc accttctgca cgatgcagat catgcaggtg ctgcggaaca acgagatgca   37020
gaagttcaag gagatccaga cagagaggag ggccacggtg ctagtcctgg ttgtgctgct   37080
gctattcatc atctgctggc tgcccttcca gatcagcacc ttcctggata cgctgcatcg   37140
cctcggcatc ctctccagct gccagggacga gcgcatcatc gatgtaatca cacagatcgc   37200
ctccttcatg gcctacagca acagctgcct caacccactg gtgtacgtga tcgtgggcaa   37260
gcgcttccga aagaagtctt gggaggtgta ccagggagtg tgccagaaag ggggctgcag   37320
gtcagaaccc attcagatgg agaactccat gggcacactg cggacctcca tctccgtgga   37380
acgccagatt cacaaactgc aggactgggc agggagcaga cagtgagcaa acgccagcag   37440
ggctgctgtg aatttgtgta aggattgagg gacagttgct tttcagcatg ggcccaggaa   37500
tgccaaggag acatctatgc acgaccttgg gaaatgagtt gatgtctccg gtaaaacacc   37560
ggagactaat tcctgccctg cccaattttg cagggagcat ggctgtgagg atggggtgaa   37620
ctcacgcaca gccaaggact ccaaaatcac aacagcatta ctgttcttat ttgctgccac   37680
acctgagcca gcctgctcct tcccaggagt ggaggaggcc tggggcagg agaggagtg    37740 actgagcttc cctcccgtgt gttctccgtc cctgccccag caagacaact tagatctcca   37800
ggagaactgc catccagctt tggtgcaatg gctgagtgca caagtgagtt gttgccctgg   37860
gtttctttaa tctattcagc tagaactttg aaggacaatt tcttgcatta ataaaggtta   37920
```

```
agccctgagg ggtccctgat aacaacctgg agaccaggat tttatggctc ccctcactga   37980
tggacaagga ggtctgtgcc aaagaagaat ccaataagca catattgagc acttgctgta   38040
tatgcagtat tgagcactgt aggcaagagg gaagaaagag aaggagccat ctccatcttg   38100
aaggaactca aagactcaag tgggaacgac tgggcactgc caccaccaga aagctgttcg   38160
acgagacggt cgagcagggt gctgtgggtg atatggacag cagaaggggg agaccaaggt   38220
tccagctcaa ccaataacta ttgcacaacc atctgtccct gcctcagttc cctcttctgt   38280
aacatgaagt cgttgtgagg gttaaaggca gtaacaggta taaagtactt agaaaagcaa   38340
agggtgctac gtacatgtga ggcatcatta cgcagacgta actgggatat gtttactata   38400
aggaaaagac actgaggtct agaaatagct ccgtggagca gaatcagtat tgggagccgg   38460
tggcggtgtg aagcaccagt gtctggcaca cagtaggtgc tcattggctc ccttccacct   38520
gtcattccca ccaccctgag gccccaaccg ccacacacac aggagcattt ggagagaagg   38580
ccatgtcttc aaagtctgat tgtgatgag gcagaggaag atatttctaa tcggtcttgc   38640
ccagaggatc acagtgctga accccccac caccagccgg tacctgggaa ggggagagt   38700 gcaggcctgc tcagggactg ttcctgtctc agcaaccaag ggattgttcc tgtcaatcaa   38760
tggtttattg gaaggtggcc cagtatgagc cctagaagag tgtgaaaagg aatggcaatg   38820
gtgttcacca tcggcagtgc cagggcagca ctcattcact tgataaatga atatttatta   38880
gctggttgga gagctagaac ctggagagct agaacctgga gaactagaac ctggagggct   38940
agaactggag aggctagaac caagaagggc tagaacctgg aggggctaga acctagagaa   39000
gctaaaacct gagctagaag ctggaggact agaacctgga gggctggaat ctggagagct   39060
agaacctgga gggctagaac ctggagggct agaatctgga gagctagaac ctggagggct   39120
agaatctgga gagctagaac ctggagggct agaacctgga gagctagaac ctagaagggc   39180
tagaacctgg agggctggaa tctggagagc tagaacctgg agggctagaa cctggagggc   39240
tagaacctag aagggctaga acctggaggg ctggaatctg gagagctaga acctggaggg   39300
ctagaacctg gagggctaga acctagaagg gctagaacct ggagggctag aacctggcag   39360
gttagaacct agaagggcta gaacctggag agccagaacc tggagggcta gaacctggaa   39420
gggctagaac ctgtagagct agaacatgga gagctagaac ccggcaggct agaacctggc   39480
aagctagaac ctggagggaa tgaacctgga gggctagaac ctggagaatg agaaaaattt   39540
acatggcaaa gagcccataa atcctgacca atccaactct gaattttaaa gcaaaagcgt   39600
caaaaaaaag attccctcct tacccccaac ccactctttt ttcccaccac ccactctcct   39660
ctgcctcagt aagtatctgg aggaagaaaa caggtgaaag aagaagtaaa aaccatttag   39720
tattagtatt agaatgaagt caaactgtgc cacacatggt gaatgaaaaa aaaaaaaaga   39780
ggctgtgttt tgtcacacag ggcagtcatt cagcaccaga gcacgtgatg gtctgagact   39840
ctcttaggag cagagctctg ccgcaatggc catgtgggga tccacacctg gtctgagggg   39900
caactgagtc tgcgggagaa gagcggccct atgcatggtg tagatgccct gataaagaac   39960
atctgtcctg tgaaagactc aatgagctgt tatgttgtaa acaggaagca tttcacatcc   40020
aaacgagaaa atcatgtaaa catgtgtctt ttctgtagag cataataaat ggatgaggtt   40080
tttgcatagc tctagcattt gttacaactc ccgaaacccc cgagtttggt ccctggggta   40140
ccgccttgca cactcagaag cctttgggaa ggggtgctat tcatttctgc tcaatctgtt   40200
aacaggcttc tggcatgtag atcagtggtc tccaagcttt tgtgattgta tattcctata   40260
ggaaaaaaag aattgattat gcatacccag tatgtatact tattaatctg tatgaagatg   40320
```

-continued

| | |
|---|---|
| tacattctaa aatataatca accagtagaa atttaagaaa gaagatgtaa aaaaaaaaaa | 40380 |
| tattaacagt gcttgaatat ttccttccat cttacatttc tgcagggata actcattacc | 40440 |
| aagttcccac tacatgaatg tgagaccctc atgaggccta gaatcatagg cgcagcagcg | 40500 |
| attcaatcat ttattcatgc aatatagact tactgagtgc ctaccacttg acttcccttc | 40560 |
| aaatcaggag tatcttctac aatatcctga tgaaaagcca cttgtttcat actcccagtg | 40620 |
| atggggaatt cattatccat gccactttgg gatcccttca ttattcatgt attcattcct | 40680 |
| tcactcattt attaaacaaa acttgcctag tctgtctcca taaatgcccc tcctccatcc | 40740 |
| atgcatccat ccatccatgc caggaacctg gggctcatcg ctcaacgtac cctctccttc | 40800 |
| atctgttcca tctggtgggt cagcacctct tttatttttt tctaacttt a | 40851 |

<210> SEQ ID NO 12
<211> LENGTH: 5840
<212> TYPE: DNA
<213> ORGANISM: Homo sapiens

<400> SEQUENCE: 12

| | |
|---|---|
| ggcactagga atgtggtgat gtgtaccccca aaatttttatt atgaaaggaa cagtagcttt | 60 |
| ggggacctag gtcctgggtc tgggagtgca agaaccaggg cattctgaag gccaaggctt | 120 |
| atatttcagg gggaactggc agctgagatg ctagtatctt ggctccgagt ggtgcaggga | 180 |
| atcagagccc taactgctgg tgtttgaggg caccaggtct gggggtgcag ggccttaatt | 240 |
| gagactgagg tatatggggc tttgtaccag gggtcactga ttcctccgtc ttcctgtttc | 300 |
| tgcttcccct cagtcccccc ttgcctcact ggctgctccc cagagcaaag ccccagagcc | 360 |
| acaggccctg ccccacctgg cttcaacccc aggaatgcgt ccagcgtgat ccagggcctg | 420 |
| cagaacaggt gctggttctc cctccccgtc tacagctctg gggatcggag ggggggggg | 480 |
| caattgtcca gccccaggc aacaggggaa gggccttggc caacatctgg gtgccagcag | 540 |
| ggcaggggtg gggctctgag gggataaggg cttttaaaag cctccccagg gaggttcccc | 600 |
| agttcctcca cctgctggcc cctggacacc tctgtcacca tgtggttcct ggttctgtgc | 660 |
| ctcgccctgt ccctgggggg gactggtgag acagtggggg gatgtgggag ggggaacggg | 720 |
| ccctgattct cttgctggcc tcacatcccc ccccgataag accttcccct ccaacacccc | 780 |
| accctcatcc ctctggccca cagtctatcc tagtccgggg tgccccggct cttatctatc | 840 |
| ttgcgcggcc ccaccctaaa cttccacccc cgctcctcca tgttgtcata gtgctcactc | 900 |
| ccacaccaga ttcctgctcc tcccaggaag cctcagtact ttctcctctt ccctagccaa | 960 |
| cgccctgtcc caccgcttta ccaaaggggc agattctggg ccatctctgt ctctctctgg | 1020 |
| aggaccccaa ccctccatg ggcttccccc accccacagg actctgatca tcccctcctg | 1080 |
| cccctagtt ccctgcggcc acctatttgg ctcctgagtc tacaaatccc accacactcc | 1140 |
| agtgactttt tccatccagc tgtccgctct caactgtgtc ctccagaccc tgacatctgg | 1200 |
| tctccccagt ccttccaggg tccccaaat ttcaccagaa aaccctgctt cccaaactgg | 1260 |
| catgtgggat cccccatctg gtatgggggg gggtctgcaa atgtcccttc ccacccagca | 1320 |
| cccccagctc tcccaggaaa aacaccacac cctcccacca catgctcctt tccttgggaa | 1380 |
| agttccatcc cgccccaggc ccagcccctt ctctgcctga attgttccta cacagctctg | 1440 |
| gttttctgga accccacccc aaggatcctg aatgccttct cagccagcgc ttctgccctg | 1500 |
| gcctcccca agtcagtatg tgattctaca acctcacgtc aagtgggtcc tgcattgcat | 1560 |

```
tcccacagct gcttggcgcc tgttctcacc acttctccaa tcctcttcct aggattgcct    1620
ccaagaggac cccatatcct tccagtaccc tcagaccatg aaccccatcc ccatgagaaa    1680
cgaagatccc atccttcacc ctgtccgaga aggactgcca ctcacgcctc cctcctcctg    1740
agccccgtcc cagtcctgac cgcaactgtg ttctcagggc cccaacctcc cctcagattg    1800
ccattcctgg ttcacaggaa ggaccccaaa acctctcgga agcccacctc tagccttaac    1860
catagccctt tcttttaccc tttaaccagg aagccctgaa atctaactgt cccagccaag    1920
ctggccccctt ccaaccccaa tgtagggacc ccaagtcacc cccaaactct tcagtccaga   1980
tgctcttctt tacctctcag acctggttcc ctaaagctgc atcctttcct gaacctcaaa    2040
agcccaaccc aggtcctgtt ccctagcct aggagcccct tagccctcca gattcttcct     2100
cagtgagcct ctgatcctgt cccacccttg gcgccttgat ccctggtttc cagaatccct    2160
ttccactccc ctaacccacc acctcccatc ccccagcccc agaccccaaa tgacctgacg    2220
cccagatgca gtgtctgctc cagacactgt ctcctgtctc ctaccctgat ccctggaggc    2280
tgctctactg tcagagcaca aaatctcccc accaggtcca gccaccactc caaaagccca    2340
gggaacagtc cagagtccca cccttccca acacccttg cccatgtccc caacctccag      2400
ccctggtcct ctacccgcaa tgtcccttca gacccacagc ccagctccct ctcctagcct    2460
tgtccctggc ctctcctgcc aaccctgccc ttcctgaccc agcaccgcct ctgcaggtgc    2520
tgcgcccccg attcagtccc ggattgtggg aggctggag tgtgagcagc attcccagcc     2580
ctggcaggcg gctctgtacc atttcagcac tttccagtgt gggggcatcc tggtgcaccg    2640
ccagtgggtg ctcacagctg ctcattgcat cagcgagtga gtaggggcct ggggtctggg    2700
aggagggcat ctatgctgcc acaggattga caggccagtg gcattcccct tggataacct    2760
caggcaagac tgggggggctg aggcagagag gaaggctctg gcgcaggtcg cctggcaggg   2820
cagagctggg ctggacaccc ctctccaagg ctgcctgggt ctcttgggat ctggttctgc    2880
ttgtgtctct gtgtgactgt gttctggtct ctgtcttcct ctctctcctc tgtctccttg    2940
tctctgcatc tcccctgtct ctgtctgtct ctgagtctct ctgcggcatc tctgtcactg    3000
tgtctcaccc tccatctctc tacccatctc tctctctctg gtctctacc tcaccgctcc     3060
ctcatcccta ctaaacacac acccagatgg acctaaggga ggccccagag taaaggaagg   3120
gctttatccc caacttgtgt gcctgggagg gggcgcctct ccctctgtcc agctccccgc    3180
cccacaggat atccctccac tctggagaga cacagggaag ggctggtttc agcgggagct    3240
gggtggggca actgagggag gaggaaggag gaggcgggc gagaaacgcg cgggagggtg     3300
ctgggaaggg aaggggggcct cgaccttgga cttcaggcca ggccacctgc ccctggggag   3360
cccgcaccac agccccagct gcagctgagc cgctctcagg cctcccctcc tcccctacctg   3420
cccccaccct cccacctgc cccaccctc cccagggcc tccctccctt ttctctccca       3480
cactcggtca ctcctgcttc ctctctgcct ctgtttctag ttctcactct gacgtcccgc    3540
gtccttttc atttgtctgc ttctcgctcc cttccgtgtt ctgttccctc ttcctccctc     3600
ttccctgggc ctgttctcg ctgtccctgt cttttatcct tctcatctgc ctctttttg      3660
ctcaccctgt ttctcactgc cctccctcc gccttttca cccctctgtc cttttgagct      3720
ctttttgct ctgtctcttc atttgccttt tgcactctca aaatcttca tcttcccatt      3780
cgctgtctgt atttctccat aactatatct ttcttcctct gtctccgccc acccacattt    3840
ttctcttcc ctttctctct ttggggaccc tcccccatgc tcccctgccc catcccctttt   3900
tccccttccc gtcttctcat ccctccattc ccatctttcc ccagcaatta ccagctctgg    3960
```

```
ctgggtcgcc acaacttgtt tgacgacgaa aacacagccc agtttgttca tgtcagtgag    4020
agcttcccac accctggctt caacatgagc ctcctggaga accacacccg ccaagcagac    4080
gaggactaca gccacgacct catgctgctc cgcctgacag agcctgctga taccatcaca    4140
gatgctgtga aggtcgtgga gttgcccacc gaggaacccg aagtggggag cacctgtttg    4200
gcttccggct ggggcagcat cgaaccagag aattgtatgt gggggcagac tgtgtagccc    4260
aaggcgggga tgggggactcc tgcgtccaag ggagaaaggg ccagggaagc aggtgaggtc    4320
gggctgcagc ccttttttctc ccgggttcgt agtctcattt ccagatgatc tccagtgtgt    4380
ggacctcaaa atcctgccta atgatgagtg caaaaaagcc cacgtccaga aggtgacaga    4440
cttcatgctg tgtgtcggac acctggaagg tggcaaagac acctgtgtgg tgaggcagcc    4500
ctgcccccag ggtctggaag ggctgaggga ggggactcag cctctgaact ggcttctgag    4560
agctaaccag gcatctgctt cactgcttcc cagctagctg tagccactcg ccccatcagt    4620
gccccagctc cccctccttc cccgcccat ccagggacaa ctgcatctca ccccccacac    4680
cagagttcac cgttcctcgt ggtaatgtgt tgttaccgtc gagtcagaga gtagtcctgg    4740
agaggtggcc tctgcgatgt gcccgcaggg gcagcgtcct gcagatggtc ctgcccctcc    4800
tccccctaac ctgtctgcag gcactgtcca cctggaccct gccccatgtg caggagctgg    4860
accctgaggt cccttccccc ttggccagga ctggagaccc tgtccctct gtgggaatcc    4920 ctgcccacct tcctctggga gtgggcactg gaggccctgt ctgcgagctg gggctcccca    4980
ggcagaactt gggccccgta gacctttctc actctcccct cccaccttgt gctcccaggg    5040
tgattcaggg ggcccgctga tgtgtgatgg tgtgctccaa ggtgtcacat catgggcta    5100 cgtcccttgt ggcaccccca ataagccttc tgtcgccgtc agagtgctgt cttatgtgaa    5160
gtggatcgag gacaccatag cggagaactc ctgaacgccc agccctgtcc cctaccccca    5220
gtaaaatcaa atgtgcatcc aatgtgtgtc acgttctgcc atcacctatc tttccagatg    5280
tggtgcacct ggaccactc ggctgaggct ggggccaccc cagctgtgtc aatctcatgc    5340
ctggaagtct gaggtcacca gcaggtgggg aaaggaaggg gctgtgacag gtgcagacaa    5400
acaggcaggg aaaggctcag atcccaaagg gcaagtcagg gacgccagaa cagttcactc    5460
acactaggat ggaccctgcc ctggtgggga ggtgggggc aatggaaggt ctgaggctga    5520
gaggttttat tgtggcgggg aagccagaaa aggtacagag ggatgttatt gcaagccatg    5580
ccttcccagg gaggggcccg ttctgcagaa gggtggagtt gcaccaaatg ctgggcggtg    5640
ctgtgtccac ctggggacaa gggtggacat cggagctgag gccggaactc cgggaaagaa    5700
gttccatgca gaccaccctg gctgggcacc aggggcaggg ccacacaaac tagccacact    5760
gccgagctca gcgggacgct ggacaagtgt ctgcagaacg ggagggatg ctgggcctct    5820 ggggtggagg tactgtgagg                                                5840
```

THERAPEUTIC USE OF AGONISTS OR ANTAGONISTS OF BRADYKININ RECEPTOR 1 OR 2, FOR MODULATION COLLATERAL BLOOD VESSEL GROWTH

This is the U.S. national stage of International application PCT/EP2011/002521, filed May 16, 2011 designating the United States and claiming priority to EP 10075199.9, filed May 14, 2010 and EP10075353.2, filed Aug. 18, 2010.

The present invention relates to bradykinin receptor modulators for use as a medicament for modulating collateral blood vessel growth of collateral arteries and/or other blood vessels of pre-existing arterial networks. The bradykinin receptor modulators are applicable in the treatment and/or prevention of disorders associated with defective blood flow. The bradykinin receptor agonist of the present invention is intended for use as a medicament for the prophylactic treatment (prevention) of cardiovascular ischemic disease in a patient at risk thereof. The invention further relates to a bradykinin receptor agonist for use in a method for treating a cardiovascular ischemic disease in a patient in need thereof, wherein said cardiovascular ischemic disease is a peripheral limb disease. The present invention further relates to a bradykinin receptor antagonist for use in a method for treating or preventing the formation of vessel malformation in a patient. Finally, the present invention relates to a pharmaceutical composition comprising one or more bradykinin receptor agonists(s) and/or one or more bradykinin receptor antagonists(s) and a pharmaceutical acceptable carrier.

BACKGROUND OF THE INVENTION

Figure 1:
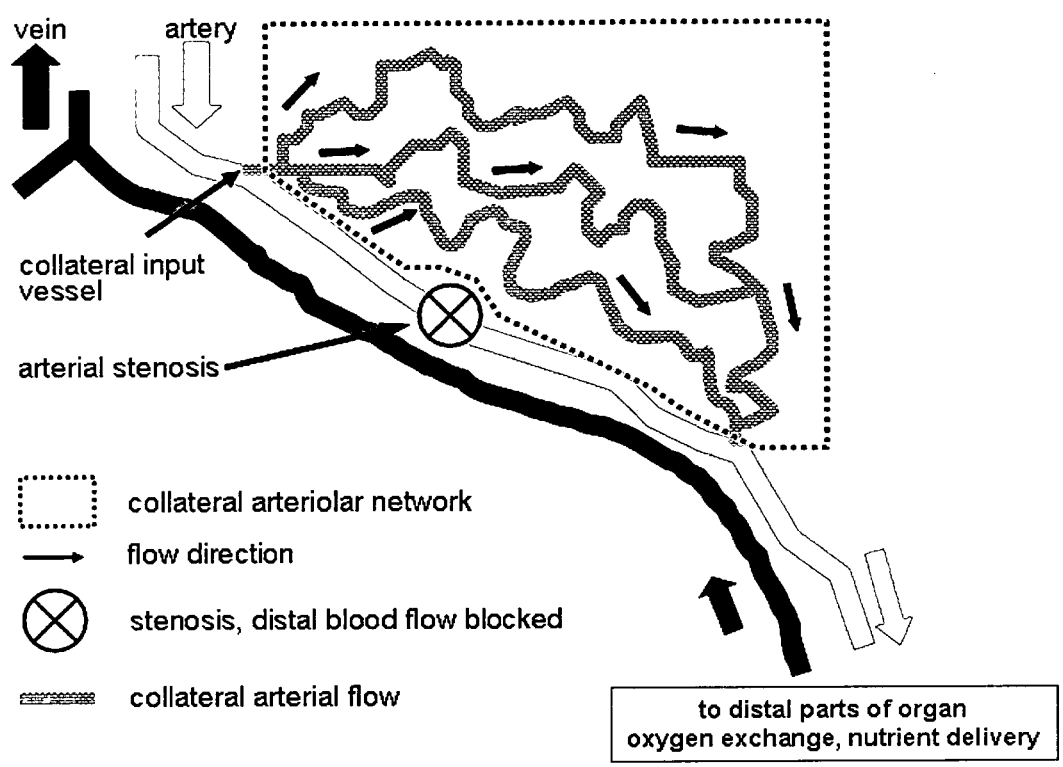

Arteriogenesis (collateral blood vessel growth) is the most important endogenous mechanism of compensation for an arterial stenosis or occlusion. The driving force is a pressure gradient, for example through a stenosis or an AV-shunt, which initiates an increased blood flow through the collateral arteries in the areas of hypoperfusion. Arteriogenesis is induced by flow, namely by an increased shear stress which act on endothelial cells. Diseases related to ischemic arterial blockage represent the most common cause of death in the western world (Lloyd-Jones, Adams et al. 2009). The most common causes of stenosis or occlusive diseases of the main arteries of the brain, the heart or the periphery are progressive atherosclerotic modifications of the blood vessels. The possibilities for treating such diseases are at the present time very limited, whereby the therapies on offer are often unsatisfactory (Schiele, Niehues et al. 2000). Angioplasty (balloon dilatations) and bypass operations are the only methods of treatment available in clinics at the present time. An angioplasty can however only be applied in a case of an arterial obstructive or occlusive disease (for example ischemic heart diseases) and as a consequence leads to an increased risk of a restenosis. Bypass surgeries are in any case only applicable for certain arterial obstructive or occlusive diseases and are associated with the disadvantage that an invasive intervention is necessary. New therapeutic strategies are therefore particularly relevant when considering how to treat and to avoid vascular obstructive or occlusive diseases. A pharmaceutical stimulation of arteriogenesis (the concept of growing a biological bypass) represents enormous therapeutic potential and a very promising method in treating or preventing arterial obstructive or occlusive diseases (Love 2003). The present invention therefore relates to the modulation of arteriogenesis and flow-induced collateral blood vessel growth (FIG. 1).

The vascular system is organized in a highly complex manner. In order to ensure the essential functions of distributing oxygen and nutrients, the vascular system is constantly undergoing reconstruction. The reconstruction of blood vessels differs between arteriogenesis on the one hand and angiogenesis on the other hand.

In the context of the present invention it is important to distinguish between arteriogenesis and angiogenesis. Angiogenesis relates to the outgrowth of new capillaries from previously existing vessels. This relates specifically to the growth of new vessels (capillary sprouting). The present invention does not relate to modulation of neo-vascularisation (such as angiogenesis) but rather to modulation of arteriogenesis.

The diameter of an artery is actively increased in arteriogenesis. This mechanism does not deal with a passive dilatation, rather an active reconstruction of the vessel including the degradation of the extracellular matrix and a proliferation of artery cells (endothelial cells and smooth muscle cells), in order to achieve the required structure for a larger artery. The end result of arteriogenesis is that a pre-existent small artery grows into a large functional conductance artery. The initial stimulus for arteriogenesis is a change in the shear stress of the endothelial layer (not ischemia), which occurs through an increase in the blood flow through an artery.

It is therefore important to note that the present invention relates to arteriogenesis, the mechanism of which is fundamentally different from the mechanism of angiogenesis (Schaper 2009).

Previous studies have focused on the investigation of angiogenesis, whereby VEGF has been identified as a major regulator. Previous studies on rabbits, in which the femoral artery has been removed, show that under these hypoxic conditions VEGF is strongly up-regulated (Takeshita, Zheng et al. 1994). Additional application of the specific endothelial mitogen VEGF can stimulate artery growth. Such studies however do not distinguish between the outgrowth of capillaries (angiogenesis) and the mechanism related to the collateral growth of arteries (arteriogenesis). Angiogenesis occurs directly in the ischemic area and hypoxic conditions lead to the local production of VEGF. VEGF functions primarily as a mitogen for endothelial cells. However, arteriogenesis requires the reconstruction of endothelial cells, smooth muscles cells and a highly regulated end complex reconstruction of the extracellular matrix. In the case of an arterial obstructive or occlusive condition angiogenesis alone does not lead to a significant improvement in perfusion (Zadeh and Guha 2003, Storkebaum and Carmeliet 2004, Wang, Killic et al. 2005).

B1-receptor agonists are also known for modulating angiogenesis (Emaueli, Circulation, 2002), although only in relation to the outgrowth of capillaries (angiogenesis) and not in relation to modulation of the growth of collateral arteries (arteriogenesis).

In addition to flow-induced reconstruction, the migration of leucocytes plays a decisive role in arteriogenesis. Leucocytes, especially monocytes, produce inflammatory cytokines and growth factors, which are of significant importance for the remodeling of an artery. Such a remodeling leads to the enlargement of an arteriole into an artery with an outward growth of the artery lumen (positive outward remodeling). Arteriogenesis is therefore the most important endogenous compensatory mechanism for the maintenance of a stable blood flow in the case of a stenosis (mechanism of a biological bypass, FIG. 1). Arteriogenesis however generally does not occur in the ischemic region but rather in regions proximal to the occlusion and therefore effects the bypass circulation which provides blood supply to the distal hypoperfusion area (FIG. 1) (Pipp, Heil et al. 2003).

Figure 2A:
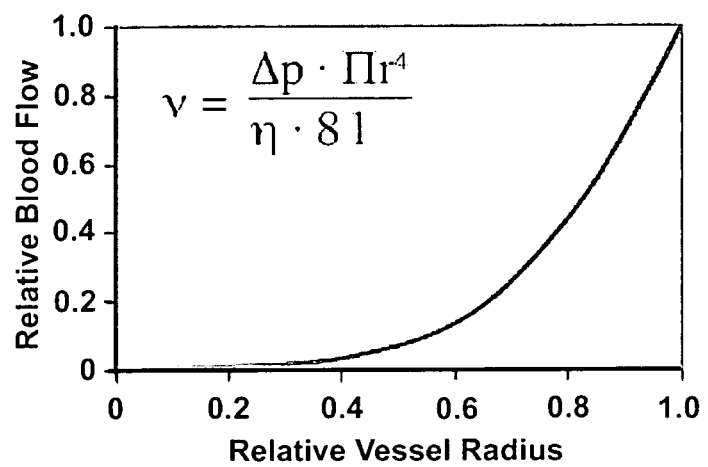
Figure 2B:
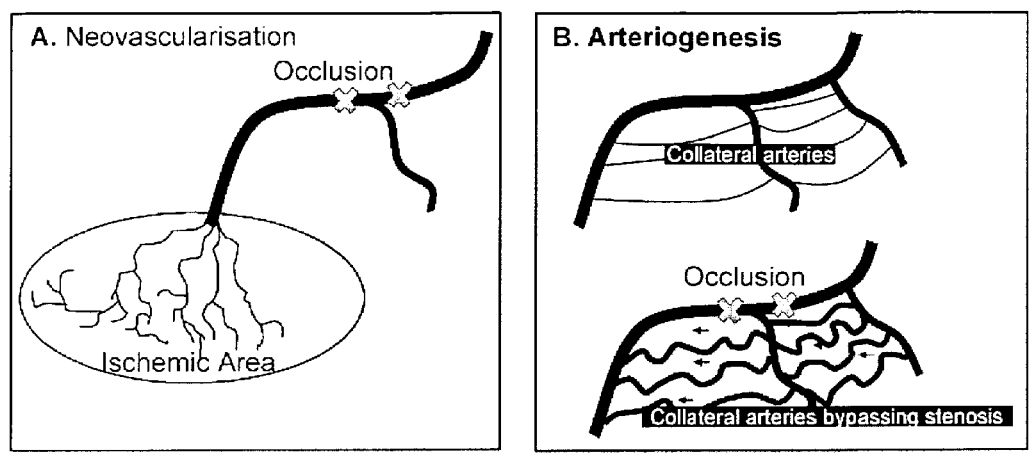

A schematic curve demonstrates the biological importance of arteriogenesis (FIG. 2a). Angiogenesis produces many new capillaries with a small diameter where as arteriogenesis enlarges the diameter of already existing arteries (FIG. 2b). The Hagen-Poiseuille rule demonstrates the relationship between blood flow and artery diameter and shows that the blood flow is enhanced by an exponential factor of 4 in relationship to the radius (FIG. 2b). According to this rule a minimal change in artery radius leads to significant improvements in perfusion. Comparable improvements in perfusion can not be achieved through the growth of many new small capillaries, as is the case in angiogenesis.

Previous studies have shown that collateral artery growth can be stimulated by an increase in blood flow (specifically an increase in the shear stress of the endothelial cells) or through the application of cytokines such as a GM-CSF (Buschmann, Busch et al. 2003). In a stroke or apoplexy model in the rat is has been shown that stimulation of arteriogenesis via the application of GM-CSF leads to an increase of the haemodynamic reserves of the brain (Schneeloch, Mies et al. 2004). Through the application of GM-CSF the ischemic region in an experimentally induced stroke could be significantly reduced. The stimulation of arteriogenesis is therefore an effective strategy for the treatment and/or prevention of ischemic obstructive or occlusive conditions, in addition to heart attacks and strokes.

Factors such as GM-CSF have been tested for their therapeutic stimulation of arteriogenesis (van Royen, Schirmer et al. 2005). The bradykinin signaling pathway has however not been examined in the prior art for its role in arteriogenesis, although its function as a vasodilator (antagonist of the Renin-angiotensin system) and its stimulatory effect in neo-vascularisation (Emanueli, Bonaria Salis et al. 2002) is known.

Bradykinin receptor 1 (B1R) and bradykinin receptor 2 (B2R) belong to the kallikrein-kinin system (KKS), which also contains the proteins kallikrein and kininogen. Kininogen is a substrate of the KKS and is enzymatically cleaved by kallikrein, through which a number of kinins are released.

Figure 3:
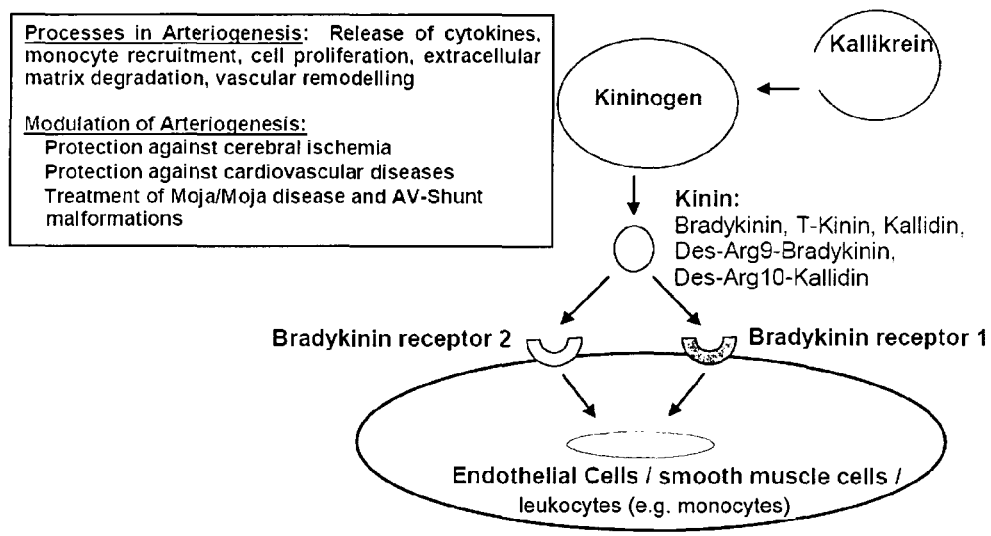

Bradykinin, T-kinin and kallidin all belong to the kinin group. These proteins can be digested at their C terminus by a carboxypeptidase and can therefore be transformed to Des-Arg$^9$-bradykinin and Des-Arg$^{10}$-kallidin. Bradykinin, T-kinin and kallidin impart their signaling effect via the B2-receptor and Des-Arg$^9$-bradykinin and Des-Arg$^{10}$-kallidin via the B1-receptor (FIG. 3). All components of the kallikrein-kinin system can be produced in the artery wall. The bradykinin receptors in the artery walls can be expressed in either the endothelial cells, the smooth muscle cells or in leucocytes. A signaling effect via the bradykinin-receptors leads to vasodilatation, cell proliferation, inflammation and the production of various cytokines.

The effect of B1R and B2R agonists and antagonists on angiogenesis, which is the formation of new blood vessels, has been disclosed in the prior art. The relationship between angiogenesis and the bradykinin signaling pathway has also been investigated (Stone et al., 2009). It is known that treatment with agonistic substances of B1R and B2R leads to the promotion of angiogenesis and the formation of new vessels (WO 02/17958 A1). B1R and B2R antagonists have also been used for treating cerebral ischemic injury, arteriosclerosis, pain and inflammation (WO 98/06417, EP 0623350 A1, WO 2006/071775 A2).

Agonists of the B1R (such as increased B1R expression, peptides and various chemical derivatives of heterocyclic compounds) have been disclosed that may be useful in treatment of stroke patients, hypertension or heart failure (DE 10115668 A1, U.S. Pat. No. 6,015,818, WO 2004/069857).

Despite the extensive prior art surrounding the Bradykinin receptors and their role in angiogenesis, until the present time there has been no knowledge that connects Bradykinin receptor 1 (B1R) or bradykinin receptor 2 (B2R) with arteriogenesis.

Patients in need of stimulated or enhanced arteriogenesis, or patients who are at risk of suffering from disorders associated with an increased need for enhanced arteriogenesis, have long suffered through the lack of effective medicaments that target arteriogenesis. Similarly, patients with blood vessel malformation have been without effective treatment options, considering that until now no medicaments were known that could effectively reduce arteriogenesis in those patients where such treatment would be beneficial.

The pharmaceutical stimulation of arteriogenesis has previously been identified as exhibiting therapeutic potential and is a promising option for treating or preventing arterial obstructive or occlusive diseases or other conditions or disorders associated with defective blood flow (Love 2003). Despite this need, until now effective products and methods for modulating arteriogenesis were unknown.

SUMMARY OF THE INVENTION

In light of the prior art the technical problem underlying the present invention is to provide effective substances, methods and related medicaments for modulating collateral vessel growth (arteriogenesis), so that collateral artery growth can be either activated or inhibited depending on the patients needs.

This problem is solved by the features of the independent claims. Preferred embodiments of the present invention are provided by the dependent claims.

The invention therefore relates to bradykinin receptor modulators for use as a medicament for modulating collateral blood vessel growth of collateral arteries and/or other blood vessels of pre-existing arterial networks.

The invention also relates to one or more bradykinin receptor modulators for use as a medicament for modulating collateral blood vessel growth of collateral arteries and/or other blood vessels of pre-existing arterial networks in the treatment and/or prevention of disorders associated with defective blood flow.

The bradykinin receptor modulator according to any one of the preceding claims, wherein said bradykinin receptor modulator is a bradykinin receptor 1 (B1R) and/or a bradykinin receptor 2 (B2R) modulator.

In a preferred embodiment the bradykinin receptor modulator of the present invention is a bradykinin receptor agonist.

In a preferred embodiment the bradykinin receptor agonist of the present invention is for use as a medicament for the prophylactic treatment (prevention) of cardiovascular ischemic disease in a patient at risk thereof.

In relation to the prevention of cardiovascular ischemic disease in a patient at risk thereof, the cardiovascular ischemic disease is (a) cerebral ischemia, in particular stroke, vascular dementia and/or infarct dementia;

(b) myocardial ischemia, in particular a coronary heart disease and/or myocardial infarction; and/or (c) peripheral limb disease, in particular periphery arterial occlusive disease.

In relation to the prevention of cardiovascular ischemic disease in a patient at risk thereof, the patient (a) shows symptoms of being at risk of developing a cardiovascular ischemic disease;

(b) shows any risk markers in ex vivo tests, in particular in blood samples;

(c) has previously had a cerebral or myocardial ischemia; and/or (d) has a predisposition of developing a cardiovascular ischemic disease, in particular a genetic predisposition.

In another embodiment the bradykinin receptor agonist of the present invention for prevention of cardiovascular ischemic disease is defined in that said symptoms of (a) are selected from the group comprising of neurological malfunctions, transitory ischemic attack, congestive heart failure, angina pectoris, valvular heart disease, cardiomyopathy, pericardial disease, congenital heart disease, coarctation, atrial and/or ventricular septal defects and/or preferably combinations of two and more thereof.

The bradykinin receptor agonist of the present invention for prevention of cardiovascular ischemic disease can be further defined in that said patient at risk further exhibits one or more of the following conditions:

sclerosis, in particular atherosclerosis and/or transplantation-induced sclerosis; a cerebral occlusive disease, renal occlusive disease, a mesenterial artery insufficiency or an ophthalmic or retinal occlusion, post-operative or post-traumatic condition; thrombosis; embolism; restenosis, in particular primary restenosis, secondary restenosis and/or in-stent restenosis; trisomy 21; hypoglycemia; tachycardia; aneurysm; vasculitis; preeclampsia; placental hypoxia; sleep apnea; sexual dysfunction, in particular erectile dysfunction or female sexual dysfunction; post-operative hypoxia; Raynaud's disease; endothelial dysfunction; cancer; renal failure; varicose veins; edema, in particular venous edema and/or lymphedema; hypotension; decubitus; carbon monoxide poisoning; heavy metal poisoning; ulcers; sudden infant death syndrome; erythroblastosis; asthma; chronic obstructive pulmonary disease; sickle cell disease; induced g-forces which restrict the blood flow and force the blood to the extremities of the body; localized extreme cold, in particular frost bite; tourniquet application; an increased level of glutamate receptor stimulation or for any disease where atherosclerosic plaques in the vascular wall lead to an obstruction of the vessel diameter.

The bradykinin receptor agonist of the present invention for prevention of cardiovascular ischemic disease can be further defined in that said patient previously had been exposed to or is going to be exposed to (a) a pharmaceutical or medical treatment damaging one or more arteries;

(b) a radiation treatment damaging one or more arteries; or (c) a surgical treatment damaging one or more arteries.

The bradykinin receptor agonist of the present invention can also be further defined in that said patient is tested for arteriogenesis.

The bradykinin receptor agonist of the present invention can be further defined in that said bradykinin receptor agonist is administered in a long-term application.

In a preferred embodiment the bradykinin receptor agonist is administered to the patient for at least one week, at least two weeks, at least three weeks, at least four weeks, at least one month, at least two months, at least three months, at least four months, at least five months, at least six months, at least seven months, at least eight months, at least nine months, at least ten months, at least eleven months, at least one year, at least two years, at least three years or enduringly.

In a preferred embodiment the bradykinin receptor agonist of the present invention is selected from the group comprising of Sar-[D-Phe8]-des-Arg9-bradykinin (R838);
Lys-(Des-Arg9)-bradykinin;
T-kinin;
kallidin;
des-Arg9-bradykinin;
des-Arg10-kallidin;
4-(2-pyridylmethoxy)-substituted quinoline (FR190997);
3-(2-pyridylmethyl)-substituted benzimidazole (FR191413);
Bradykinin;
bradykinin/H1970;
kallidin/Lys-bradykinin/H2180;
SarLys[Hyp3,Cha5,D-Phe8]desArg9-bradykinin;
SarLys[Hyp3,Igl5,D-Phe8]desArg9-bradykinin;
SarLys[Hyp3,Cpg5,D-Phe8]desArg9-bradykinin;
RMP-7 iobradamil/cereport;
JMV1116 and analogues;
Ile-Ser-bradykinin (B1643);
[Phe8-(ψ-CH2NH)-Arg9]-bradykinin;
[Hyp3,Tyr(Me)8]-bradykinin;
[Hyp3]-bradykinin (B7775);
a nucleic acid molecule coding for a bradykinin receptor or a bradykinin receptor agonist;
an agent increasing the concentration or the half-life of a bradykinin receptor agonist;
an agonistic bradykinin antibody; and
a combination of two or more thereof.

In another embodiment the bradykinin receptor agonist of the present invention is selected from the group comprising of R838, T-kinin, kallidin, des-Arg9-bradykinin, des-Arg10-kallidin, FR190997, FR191413, a nucleic acid molecule coding for a bradykinin receptor and a bradykinin receptor agonist, together with an agent increasing the concentration or the half-life of the bradykinin receptor agonist, in particular wherein said bradykinin receptor agonist is R838, T-kinin and/or kallidin.

In another embodiment the bradykinin receptor agonist of the present invention is deoxyribonucleic acid (DNA), ribonucleic acid (RNA) or a nucleic acid analogue.

In another embodiment the bradykinin receptor agonist of the present invention the deoxyribonucleic acid (DNA), ribonucleic acid (RNA) or a nucleic acid analogue is comprised in a vector, preferably, a viral vector or a plasmid.

In a preferred embodiment the agent increasing the concentration or the half-life of a bradykinin receptor agonist is an enzyme inhibitor, in particular a peptidase inhibitor.

In another embodiment the enzyme inhibitor is an angiotensin-converting enzyme (ACE) inhibitor, an amino peptidase P (APP) inhibitor and/or a carboxypeptidase N(CPN) inhibitor.

In another embodiment the ACE inhibitor is selected from the group consisting of ramipril, quinapril, cilazapril, spirapril-HCl 1H2O, catopril, enalaprilmaleat, lisinopril, perindopril-erbumin, trandolapril, fosinopril-sodium and/or a combination of two or more thereof.

In another embodiment of the present invention the bradykinin receptor agonist further induces migration of leukocyte cells and/or leucocyte precursor cells.

A further aspect of the present invention relates to a bradykinin receptor agonist used for treatment of cardiovascular ischemic disease in a patient in need thereof, wherein said cardiovascular ischemic disease is a peripheral limb disease, in particular periphery arterial occlusive disease.

A further aspect of the bradykinin receptor modulator of the present invention is a bradykinin receptor antagonist for treatment and/or prevention of blood vessel malformation in a patient.

In another embodiment the patient previously had been exposed to or is going to be exposed to
 (a) a pharmaceutical or medical treatment damaging one or more arteries;
 (b) a radiation treatment damaging one or more arteries; or
 (c) a surgical treatment damaging one or more arteries.

In another embodiment the bradykinin receptor antagonist is used in a method for treating a patient suffering from the Moja Moja Syndrome.

The bradykinin receptor antagonists of the present invention may also be administered in a long-term application.

An example of such long term application is that the bradykinin receptor antagonist is administrated to the patient for at least one week, at least two weeks, at least three weeks, at least four weeks, at least one month, at least two months, at least three months, at least four months, at least five months, at least six months, at least seven months, at least eight months, at least nine months, at least ten months, at least eleven months, at least one year, at least two years, at least three years or enduringly.

The bradykinin receptor antagonist of the present invention is in a preferred embodiment selected from the group consisting of
 icatibant (HOE140, H157);
 CP0597;
 D-Arg[Hyp3,Thi5,HypE(trans-propyl)7,Oic8]-bradykinin (NPC17731);
 (des-Arg9,Leu8)-bradykinin;
 AC-Lys-Arg-Pro-Pro-Gly-Phe-Ser-D☐Nal-lie (R715);
 AC-Lys-Arg-Pro-Pro-Gly-(☐Me)Phe-Ser-D☐Nal-lie (R892);
 [Leu8,des-Arg9]-bradykinin;
 [Leu9,des-Arg10]-kallidin (CP0298);
 [des-Arg10]-HOE140;
 Lys-[Leu8,des-Arg9]-bradykinin;
 H-Lys-Lys-Arg-Pro-Hyp-Gly-Igl-Ser-D-Igl-Oic-OH (B9858);
 H-D-Arg-Arg-Pro-Hyp-Gly-Igl-Ser-D-Igl-Oic-Arg-OH (B9430);
 FR167344;
 FR173657;
 WIN6433;
 bradyzide;
 a nucleic acid molecule inhibiting the formation of an intrinsic bradykinin receptor agonist or a bradykinin receptor;
 an inhibitory bradykinin antibody; and
 a combination of two or more thereof.

In another embodiment of the present invention the bradykinin receptor antagonist is selected from the group consisting of HOE140, CP0597, NPC17731, FR167344; FR173657; a nucleic acid molecule inhibiting the formation of an intrinsic bradykinin receptor agonist or a bradykinin receptor and/or a combination of two or more thereof.

In another embodiment the nucleic acid molecule is an siRNA, microRNA or a nucleic acid analogue.

In another embodiment the bradykinin receptor antagonist is comprised in a vector, preferably, a viral vector or a plasmid.

The invention also relates to bradykinin receptor antagonists that are intrinsic bradykinin receptor antagonists or functional analogues thereof.

A further aspect of the invention relates to a pharmaceutical composition comprising one or more bradykinin receptor agonists as described herein and a pharmaceutically acceptable carrier for treatment and/or prevention of cardiovascular ischemic disease in a patient exhibiting the disease or in a patient at risk thereof.

A further aspect of the invention relates to a pharmaceutical composition comprising one or more bradykinin receptor antagonists as described herein and a pharmaceutical acceptable carrier for treatment and/or prevention of blood vessel malformation in a patient exhibiting the disease or in a patient at risk thereof.

In another embodiment the pharmaceutical composition further comprises of one or more other compounds selected from the group consisting of
 (a) one or more colony stimulating factor(s) (CSF(s));
 (b) one or more eicosanoid(s), in particular one or more prostaglandin(s).

The invention further relates to a method for modulating collateral vessel growth (arteriogenesis) by the inhibition or stimulation of the bradykinin receptor 1 (B1R) and/or the bradykinin receptor 2 (B2R). In one embodiment the method of the present invention is characterized in that the modulation of the collateral vessel growth occurs via the modulation of collateral arteries from existing arterial networks, preferably by modulation of arterial radius.

In one embodiment the method of the present invention is characterized in that the modulation, such as an induction or a reduction, of the collateral vessel growth occurs through the stimulation (using an agonist) or the inhibition (using an antagonist) of the bradykinin receptor 1 and/or bradykinin receptor 2, preferably in the vessel wall by modulation of the bradykinin receptors of the endothelial cells, the smooth muscle cells and/or leucocytes that have migrated into the vessel wall. In one embodiment the method of the present invention is characterized in that the induction of the collateral vessel growth (arteriogenesis) occurs by stimulation of the bradykinin receptor.

The invention also relates to a method for enhancing collateral artery growth with kinins or other bradykinin receptor agonists. A further aspect of the present invention is characterized in that the inhibition of collateral vessel growth (arteriogenesis) occurs by inhibition of the bradykinin receptor.

The invention further relates to a method as described above, characterized in that the modulation of the collateral vessel growth occurs by means of nucleic acid molecules, preferably through nucleic acids (such as siRNA or microRNA) with complementarity to mRNA of components of the kallikrein-kinin system (for example kininogen, BR1 and/or BR2).

The invention further relates to a method as described herein, characterized in that the bradykinin receptor pathway stimulation is enhanced by bradykinin augmentation as a consequence of ACE inhibitor activity.

A further aspect of the present invention relates to a bradykinin receptor 1 (B1R) and/or bradykinin receptor 2 (B2R) inhibiting substance for use as a medicament to inhibit collateral vessel growth. A further embodiment of the present invention relates to a bradykinin receptor 1 (B1R)

and/or bradykinin receptor 2 (B2R) stimulating substance for use as a medicament to stimulate collateral vessel growth.

The bradykinin receptor 1 (B1R) and/or bradykinin receptor 2 (B2R) stimulating substance of the present invention can be used as a medicament for the prevention and/or treatment of circulatory disorders, arterial conditions and/or ischemic obstructive or occlusive conditions or stroke, preferably coronary heart disease or peripheral obstructive disease, preferably via stimulation of the bradykinin signaling pathways. A further aspect of the invention relates to a pharmaceutical composition comprising at least one bradykinin receptor 1 and/or bradykinin receptor 2 modulating substance with a pharmaceutically acceptable carrier.

The invention also relates to the use of a bradykinin receptor 1 (B1R) and/or bradykinin receptor 2 (B2R) stimulating substance for the manufacture of a medicament to prevent and/or treat circulatory disorders, arterial diseases and/or ischemic obstructive or occlusive conditions or strokes, preferably coronary heart diseases or peripheral arterial obstructive diseases, preferably by a stimulation of the bradykinin signaling pathways. A further aspect of the invention relates to a method for the therapeutic or prophylactic treatment of circulatory disorders, arterial diseases and/or ischemic obstructive or occlusive conditions or strokes, preferably coronary heart diseases or peripheral arterial obstructive diseases, characterized in that a therapeutically effective amount of a bradykinin receptor 1 (B1R) and/or bradykinin receptor 2 (B2R) stimulating substance is administered to a mammalian patient.

DETAILED DESCRIPTION OF THE INVENTION

It is important to note that a stimulation of angiogenesis (neovascularisation) or a vasodilatation does not lead to a preventative treatment for patients with progressive constriction of blood vessels or arteries (for example as it is the case in atherosclerosis). Furthermore, a stimulation of angiogenesis can not sufficiently compensate for an endogenous stenosis in a major artery (see above prior art comparing angiogenesis and arteriogenesis). Similarly dilatation to its maximum extent cannot compensate for an endogenous stenosis in a major artery, as the hemodynamic reserves become very quickly exhausted when collateral vessels or arteries do not sufficiently grow in their diameter through arteriogenesis.

However, the activation or stimulation of arteriogenesis enables the preventative treatment of cardiovascular disease. This represents one surprising and beneficial aspect of the invention. Without being able to modulate the arteriogenesis, there has been until now no way of preventing blood flow restriction in patients at risk. The modulation of arteriogenesis, in contrast to angiogenesis, enables the treatment (or prevention) of restricted blood flow in new groups of patients, in comparison to what was previously possible in the prior art. The targeted modulation of arteriogenesis allows patients to be treated who were previously without appropriate or sufficient preventative or therapeutic options. The modulation of angiogenesis is simply not sufficient in providing effective relief or prevention of restricted blood flow. Although angiogenesis can be initiated quickly, the physiological effect of modulated, for example enhanced, angiogenesis is simply insufficient to provide beneficial therapeutic or preventative effects in patients (see FIG. 2b). For example diabetes patients with problems related to blood flow in their feet and other extremities could not be treated using the substances of the prior art that targeted enhanced angiogenesis. However, by targeting arteriogenesis a more effective therapeutic and preventative change is observed physiologically, allowing sufficient increases in blood flow via increased vessel diameter that prove significantly valuable to the patient.

The enablement of treating or prophylactically treating new groups of patients represents a significant and unexpected advance over the prior art. The use of bradykinin receptor modulators, particularly agonists, relates to a new use of known substances that provides new perspectives and therapeutic options for doctors when assessing patients with blood flow disorders. The substances of the present invention can also be administered in a preventative manner, something which was previously unknown and impracticable in the context of angiogenesis.

Basically cardiovascular ischemic diseases which occur due to the occlusion of a conductance artery can be prevented or treated by stimulation of arteriogenesis, but not due to stimulation of angiogenesis.

In most cases obstruction of conductance vessels occurs slowly, which results in the recruitment of the collateral artery network outside the ischemic region in oxygen-rich tissue that bypass the site of occlusion. Subsequent collateral arteries grow due to the driving force of blood flow induced shear stress, which leads to the expression of the components of the kinin-bradykinin receptor signaling pathway locally in the collateral network. Stimulation of arteriogenesis increases vessel diameter of the bypassing arteries, which produces a new functional conductance vessel to supply the endangered territory with blood. Increasing the number of capillaries within the ischemic region cannot significantly increase blood flow when its limiting structure lies upstream (FIG. 2b).

Furthermore, according to the law of Hagen-Poiseuille, perfusion v is mainly determined by the vessel radius r to the power of 4. Thus, only minimal changes in vessel diameter of a pre-existent arteriol lead to a big difference of the perfusion level (arteriogenesis). All other factors like viscosity $\eta$, pressure differences $\Delta P$, and distance differences (vessel length) $\Delta l$ as well as flow volume V are still proportional according to the equation. In conclusion, newly formed small vessels cannot compensate for the loss of a main supplying arterial vessel (angiogenesis). This basic physiological principle has been shown in a number of clinical trials, where therapeutically induced angiogenesis has led to a significant increase in capillary density, but without significant beneficial effects on tissue perfusion (Zadeh and Guha 2003; Storkebaum and Carmeliet 2004; Wang, Kilic et al. 2005). In contrast, adaptive proliferation of collateral vessels (arteriogenesis) represents the most important physiological protection mechanism against arterial stenosis (Carmeliet 2000).

It was until now unknown that bradykinin receptor modulators, especially agonists of the B1R, were capable of modulating arteriogenesis in a manner suitable for prophylactic or therapeutic application. Due to the fundamental differences between arteriogenesis and angiogenesis, new groups of patients with different sets of existing illnesses or risk factors may be treated, either therapeutically or prophylactically, with the bradykinin receptor modulators of the present invention.

As used throughout the invention, the term "bradykinin receptor" may be understood as any receptor that is selectively triggered by bradykinin. Presently, there are two bradykinin receptors known in the art, i.e., bradykinin receptor 1 (B1 receptor) and/or bradykinin receptor 2 (B2 receptor). The bradykinin receptor 2 is consecutively and permanently expressed, whereas the B1 receptor is only expressed when the cells are subjected any stress, such as, e.g., inflammation, a physical injury or trauma. The bradykinin receptor 1 may also play a role in the context of chronic pain.

It will be understood by a person skilled in the art that the terms "bradykinin receptor 1" and "bradykinin receptor 2" may refer to the naturally occurring receptors but may also refer to functional mutated forms thereof.

The term "bradykinin receptor 1" refers to a protein having the sequence of SEQ ID NO:1 or a sequence which has a sequence homology of at least 70%, preferably of at least 80%, more preferably of at least 85%, even more preferably of at least 90%, even more preferably of at least 95%, and most preferably of 100% of the wildtype protein of SEQ ID NO:1.

The term "bradykinin receptor 2" refers to a protein having the sequence of SEQ ID NO:2 or a sequence which has a sequence homology of at least 70%, preferably of at least 80%, more preferably of at least 85%, even more preferably of at least 90%, even more preferably of at least 95%, and most preferably of 100% of the wildtype protein of SEQ ID NO:2.

The term "functional" as used in this context refers to a protein that has at least 25%, preferably at least 50%, more preferable at least 75%, even more preferable at least 80%, even more preferable at least 85%, even more preferable at least 90%, even more preferable at least 95% and most preferably 100% or even more of the activity compared to the wildtype protein.

It will further be understood that that the receptors may be subjected to one or more posttranslational modifications. Therefore, the receptors may be, e.g., lipidated, phosphorylated, sulfated, cyclized, oxidated, reduced, decarboxylated, acetylated, acylated, amidated, deamidated, biotinylated or bound to one or more small molecule(s) and/or terpene(s). Further, the bradykinin receptor agonist may or may not form one or more intramolecular disulfide bond(s) and/or one or more intermolecular disulfide bond(s).

Further, the protein may be optionally truncated or elongated by one, two, three, four, five, up to ten, up to twenty, up to thirty, up to fifty or even more than fifty amino acid residues.

As used in the context of the present invention the term "bradykinin receptor modulator" may be understood in the broadest sense as any compound that can directly or indirectly modulate, for example stimulate or inhibit, the function of the bradykinin receptor and/or the signal transduction cascade related to a bradykinin receptor. Modulators therefore encompass both agonists and antagonists of the bradykinin receptor(s).

As used in the context of the present invention, the term "bradykinin receptor agonist" may be understood in the broadest sense as any compound that can directly or indirectly stimulate the signal transduction cascade related to a bradykinin receptor. The bradykinin receptor agonist may be, e.g., a peptide, a kinin precursor, a non-peptide agonist, a nucleic acid molecule encoding a kinin, a kinin precursor, or another bradykinin receptor agonist, or a compound inhibiting the degradation of any other bradykinin receptor agonist. Bradykinin receptor molecules themselves also fall under this definition, considering that over-expression or application of the bradykinin receptors themselves may lead to enhanced bradykinin receptor activity due to increased presence, e.g. cellular concentration of the receptors, so that the effect on Bradykinin signaling is enhanced by application or admission of additional molecules of the receptors themselves.

Most preferably, the bradykinin receptor agonist is a peptide or a peptidomimetic, in particular a nonapeptide or a decapeptide. Exemplarily, the peptidic bradykinin receptor agonist is bradykinin or a functional derivative thereof, a kinin precursor or a functional derivative thereof, kallidin or a functional derivative thereof.

As used in the context of the present invention, the term "bradykinin" refers to a peptide of the sequence H-Arg-Pro-Pro-Gly-Phe-Ser-Pro-Phe-Arg-OH (SEQ ID NO:3). The term "kallidin" refers to a peptide of the sequence H-Lys-Arg-Pro-Pro-Gly-Phe-Ser-Pro-Phe-Arg-OH (SEQ ID NO:4). Bradykinin and kallidin are also designated as kinins.

In the context of the peptides bradykinin and kallidin, a functional derivative thereof may exemplarily be any protein or peptide that comprises the sequence of bradykinin. Therefore, one, two, three, four, five, six, seven, eight, nine, ten, up to 15, up to 20, up to 30, up to 40, up to 50, up to 100 or even more amino acids may be added to the amino or the carboxy terminus of said peptide.

Exemplarily, a functional peptide derivative may be Met-Lys-bradykinin bearing the sequence H-Met-Lys-Arg-Pro-Pro-Gly-Phe-Ser-Pro-Phe-Arg-OH (SEQ ID NO:5) or Ile-Ser-bradykinin bearing the sequence H-Ile-Ser-Arg-Pro-Pro-Gly-Phe-Ser-Pro-Phe-Arg-OH (SEQ ID NO:6). Ile-Ser-bradykinin is also designated as T-kinin.

Alternatively or additionally, the peptides bradykinin and kallidin, respectively, may be truncated by one or two amino acids at their amino or their carboxy terminus. Exemplarily, truncated bradykinin may be des-Arg9-bradykinin bearing the amino acid sequence H-Arg-Pro-Pro-Gly-Phe-Ser-Pro-Phe-OH (SEQ ID NO:7), des-Arg10-kallidin bearing the amino acid sequence H-Lys-Arg-Pro-Pro-Gly-Phe-Ser-Pro-Phe-OH (SEQ ID NO:8), or Sar-[D-phe8]-des-Arg9-bradykinin (wherein Sar refers to a N-methylglycyl residue (aka sarcosine) and D-Phe refers to the D-amino acid phenylalanine).

Further, alternatively or additionally, one, two or even three amino acid residues may be replaced by other amino acid residues. These amino acid residues may be natural amino acid residues or non-natural amino acids. Moreover, alternatively or additionally, one, two or even three amino acid residues may be inserted into the sequence of said peptides, wherein these amino acid residues may be natural amino acid residues or non-natural amino acids.

Optionally, the bradykinin receptor agonist, in particular when it is a peptide, may be lipidated, phosphorylated, sulfated, cyclized, oxidated, reduced, decarboxylated, acetylated, acylated, amidated, deamidated, biotinylated or bound to one or more other small molecule(s) and/or terpene(s). Further, the bradykinin receptor agonist may or may not form one or more intramolecular disulfide bond(s) and/or one or more intermolecular disulfide bond(s). The bradykinin receptor agonist, in particular when it is a peptide, may also be conjugated or non-covalently associated to molecular structures that may facilitate uptake such as, e.g., positively charged polymers (e.g., polyethylene imine (PEI)), neutral lipids, positively charged lipids, viral vectors, liposomes, micro- and/or nanobeads, cell-penetrating peptides (=protein-transduction domains, e.g., polyarginines (e.g., R8, R9, R10), HIV Tat peptide, antennapedia/penetratin peptide, a Lactoferrin-derived peptide), antimicrobial peptides and/or a Chariot peptide.

Preferably, the peptide bears a free amino terminus and a free carboxy terminus or may have a blocked amino terminus and/or carboxy terminus. Exemplarily, the amino terminus may be acylated or acetylated and/or the carboxy terminus may be amidated.

Preferably, the peptide consists of natural L-amino acids. However, the peptide may also comprise one or more non-natural amino acid(s) such as, e.g., D-amino acid(s), beta amino acid(s), methylated amino acid(s) (e.g., N-methylated amino acid(s)). The peptide may even only consist of non-natural amino acids. The peptide may also be a retro-inverso peptide, thus, a peptide mainly comprising D-amino acids and a reverse amino acid sequence compared to the corresponding peptide mainly comprising L-amino acids. Many bradykinin receptor agonists, such as, e.g., the kinins bradykinin and kallidin, are inactivated by proteolytic cleavage, in particular proteolytic cleavage of the one, two or three C-terminal amino acid(s). Therefore, preferably, one or more amino acid(s) near the carboxy terminus, such as, e.g., the phenylalanine at position 8 (Phe8), may be replaced by one or more non-natural amino acid residue(s). Exemplarily, the peptide is the D-amino acid-containing peptide Sar-[D-phe8]-des-Arg9-bradykinin.

The bradykinin receptor agonist may also be a kinin precursor. As used herein, the term "precursor" may be understood in the broadest sense as any molecular structure that can be converted into a functional kinin peptide by metabolism. Typically, a kinin precursor is a longer polypeptide chain that is cleaved into the respective functional kinin peptide by proteolytic cleavage. Herein, the terms "proteolytic cleavage" and "peptidolytic cleavage" may be understood interchangeably. A bradykinin precursor may be, e.g., a kininogen cleavable by the protease kallikrein or kallikrein-like enzymes. Exemplarily, a kinin precursor is KNG1 kininogen 1 (also designated as BDK; KNG; KNG1).

The bradykinin receptor agonist may also be a non-peptide agonist such as, e.g., 4-(2-pyridylmethoxy)-substituted quinoline (FR190997); 3-(2-pyridylmethyl)-substituted benzimidazole (FR191413).

The bradykinin receptor agonist may also be a nucleic acid molecule encoding a kinin or a kinin precursor, a bradykinin receptor or another bradykinin receptor agonist.

Exemplarily, a nucleic acid may be a nucleic acid molecule comprising at least 30 consecutive nucleotides, preferably at least 50 consecutive nucleotides, more preferably at least 100 consecutive nucleotides, even more preferably at least 200 consecutive nucleotides, and most preferably all nucleotides of a gene encoding a kinin precursor (kininogen), such as, e.g., KNG1 kininogen 1 (SEQ ID NO:9). SEQ ID NO:9 relates to KNG1 kininogen 1 [Homo sapiens] according to NCBI:Pubmed Gene ID: 3827, Ensembl: ENSG00000113889, and is also known as BDK; KNG; KNG1, located on Chromosome 3: 186,435,065-186,461,743, forward strand, with protein lengths (transcript variants) of: 427 aa, 644 aa, 391 aa, 415 aa.

It will further be understood by a person skilled in the art that the KNG1 kininogen 1 gene may also be a nucleic acid sequence that has a sequence homology of at least 75%, at least 80%, at least 85%, at least 90% or at least 95% of SEQ ID NO:9 and encodes a functional KNG1 kininogen 1 protein or functional mutant thereof. Naturally, said gene is expressible into several protein variants (transcript variants), such as protein variants of a protein length of approximately 427 amino acids, of approximately 644 amino acids, of approximately 391 amino acids, or of approximately 415 amino acids in length.

In an alternative example, a nucleic acid may be a nucleic acid molecule comprising at least 200 consecutive nucleotides, preferably at least 300 consecutive nucleotides, more preferably at least 400 consecutive nucleotides, even more preferably at least 500 consecutive nucleotides, and most preferably all nucleotides of a gene encoding a bradykinin receptor, such as, e.g., BDKRB1 bradykinin receptor B1 (SEQ ID NO:10) or BDKRB2 bradykinin receptor B2 (SEQ ID NO:11). SEQ ID NO:10 relates to the BDKRB1 bradykinin receptor B1 [Homo sapiens] according to the NCBI: Pubmed Gene ID: 623, Ensembl:ENSG00000100739, and is also known as B1R; BKR1; B1BKR; BKB1R; BRADYB1; BDKRB1, located on Chromosome 14: 96,722,559-96,731,095, forward strand, with a protein length of 353 aa. SEQ ID NO:11 relates to the BDKRB2 bradykinin receptor B2 [Homo sapiens] according to NCBI:Pubmed Gene ID: 624, Ensembl:ENSG00000168398, and is also known as B2R; BK2; BK-2; BKR2; BRB2; DKFZp6860088; BDKRB2, located on Chromosome 14: 96,671,016-96,710,666, forward strand, with possible protein lengths of 391 aa, 364 aa.

It will further be understood by a person skilled in the art that a bradykinin receptor gene may also be a nucleic acid sequence that has a sequence homology of at least 75%, at least 80%, at least 85%, at least 90% or at least 95% of SEQ ID NO:10 or SEQ ID NO:11 and encodes a functional KNG1 kininogen 1 protein or functional mutant thereof. The full length protein of BDKRB1 bradykinin receptor B1 is typically approximately 353 amino acids in length. The full length protein of BDKRB2 bradykinin receptor B2 varies typically between approximately 391 and approximately 364 amino acids in length.

In an alternative example, a nucleic acid may be a nucleic acid molecule comprising at least 100 consecutive nucleotides, preferably at least 200 consecutive nucleotides, more preferably at least 300 consecutive nucleotides, even more preferably at least 400 consecutive nucleotides, and most preferably all nucleotides of a gene encoding a protease processing a kinin precursor into a kinin such as, e.g., bradykinin or kallidin. Said protease may be, e.g., a kallikrein, such as, e.g., KLK1 kallikrein 1 (SEQ ID NO:12). SEQ ID NO:12 relates to KLK1 kallikrein 1 [Homo sapiens] according to NCBI:Pubmed Gene ID: 3816, Ensembl: ENSG00000167748, also known as hK1; KLKR; Klk6; KLK1, located at Chromosome 19: 51,322,404-51,327,043, reverse strand, with a protein length of 262 aa or 160 aa.

It will further be understood by a person skilled in the art that a kallikrein gene may also be a nucleic acid sequence that has a sequence homology of at least 75%, at least 80%, at least 85%, at least 90% or at least 95% of SEQ ID NO:12 and encodes a functional KNG1 kininogen 1 protein or functional mutant thereof. The full length protein variants of KLK1 kallikrein are typically approximately 262 amino acids or 160 amino acids in length.

A nucleotide as used herein may be any nucleotide known in the art. The nucleotide may be linear or circular. Preferably, the nucleotide is double-stranded deoxyribonucleic acid (DNA). The double-stranded DNA may be linear or circular. The double-stranded DNA may be a plasmid. Alternatively, the nucleotide may also be single-stranded DNA, ribonucleic acid (RNA) or a nucleotide composed of nucleic acid analogues, such as, e.g., a peptide nucleic acid (PNA) nucleotide, a Morpholino nucleotide, glycol nucleic acid (GNA) nucleotide, a threose nucleic acid (TNA) nucleotide or a methylated DNA nucleotide. It will be understood by a person skilled in the art that different types of nucleotides may also be combined with another.

The nucleotide may be inserted in the body of the patient by any means known in the art such as, e.g., electroporation, transfecting agents (e.g., Chariot), positively charged polymers (e.g., polyethylene imine (PEI)), neutral lipids, positively charged lipids, viral vectors, liposomes, micro- and/or nanobeads, cell-penetrating peptides (=protein-transduction domains, e.g., polyarginines (e.g., R8, R9, R10), HIV Tat peptide, antennapedia/penetratin peptide, a Lactoferrin-derived peptide) and/or antimicrobial peptides.

Optionally, the bradykinin receptor agonist of the present invention may be labeled radioactively (e.g., by $^3$H, $^{32}$P, $^{35}$S, $^{14}$C, $^{99m}$Tc or lanthonoids (e.g., $^{64}$Gd)) or may be labeled with a spin label, such as one or more heavy isotopes, e.g., $^{13}$C, detectable by nuclear magnetic resonance (NMR) and magnetic resonance tomography (MRT).

Optionally, the bradykinin receptor agonist of the present invention may be labeled by one or more small molecule dye(s) (e.g., Cy dye(s) (e.g., Cy3, Cy5, Cy5.5, Cy7), Alexa dye/s (e.g., Alexa Fluor 488, Alexa Fluor 546, Alexa Fluor 647, Alexa Fluor 680, Alexa Fluor 750), VisEn dye(s) (e.g. VivoTag680, VivoTag750), S dye(s) (e.g., S0387), DyLight fluorophore(s) (e.g., DyLight 750, DyLight 800), IRDye(s) (e.g., IRDye 680, IRDye 800), fluorescein dye(s) (e.g., fluorescein, carboxyfluorescein, fluorescein isothiocyanate (FITC)), rhodamine dye(s) (e.g., rhodamine, tetramethylrhodamine (TAMRA)) or HOECHST dye(s)) or one or more quantum dot(s).

The bradykinin receptor agonist of the present invention may be provided by any means known in the art. As used throughout the present invention, the term "providing a bradykinin receptor agonist" may be understood in the broadest sense as obtaining a bradykinin receptor agonist from any source. The bradykinin receptor agonist may be provided by chemical synthesis, obtained from a biotechnological method and/or extracted from a natural source. Preferably, the bradykinin receptor agonist is provided by chemical synthesis. In the context of peptides, the term "chemical synthesis" may refer to SPPS, liquid phase peptide synthesis or a combination of both. Here, the synthesis typically bases on the stepwise coupling of amino acids bearing protected side chains (orthogonal protecting groups). Typically, during synthesis, the peptide strand grows from the C-terminus to the N-terminus. However, there are alternative methods wherein the peptide strand grows from the N-terminus to the C-terminus. Nowadays, the most common methods base on at least two different types of protecting groups that are cleavable under at least two different conditions, such as, e.g., the fluorenyl-9-methoxycarbonyl/tert-butanyl- (Fmoc/tBu) protecting group scheme (Sheppard Tactics) or the tert-butoxycarbonyl/benzyl- (Boc/Bzl) protecting group scheme (Merrifield Tactics). Alternatively or additionally, the peptide may be also provided by conjugating two or more peptide strand(s) with another by any conjugation method known in the art such as, e.g., Native Chemical Ligation (NCL), Click Chemistry, Maleimide-Thiol Conjugation, enzymatic conjugation, biochemical protein ligation and/or soluble handling conjugation.

Alternatively, the bradykinin receptor agonist may be obtained from a biotechnological method. Today, numerous biotechnological methods are well-known in the art such as, e.g., overexpression and/or heterologous expression, in particular heterologous expression based on cloning of one or more gene(s) in bacteria, insect cells, mammalian cells, plant cells or yeast cells. The bradykinin receptor agonist may further be extracted by any means known in the art. Alternatively, the bradykinin receptor agonist may be extracted from a natural source by any means known in the art. Additionally, the bradykinin receptor agonist may be purified by any means known in the art, such as, e.g., one or more chromatographic method(s), one or more filtration method(s), one or more electrophoretic method(s), one or more precipitation-based method(s), one or more dialysis method(s) or a combination of two or more thereof. The natural source may be any biological material such as, e.g., bacterial material, plant material, animal material or fungal material, such as e.g. tissue, liquids or secretion(s). Also bee toxin comprises bradykinin. The bradykinin receptor agonist obtained from a natural source may also be digested or partly digested by one or more enzymes, such as protease(s).

It will be understood by a person skilled in the art, that the aforementioned methods for providing a bradykinin receptor agonist may also be combined with another. In particular, a bradykinin receptor agonist obtained from a biotechnological method or a natural source may further be purified and/or modified by chemical means known in the art.

Any bradykinin receptor agonist may be used as an unbound molecule or may be non-covalently formulated with and/or conjugated to any other molecules such as, e.g., high-molecular weight compounds. Optionally, the bradykinin receptor agonist of the present invention may be stabilized against degradation by conjugation to one or more high-molecular weight compound(s).

Exemplarily, the bradykinin receptor agonist may be conjugated to one or more hydrophilic polymer(s). The term "hydrophilic polymer" as used herein may be understood in the broadest sense as any polymeric molecule that has a hydrophilic surface. A polymeric molecule comprises more than one monomer. The hydrophilic polymer may have a molecular mass of more than 500 Da. The hydrophilic polymer may be a soluble polymer, a gel-like polymeric matrix, a bead, a surface, a bead coating or the coating of a surface. Preferably, the hydrophilic polymer of the present invention is a soluble polymer. Exemplarily, the hydrophilic polymer of the present invention may be polyethylene glycol (PEG) or derivatives thereof, polyethylene imine (PEI) or derivatives thereof, polyacrylic acid or derivatives thereof, in particular hydroxypropyl methacrylate (HPMA), polysaccharide(s) or derivatives thereof, preferably amino polysaccharide(s), aminoalkyl polysaccharide(s), hydroxyalkyl polysaccharide(s) and/or alkyl polysaccharide(s), lipopolysaccharide(s), hydrophilic polypeptide(s) and/or conjugate(s) or blockpolymer(s) comprising two or more of the aforementioned. Alternatively, the hydrophilic polymer may be a bead having a hydrophilic surface or a bead having a coating comprising a hydrophilic polymer, in particular wherein the bead is a micro- or a nanobead. The hydrophilic polymer of the present invention may be conjugated with the bradykinin receptor agonist of the present invention via any functional group of the bradykinin receptor agonist. In particular when the bradykinin receptor agonist is a peptide, the hydrophilic polymer may be conjugated with the N-terminus of the peptide, an amino acid residue side chain, or the C-terminus of the peptide.

Conjugation to any other molecular structure may be facilitated by any means known in the art, such as the activation of one or more active groups(s). As used throughout the invention, the terms "active group" may be understood in broadest sense as a molecular moiety facilitating the formation of a bond, in particular an amide bond. Exemplarily, an active group may be an active ester (e.g., succinimidyl ester, N-hydroxysuccinimidyl (NHS) ester, carboxylic acid halogenide (acyl halide), pentafluorophenylester, thiophenyl ester, cyanomethyl ester, a nitrophenyl ester (e.g., 2-nitrophenyl ester, 4-nitrophenyl ester, 2,4-dinitrophenyl ester), a chlorophenyl ester (e.g., 2,4,5,-trichlorophenyl ester, pentachlorophenyl ester), pentafluorophenyl ester, N-hydroxypiperidinyl ester, 8-quinolyl ester, 1-hydroxybenzotriazolyl (HOBt) ester, 7-aza-1-hydroxybenzotriazolyl, N-norbornene-2,3-dicarboximidooxy ester, ethyl-1-hydroxy-1H-1,2,3-triazole-4-carboxylate), formation of an acid anhydride, and/or one or more coupling agent(s) (e.g., a carbodiimide (e.g., dicyclohexylcarbodiimide (DCC) and diisopropylcarbodiimide (DIC), a phosphonium reagent (e.g., benzotriazol-1-yloxy-tris(dimethylamino)phosphonium hexafluorophosphate (BOP)) or an uranium-type reagent (e.g., HBTU, TBTU, HATU, HAPyU, HAMDU, HAPipU, HAMTU). Alternatively, the bradykinin receptor agonist may be conjugated to the hydrophilic polymer by any other means known in the art such as, e.g., by Native Chemical Ligation (NCL), Click Chemistry, Maleimide-Thiol Conjugation, and/or employing two or more different types of orthogonal protecting groups (e.g., convergent SPPS).

The bradykinin receptor agonist of the present invention may also be a compound inhibiting the degradation of any other bradykinin receptor agonist. As mentioned above, many bradykinin receptor agonists, such as, e.g., the kinins bradykinin and kallidin, are inactivated by proteolytic cleavage, in particular proteolytic cleavage of the carboxy terminal amino acids. Cleavage may be mediated by the angiotensin-converting enzyme (ACE) or related enzymes. Therefore, any ACE inhibitor known in the art may also be used as a bradykinin receptor agonist in the context of the present invention. Further, inhibitors of the amino peptidase P (APP) and the carboxypeptidase N(CPN) may be used as a bradykinin receptor agonist in the context of the present invention.

It will be understood by a person skilled in that art that optionally two or more bradykinin receptor agonist(s) may be combined with another. Particularly, one or more compound(s) inhibiting the degradation of any other bradykinin receptor agonist may be combined with one or more bradykinin receptor agonist(s) of other type(s).

The term "preventing" or "prevention" or "prophylactic treatment" as used in the context of the present invention may be understood in the broadest sense as any means for decreasing the risk of developing a particular condition, such as a cardiovascular ischemic disease or condition or diminishing the upcoming implication of a cardiovascular ischemic disease or condition.

As used herein, the term "disorder associated with defective blood flow" may be understood in the broadest sense as any condition where the blood flow of a patient is in any way aberrant from normal or healthy blood flow. Such conditions include conditions where blood flow is restricted, such as cardiovascular ischemic disease, in addition to conditions where blood vessels are malformed, which may lead to unwanted increases in or rates of blood flow.

As used herein, the term "cardiovascular ischemic disease" may be understood in the broadest sense as any disease or condition associated with a restriction of blood flow, wherein said restriction of blood flow is generally due to factors in the blood vessels.

The term "patient at risk" may refer to any subject who is at risk of developing a disease condition in the sense of the present invention. Preferably, the risk of developing a disease condition for this subject is at least 5%, at least 10%, at least 25%, at least 50%, at least 75%, at least 100%, at least 150%, at least 200%, at least 300%, at least 500%, or more than 500% higher compared to the average risk throughout the population. The patient in the sense of the present invention may be any subject who can develop a cardiovascular ischemic disease or condition in the sense of the present invention. Preferably, the patient is a mammal, in particular a human.

The bradykinin receptor agonist of the present invention may be administered by any means known in the art. Exemplarily, administration may be oral administration, injection (e.g., intravenous, intraperitoneal, subcutaneous or intramuscular injection), intranasal administration, topical administration or intradermal administration. In case of peptides or peptidomimetics, administration is preferably enabled via an injection in order to circumvent the first pass effect. The dose of the bradykinin receptor agonist administered evidently depends on numerous factors well-known in the art such as, e.g., the chemical nature and pharmaceutical formulation of the bradykinin receptor agonist, and of body weight, body surface, age and sex of the patient, as well as the time and route of administration. For an adult, the dose may exemplarily be between 0.5 µg and 1 g per day, preferably between 0.5 µg and 100 mg per day, more preferably between 1 µg and 100 mg per day, even more preferably between 1 µg and 100 mg per day, even more preferably between 1 µg and 10 mg per day, even more preferably between 5 µg and 10 mg per day. In a continuous infusion, the dose may exemplarily be between 0.5 µg and 100 mg, preferably between 1 µg and 10 mg per kilogram per minute. Should the bradykinin receptor agonist be a nucleic acid approximately between $10^6$ copies and $10^{12}$ copies may be administered to the patient, depending on the used vector.

The present invention also relates to a method for the prevention of a cardiovascular ischemic disease in a patient at risk thereof by administering a pharmaceutically active amount of a bradykinin receptor agonist to said patient.

In a preferred embodiment, the bradykinin receptor agonist of the present invention induces arteriogenesis.

As described above, the term "arteriogenesis" as used in the context of the present invention may be understood in the broadest sense as the growth of arteries from preexisting arteriolar connections. In particular, arteriogenesis is the blood flow stimulated in situ growth of arteries by proliferation of endothelial and smooth muscle cells from preexisting arteriolar connections supplying blood to ischemic tissue. Therefore, arteriogenesis is induced by flow, namely by an increased shear stress which act on endothelial cells. This activates the bradykinin receptor signal pathway, through which arteriogenesis is enhanced. Collateral blood vessel growth can be modified (inhibition or stimulation) through modulation of the bradykinin receptor signal pathway. This enables methods involving the modification of this mechanism for the prevention of circulatory disorders, vascular diseases and/or ischemic arterial blockages or occlusions (KHK, stroke, PAVK). Modulation of arteriogenesis via the bradykinin signaling pathway can also be applied to other illnesses or disorders, for example AV-shunt malformation and the Moja Moja disease. The vessels largely growth outside from the vascular occlusion affected tissue but are much more important for the delivery of nutrients to ischemic territory, than capillaries sprouting in the diseased tissue by angiogenic processes. Therefore, arteriogenesis may function like a physiological bypass.

Arteriogenesis is mechanically linked to an elevated pressure in the vessels, which increases radial wall stress, and elevated flow, which may increase endothelial surface stress. In response, the vessels may increase in diameter until the stress is normalized.

The arteriogenesis of the present invention differs from angiogenic processes as the latter refer to the induction of capillary sprouting. Therefore, arteriogenesis decreases the flow resistance due to an increase of the diameter of collateral vessels from existing arterial networks, whereas angiogenesis may eventually even increase the flow resistance of the blood stream as, according to the Hagen-Poiseuille rule, the relationship between blood flow and artery diameter is enhanced by an exponential factor of 4 in relationship to the radius and the capillary diameter is typically small (often between 5 and 7 μm). Therefore, the present intervention relates to the enhancement of collateral artery growth with one or more bradykinin receptor agonist(s) by inducing arteriogenesis.

Accordingly, the present invention also refers to the bradykinin receptor agonist for use in a method for enhancing arteriogenesis for the treatment or prevention of cardiovascular ischemia.

In a further preferred embodiment, the patient is tested for arteriogenesis.

As used herein, the term "tested for arteriogenesis" may be understood in the broadest sense as any method showing the rate of arteriogenesis of the patient. The testing of arteriogenesis may be in vivo testing or in vitro (ex vivo) testing. Testing may be conducted by any means known in the art such as, e.g., testing of a blood sample, microscopic examination of the tissue, magnetic resonance tomography (MRT), computer tomography (CT), positron emission tomography (PET) scanning, diagnostic sonography, doppler sonography, examination of an extracted tissue sample, enzyme linked immunosorbent assay (ELISA), polymerase chain reaction (PCR), quantitative PCR and/or real-time PCR. It will further be understood by a person skilled in the art that different testing methods may also be combined with another and with staining methods such as, e.g., immunostaining and/or histolytic staining, and staining agents such as, e.g., fluorescence dyes and/or contrast agents.

In another preferred embodiment, the bradykinin receptor agonist of the present invention is a bradykinin receptor 1 agonist and/or a bradykinin receptor 2 agonist.

As used herein, the term "bradykinin receptor 1 agonist" may be understood as a compound that, at a given concentration, activates the bradykinin receptor 1 more than other bradykinin receptors such as the bradykinin receptor 2. Preferably, the bradykinin receptor 1 agonist activates the bradykinin receptor 1 more than 1.2 times, more than 1.5 times, more preferably more than 2 times, even more preferably more than 3 times, even more preferably more than 5 times more than the bradykinin receptor 2.

As used herein, the term "bradykinin receptor 2 agonist" may be understood as a compound that, at a given concentration, activates the bradykinin receptor 2 more than other bradykinin receptors such as the bradykinin receptor 1. Preferably, the bradykinin receptor 2 agonist activates the bradykinin receptor 2 more than 1.2 times, 1.5 times, more preferably more than 2 times, even more preferably more than 3 times, even more preferably more than 5 times more than the bradykinin receptor 1.

In a preferred embodiment, the bradykinin receptor agonist of the present invention is a bradykinin receptor 1 agonist.

Angina pectoris is a well-known disease condition characterized in that the patient has pain in the breast, in particular when exerting. Angina pectoris in the sense of the present invention may be stable angina or unstable angina. Stable angina is characterized in that it regularly occurs when exerting. Unstable angina is characterized in that it occurs irregularly, thus, sometimes when the patient exerts.

Further, a cardiovascular ischemic disease in the sense of the present invention may also be ischemic organ failure, in particular renal ischemia, renal occlusive disease, renal retinopathy, neuropathy, gut ischemia, bowel ischemia, mesenteric ischemia, mesenterial artery insufficiency, ischemic colitis, cutaneous ischemia and/or mottling.

As used herein, the terms "myocardial infarction" and "myocard infarct" may be understood interchangeably.

The term "particular periphery arterial occlusive disease" may be understood in the broadest sense as any disease state wherein the blood stream in a periphery arterial is disturbed. Typically, the patient will suffer from muscle pain when taking a rest.

The symptoms of being at risk of developing a cardiovascular ischemic disease may be any symptoms that are known in the art. Many symptoms may be observable when examining the patient by routine methods. For instance, high blood pressure is a typical symptom of being at risk. The symptoms may also include behavior such as motor movements. A smoking subject, in particular a heavily smoking subject may also be at particular risk.

A risk marker may be any risk marker known in the art. In particular, blood values may play an important role. For instance, a particularly high cholesterol level shows that the patient is at risk. A person skilled in the art will immediately see that it has to be up to the medical experts to determine exact concentrations and further risk markers showing that a patient is at risk.

A person who previously had a cerebral or myocardial ischemia is typically at risk.

A genetic predisposition in the sense of the present invention may be any genetic predisposition associated with ischemic diseases such as, e.g., diabetes type I or II, a congenital heart disease, lack of the expression of one or more bradykinin receptor(s), lack of the expression of one or more bradykinin precursor(s), or failure of cleavage of one or more bradykinin precursor(s).

Further, a person who had been subjected to a surgical procedure may be at particular risk.

In another preferred embodiment, the aforementioned symptoms of the patient at risk of developing a cardiovascular ischemic disease are selected from the group consisting of neurological malfunctions, transitory ischemic attack, congestive heart failure, transitory ischemic attack, angina pectoris, valvular heart disease, cardiomyopathy, pericardial disease, congenital heart disease, coarctation, atrial or ventricular septal defects and combinations of two and more thereof.

In another preferred embodiment, the patient further exhibits in particular, sclerosis, in particular atherosclerosis and/or transplantation-induced sclerosis; a cerebral occlusive disease, renal occlusive disease, a mesenterial artery insufficiency or an ophthalmic or retinal occlusion, post-operative or post-traumatic condition play an important role. Every injury may increase the risk of developing a cardiovascular ischemic disease.

In a preferred embodiment, the patient previously had been exposed to or is going to be exposed to a pharmaceutical or medical treatment damaging one or more arteries; a radiation treatment damaging one or more arteries; or a surgical treatment damaging one or more arteries.

A pharmaceutical or medical treatment may be any treatment that damages or harms arteries. Preferably, the treatment may refer to a local injection of a pharmaceutical compound, in particular a permanent local injection such as a drip injection. Here, the local concentration is very high. The pharmaceutical compound may, e.g., be a chemotherapeutic such as, e.g., a cancer agent (e.g., doxorubicin), that can lead to local necrosis. A medical treatment may be, e.g., dialysis. Here, the vessels may show an occlusion as platelets, calcium and other factors can form local plaques near the spot where the needle is regularly placed. A radiation treatment may be any treatment using radiation such as, e.g., X-ray radiation, radioisotope radiation, thermal radiation. Radiation therapy may also be combined with chemotherapy and/or micro- or nanobeads. A surgical treatment may refer to any surgical treatment known in the art, in particular an intracranial surgical treatment.

It will be apparent to a person skilled in the art that the pharmaceutical or medical treatment, the radiation treatment and the surgical treatment damaging one or more arteries itself is not encompassed by the present invention, but has been conducted previously or subsequently.

As used herein, arterial occlusive disease may also be intermittent claudation. The invention further relates to a method for treating a cardiovascular ischemic disease in a patient in need thereof, wherein a pharmaceutically effective amount of a bradykinin receptor agonist is administered to said patient and wherein said cardiovascular ischemic disease is a peripheral limb disease, in particular periphery arterial occlusive disease.

In a preferred embodiment, the bradykinin receptor agonist of the present invention further induces migration of leukocyte cells and/or leukocyte precursor cells.

As used herein, the term "leucocyte cell" may be understood interchangeable with the terms "leucocyte" and "white blood cells" as any leucocyte cell known in the art. Exemplarily, the leucocyte cell may be a myeloid cell or a lymphoid cell. Preferably, a leucocyte cell may be a granulocyte (e.g., a neutrophil granulocyte, an eosinophil granulocyte, a basophil granulocyte), a lymphocyte (e.g., a B-cell lymphocyte, a T-cell lymphocyte (e.g., a CD4+ T cells (T helper cell), a CD8+ T cell (cytotoxic T cell), a yδ T cell)), a monocyte, or a fixed leukocyte (e.g., a fixed macrophage (e.g. a Kupffer cell), a histiocyte, a dendritic cell, a mast cell, microglia). More preferably, a leucocyte cell of the present invention is a neutrophil granulocyte and/or a monocyte.

The term "leucocyte precursor cell" may be understood interchangeably with the term "progenitor cell" in the broadest sense as any cell known in the art that can mature into a leucocyte cell. The precursor cell may be a pluripotent precursor cell. AS used herein, the term "pluripotent" may be understood interchangably with "multipotent". The precursor cell may be a stem cell, in particular a pluripotent stem cell. Preferably, the leucocyte precursor cell is not a progenitor cell of endothelial cells. Highly preferably, the leucocyte precursor cell is a hematopoietic progenitor cell. Said hematopoietic progenitor cell may be any hematopoietic progenitor cell known in the art such as, e.g., a myoloblast, Mo-blast, L-blast, myelocyte or megakaryocyte. Preferably, said hematopoietic progenitor cell is a myoloblast or Mo-blast. A hematopoietic progenitor cell may also be a hematopoietic stem cell (HSC).

Preferably, the leukocyte cells and/or leukocyte precursor cells migrate due to chemotactic signals. Preferably, the leukocyte cells and/or leukocyte precursor cells modulate arteriogenesis by chemotactic secretion of growth factors and inflammatory cytokines that may be important for the remodeling of an artery, in particular wherein the leukocyte cells and/or leukocyte precursor cells induce arteriogenesis. Typically, said secretion is a paracrine secretion that influences arteriogenesis locally.

In another preferred embodiment, the bradykinin receptor agonist of the present invention is administered in a long-term application. Preferably, said long-term application begins before the patient suffers from a cardiovascular ischemic disease or condition. Alternatively, said long-term application begins after at least two days, after at least four days, after at least at least one week, at least two weeks, at least one months, at least two months, at least half a year or at least one year after the occurrence of a cardiovascular ischemic disease or condition, wherein said cardiovascular ischemic disease or condition is in particular stroke or a myocard infarction. Alternatively, said long-term application begins after at least two days, after at least four days, after at least at least one week, at least two weeks, at least one months, at least two months, at least half a year or at least one year after the patient previously had been exposed a pharmaceutical or medical treatment, a radiation treatment or a surgical treatment damaging one or more arteries. Alternatively, said long-term application begins at least one day, two days, three days, at least one week, at least two weeks, at least one months or at least two months before the patient is going to be exposed to a pharmaceutical or medical treatment, a radiation treatment or a surgical treatment damaging one or more arteries. In a more preferred embodiment, the long-term application is administrating said bradykinin receptor agonist of the present invention to the patient for at least one week, at least two weeks, at least three weeks, at least four weeks, at least one month, at least two months, at least three months, at least four months, at least five months, at least six months, at least seven months, at least eight months, at least nine months, at least ten months, at least eleven months, at least one year, at least two years, at least three years or enduringly. Preferably, a long-term application is an application for a time span of between one week and two years, more preferably of between one week and one year, even more preferably of between one week and 26 weeks and most preferably of between one week and twelve weeks.

Especially with regards to enzyme inhibitors, the term "inhibitor" refers to compounds that diminish the functionality, thus, typically the rate of conversion catalyzed by an enzyme, of the enzyme they inhibit. Preferably, the rate of conversion is less than 0.5 times, more preferably less than 0.25 times, even more preferably less than 0.1 times, more preferably less than 0.05 times as active as the enzyme without an inhibitor. Herein, the peptidase is preferably a carboxy peptidase.

As used in the context of the present invention, the term "bradykinin receptor antagonist" may be understood in the broadest sense as any compound that can directly or indirectly inhibit the function of a bradykinin receptor or the signal transduction cascade related to a bradykinin receptor. The bradykinin receptor agonist may be a peptidomimetic, a non-peptide antagonist, a nucleic acid molecule inhibiting bradykinin precursor expression or bradykinin receptor expression, or a compound stimulating the degradation of an intrinsic bradykinin receptor agonist.

Preferably, the bradykinin receptor antagonist is a peptidomimetic, in particular a peptidomimetic consisting of nine or ten amino acids and amino acid analogues. Exemplarily, the peptidomimetic bradykinin receptor antagonist is icatibant (HOE140, H157); CP0597; D-Arg[Hyp3,Thi5, HypE(trans-propyl)7,Oic8]-bradykinin (NPC17731). The bradykinin receptor antagonist may also be a non-peptide antagonist such as, e.g., FR167344 or FR173657.

Said siRNA, microRNA or a nucleic acid analogue may be complementary to a part of the sequence of a gene encoding a bradykinin precursor (kininogen), such as, e.g., KNG1 kininogen 1 (SEQ ID NO:9); a gene encoding a bradykinin receptor, such as, e.g., BDKRB1 bradykinin receptor B1 (SEQ ID NO:10) or BDKRB2 bradykinin receptor B2 (SEQ ID NO:11); or a gene encoding a protease processing a bradykinin precursor to a kinin such as, e.g., bradykinin or kallidin, wherein said protease may be, e.g., a kallikrein, such as, e.g., KLK1 kallikrein 1 (SEQ ID NO:12).

The term "part of the sequence" as used herein mean a sequence of at least 6, at least 10, at least 15, at least 20, at least 25, at least 30 or at least 35 nucleotides in length.

As used herein, a vessel malformation is preferably the overproduction of vessels, in particular the overproduction of connections between arteries and arterioles and veins and venules (arteriovenous malformation). These malformations typically occur upon surgical proceedings, in particular upon intracranial surgical proceedings.

The bradykinin receptor antagonist of the present invention may be administered by any means known in the art. Exemplarily, administration may be oral administration, injection (e.g., intravenous, intraperitoneal, subcutaneous, intramuscular, intranasal injection), topical administration or intradermal administration. In case of peptides or peptidomimetics, administration is preferably enabled via an injection in order to circumvent the first pass effect. The dose of the bradykinin receptor antagonist administered evidently depends on numerous factors well-known in the art such as, e.g., the chemical nature and pharmaceutical formulation of the bradykinin receptor antagonist, and of body weight, body surface, age and sex of the patient, as well as the time and route of administration. For an adult, the dose may exemplarily be between 0.5 µg and 1 g per day, preferably between 0.5 µg and 100 mg per day, more preferably between 1 µg and 100 mg per day, even more preferably between 5 µg and 10 mg per day, even more preferably between 1 µg and 10 mg per day. In a continuous infusion, the dose may exemplarily be between 0.5 µg and 100 mg, preferably between 1 µg and 10 mg per kilogram per minute. Should the bradykinin receptor antagonist be a nucleic acid approximately between $10^6$ copies and $10^{12}$ copies may be administered to the patient, depending on the used vector.

The present invention further relates to a method for treating or preventing the formation of vessel malformation in a patient, wherein a pharmaceutically active amount of a bradykinin receptor antagonist is administered to said patient. Therefore, in a preferred embodiment, the patient has previously been subjected to a surgical procedure and is at risk of developing an arteriovenous malformation. Alternatively, the patient may also be subjected to physical stress or trauma via an accident. In another preferred embodiment, the bradykinin receptor antagonist of the present invention is used in a method for treating a patient suffering from the Moja Moja Syndrome.

The terms "Moja Moja Syndrome", "MojaMoja Syndrome" and "MoyaMoya Syndrome" may be understood interchangeably as a disease in which certain arteries in the brain are constricted. Blood flow is blocked by the constriction, and also by blood clots (thrombosis). The clinical features are cerebral ischemia (in particular strokes), recurrent transient ischemic attacks, sensorimotor paralysis (e.g., numbness and paralysis of the extremities), convulsions and/or migraine-like headaches. After an ischemic stroke, a hemorrhagic reperfusion stroke may occur. A hemorrhagic stroke may also stem from a rupture of the weak neovascular vessel walls.

In another preferred embodiment, the bradykinin receptor antagonist of the present invention is administered in a long-term application. The term long term application in relation to the bradykinin receptor antagonist can be understood in the same manner as long term application as described above for the agonist.

In a more preferred embodiment, the bradykinin receptor antagonist of the present invention is selected from the group consisting of HOE140, CP0597, NPC17731, FR167344; FR173657; a nucleic acid molecule inhibiting the formation of an intrinsic bradykinin receptor agonist or a bradykinin receptor and a combination of two or more thereof.

In a preferred embodiment, the aforementioned nucleic acid molecule that may serve as a bradykinin receptor agonist of the present invention is siRNA, microRNA or a nucleic acid analogue. Preferably, the siRNA or microRNA is complementarity to mRNA of components of the kallikrein-kinin system (e.g., a bradykinin precursor (e.g., kininogen), bradykinin receptor 1 and/or bradykinin receptor 2). Alternatively, the nucleic acid molecule may be DNA encoding said siRNA or microRNA.

An intrinsic bradykinin receptor antagonist may be any molecule decreasing the activity of a bradykinin receptor, wherein said molecule is produced by the patient's body itself. Exemplarily, an intrinsic bradykinin receptor antagonist may be an enzyme degrading bradykinin or kallidin. Preferably said enzyme is a protease, more preferably a carboxy peptidase, in particular ACE. The intrinsic bradykinin receptor antagonist may be given into the patient directly or a nucleic acid molecule encoding said intrinsic bradykinin receptor antagonist is given to the patient and expressed in said patient.

It will be understood by a person skilled in the art that two or more bradykinin receptor antagonist of the present invention may be combined with another. Further, one or more bradykinin receptor agonist(s) and one or more bradykinin receptor antagonist(s) of the present invention may be combined with another.

Moreover, one or more bradykinin receptor agonist(s) and/or one or more bradykinin receptor antagonist(s) of the present invention may be combined with other potential modulators or arteriogenesis such as, e.g., one or more colony stimulating factor(s) (CSF(s)) and/or one or more eicosanoid(s) (e.g., prostaglandin(s), prostacycline(s), leukotriene(s), thromboxane(s)).

In a further aspect, the present invention refers to a pharmaceutical composition comprising one or more bradykinin receptor agonists(s) of the present invention and/or one or more bradykinin receptor antagonists(s) of the present invention and a pharmaceutical acceptable carrier.

Preferably, the pharmaceutical composition comprises one or more bradykinin receptor agonists(s) of the present invention or one or more bradykinin receptor antagonists(s) of the present invention and a pharmaceutical acceptable carrier.

A pharmaceutical acceptable carrier in the sense of the present invention may be any non-toxic material that does not interfere with the effectiveness of the biological activity of the bradykinin receptor agonists(s) and/or bradykinin receptor antagonists(s) of the present invention. Evidently, the characteristics of the carrier will depend on the route of administration. Such a composition may contain, in addition to the active substance and carrier, diluents, fillers, salts, buffers, stabilizers, solubilizers, and other materials well known in the art. Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

The medicament, otherwise known as a pharmaceutical composition, containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyceryl distearate may be employed. They may also be coated.

The present invention refers to a pharmaceutical composition for topical application, oral ingestion, inhalation, or cutaneous, subcutaneous, or intravenous injection. Topical application is one preferred embodiment, especially via a cream or gel. Topical application forms relate to gels, creams, suppositories, or films. The pharmaceutical composition of the invention may be in the form of a liposome in which the active substance of the invention is combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art.

When a therapeutically effective amount of the active substance of the invention is administered by intravenous, cutaneous or subcutaneous injection, the active substance will be in the form of a pyrogen-free, parenterally acceptable aqueous solution. As used herein, the term "therapeutically effective amount" means the total amount of each active component of the pharmaceutical composition or method that is sufficient to show a meaningful patient benefit. The amount of active substance in the pharmaceutical composition of the present invention will depend upon the nature and severity of the condition being treated, and on the nature of prior treatments which the patient has undergone. Larger doses may be administered until the optimal therapeutic effect is obtained for the patient, and at that point the dosage is not increased further.

The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to the active substance, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

Further, a pharmaceutical acceptable carrier in the sense of the present invention may be any molecule(s) known in the art to facilitate uptake or to enhance the rate of uptake such as, e.g., positively charged polymer(s) (e.g., polyethylene imine (PEI)), neutral lipid(s), positively charged lipid(s), viral vector(s), liposome(s), micro- and/or nanobead(s), cell-penetrating peptide(s) (=protein-transduction domains, e.g., polyarginines (e.g., R8, R9, R10), HIV Tat peptide, antennapedia/penetratin peptide, a Lactoferrin-derived peptide), antimicrobial peptides and/or a Chariot peptide.

The present invention also relates to the pharmaceutical composition of the present invention for use in a method as described above. In particular, the pharmaceutical composition of the present invention is used in a method for enhancing collateral artery growth and for preventing a cardiovascular ischemic disease in a patient at risk thereof or for treating or preventing a cardiovascular ischemic disease in a patient in need thereof, wherein said cardiovascular ischemic disease is a peripheral limb disease, in particular periphery arterial occlusive disease.

The present invention further relates to modulation of flow induced collateral vessel or artery growth and the outgrowth of collateral arterioles from pre-existing arterial networks. Further subject matter of the invention is the induction or reduction of collateral vessel growth through the stimulation (agonists) or inhibition (antagonist) of the bradykinin receptor 1 and/or bradykinin receptor 2 signaling pathways in the artery or blood vessel wall (modulation of the bradykinin receptors of the endothelial cells, the smooth muscle cells or the leucocytes that have migrated into the vessel or artery wall).

Collateral vessel growth or artery growth according to the present invention are terms than can be used to describe arteriogenesis. Arteriogenesis is characterized by the outgrowth of collateral arterioles from pre-existing arterial networks. The term "pre-existing arterial networks" can also be described as arterial networks with pre-existing arteriolar connections, such as pre-existing capillaries, arteries, vessels or other conduits of blood found in a mammalian organism. Therefore the present invention further relates to the use of a bradykinin receptor 1 (B1R) and/or bradykinin receptor 2 (B2R) stimulating substance for modulating collateral growth of collateral arteries and/or other arteries from pre-existing arteriolar connections.

Agonists can be used for the induction of collateral vessel or artery growth (arteriogenesis) via the stimulation of the bradykinin receptor signaling pathways. Various BR-agonists can be used for the modulation of arteriogenesis, such as the nonapeptide bradykinin, structurally related kinins (T kinin, kallidin, Des-Arg$^9$-bradykinin and Des-Arg$^{10}$-kallidin) in addition to further structurally related substitutes with modified amino acid sequences. The invention further relates to an induction of arteriogenesis through the stimulation of bradykinin receptors with non-peptide molecules.

The invention further relates to the inhibition of arteriogenesis via antagonists of the bradykinin receptors. As antagonists the following molecules are intended as examples: icatibant (BR2 antagonists) or (Des-Arg$^9$, Leu$^8$)-bradykinin (BR1 antagonists), in addition to related substitutes or alternatives with modified amino acid sequences. The inhibition of arteriogenesis via non peptide molecules, which preferably bind to the bradykinin receptor, is a further aspect of the invention. The invention also includes modulation of collateral blood vessel or artery growth by means of nucleic acid molecules, for example through nucleic acid molecules (siRNA, microRNA) with homology to the mRNA of components of the kallikrein-kinin systems (for example kininogen, BR1, BR2).

The present invention is relevant for the medical and pharmaceutical industries. A stimulation of arteriogenesis via the bradykinin receptor signaling pathways, particularly via a long-term application of a stimulant for the prevention of ischemic insults, is subject matter of the present invention. Further subject matter of this invention is therefore the prevention of strokes, coronary heart conditions or PAVKs via a stimulation of the bradykinin signaling pathways. Patients which have already exhibited the first warning signal of a stroke (the so called transitory ischemic attacks [TIA]), are one example of a patient group that could benefit from the therapeutic induction of arteriogenesis. Patients with such vessel or artery constriction could avoid the threatening stroke or coronary heart condition by an induction of a naturally occurring biological bypass via bradykinin receptor agonists, when applied at an early time point.

The present invention relates therefore to the prevention and/or therapy of circulatory disorders, cardiovascular disease, artery or blood vessel conditions and/or ischemic obstructive or occlusive diseases or conditions.

Circulatory disorders, cardiovascular disease, artery or blood vessel conditions and/or ischemic obstructive or occlusive diseases or conditions are terms that encompass a variety of diseases and conditions. The diseases treated and/or prevented by the present invention are vascular diseases of mammals. The word mammal means any mammal. Some examples of mammals include, for example, pet animals, such as dogs and cats; farm animals, such as pigs, cattle, sheep, and goats; laboratory animals, such as mice and rats; primates, such as monkeys, apes, and chimpanzees; and humans. In some embodiments, humans are preferably treated by the methods of the invention.

The terms circulatory disorders, cardiovascular disease, artery or blood vessel conditions and/or ischemic obstructive or occlusive diseases or conditions refer to states of vascular tissue where blood flow is, or can become, impaired or altered from normal levels. Many pathological conditions can lead to vascular diseases that are associated with alterations in the normal vascular condition of the affected tissues and/or systems. Examples of vascular conditions or vascular diseases to which the methods of the invention apply are those in which the vasculature of the affected tissue or system is senescent or otherwise altered in some way such that blood flow to the tissue or system is reduced or in danger of being reduced or increased above normal levels. It refers to any disorder in any of the various parts of the cardiovascular system, which consists of the heart and all of the blood vessels found throughout the body. Diseases of the heart may include coronary artery disease, CHD, cardiomyopathy, valvular heart disease, pericardial disease, congenital heart disease (e.g., coarctation, atrial or ventricular septal defects), and heart failure. Diseases of the blood vessels may include arteriosclerosis, atherosclerosis, hypertension, stroke, vascular dementia, aneurysm, peripheral arterial disease, intermittent claudication, vasculitis, venous incompetence, venous thrombosis, varicose veins, and lymphedema.

Examples of vascular conditions that can be treated or prevented with the compositions and methods of the invention include atherosclerosis, preeclampsia, peripheral vascular disease, erectile dysfunction, cancers, renal failure, heart disease, and stroke. Vascular, circulatory or hypoxic conditions to which the methods of the invention apply also include those associated with, but not limited to, maternal hypoxia (e.g., placental hypoxia, preeclampsia), abnormal pregnancy, peripheral vascular disease (e.g., arteriosclerosis), transplant accelerated arteriosclerosis, deep vein thrombosis, erectile dysfunction, cancers, renal failure, stroke, heart disease, sleep apnea, hypoxia during sleep, female sexual dysfunction, fetal hypoxia, smoking, anemia, hypovolemia, vascular or circulatory conditions which increase risk of metastasis or tumor progression, hemorrhage, hypertension, diabetes, vasculopathologies, surgery (e.g., per-surgical hypoxia, post-operative hypoxia), Raynaud's disease, endothelial dysfunction, regional perfusion deficits (e.g., limb, gut, renal ischemia), myocardial infarction, stroke, thrombosis, frost bite, decubitus ulcers, asphyxiation, poisoning (e.g., carbon monoxide, heavy metal), altitude sickness, pulmonary hypertension, sudden infant death syndrome (SIDS), asthma, chronic obstructive pulmonary disease (COPD), congenital circulatory abnormalities (e.g., Tetralogy of Fallot) and Erythroblastosis (blue baby syndrome). In particular embodiments, the invention is a method of treating loss of circulation or endothelial dysfunction in an individual.

Thus, the invention is directed to compositions useful in a method of treating and/or preventing diseases such as stroke, atherosclerosis, acute coronary syndromes including unstable angina, thrombosis and myocardial infarction, plaque rupture, both primary and secondary (in-stent) restenosis in coronary or peripheral arteries, transplantation-induced sclerosis, peripheral limb disease, intermittent claudication and diabetic complications (including ischemic heart disease, peripheral artery disease, congestive heart failure, retinopathy, neuropathy and nephropathy), or thrombosis.

Circulatory disorders relate to various organs such as brain stem, heart, kidney, adrenal and lung. In addition, the present invention is useful for the prevention and treatment of the diseases induced by peripheral circulation failure in mammals, such as Raynaud's syndrome, arteriosclerosis obliterans, romsoongitis obliterans, Buerger disease, diabetic microvascular disorders and peripheral arterial obstruction (e.g. diabetic gangrene). Moreover, the present invention is useful for the prevention and treatment of hypertensive organ circulatory disorders, as well as for the treatment of cerebrovascular disorders both in acute stages and chronic stages.

Ischemic conditions include coronary arteriosclerosis, angina pectoris, and acute and old myocardial infarction and refers to the serious disorder of the vital heart that mostly affects males and females in late middle age or older. Coronary arteriosclerosis is characterized by arteriosclerosis in the coronary artery that supplies nutrients to the heart. Angina pectoris is characterized by attacks of chest pain caused by impaired blood flow in the coronary artery. Myocardial infarction is characterized by myocardial necrosis caused by impaired blood flow in the coronary artery and by fatal complications coming there with such as arrhythmia, cardiac failure, cardiac rupture, and pump failure. Impaired blood flow to the heart, a vital organ, is an essential characteristic of these ischemic heart diseases Peripheral arterial occlusive disease (PAOD; also referred to as peripheral arterial disease (PAD)) results either from atherosclerotic or inflammatory processes producing arterial stenosis, or from thrombus formation associated with underlying atherosclerotic disease. A common site for PAOD is in the lower limbs. This process of atherosclerosis causes initial thickening and plaque formation encroaching the arterial lumen, decreasing the effective luminal radius of afflicted arterial segments, producing an anatomic and sometimes functional obstruction to blood flow.

Conditions such as the Moja Moja syndrome can however be treated through modulation of arteriogenesis. The Moja Moja condition is characterized by closing of the internal carotid artery, whereby the blood flow can however be maintained over collateral arteries. A stimulation of the collateral blood flow can in such cases lead to an enhanced perfusion in a hypoperfusion area.

Flow induced collateral blood vessel growth has not only a physiological importance but can also lead to a pathological formation of collateral vessels and arteries, especially in cases of etiologically unclear brain diseases involving the arterio-venous vessel malformation. An AV-shunt can usually be treated using a medical gel in an operative situation in order to close the shunt. This treatment of arterio-venous malformation can however lead to the induction of collateral blood vessels and arteries, which after the operation can however lead to the further growth of collateral arteries and therefore formation of a new shunt. In such cases the inhibition of arteriogenesis through the bradykinin receptor antagonists (for example as part of an AV-shunt gel) would be useful.

Ligand B1 and B2 receptor agonism plays beneficial and protecting roles in cardiovascular-related pathologies such as ischaemic heart diseases, periphery artery diseases and stroke. The present invention indicates that a strong cardioprotective effect is provided by bradykinin receptor signaling to therapeutically enhance arteriogenesis. Therefore it is suggested to therapeutically stimulate arteriogenesis via the B2 receptors and preferably via the B1 receptor pathway (see FIG. 6). Stimulation of collateral artery growth in case of obstruction or occlusion of a major artery, enhancing blood flow into the hypoperfused area distal of the occlusion, can prevent ischemia.

Interestingly, both bradykinin receptors exhibit different biological features, such as that B2 receptors are considered to be constitutively expressed and ready to respond to newly formed kinins. Upon ligand binding B2 receptors are rapidly desensitized and degraded. In contrast, Bradykinin receptor 1 is expressed upon induction. B1 receptors generally exhibit long term effects. Since signaling via B1 or B2 receptors will result in different signaling pathways, stimulation of bradykinin receptor 2 or bradykinin receptor 1 by selective compound selection can enable distinct options in therapeutic-induced collateral growth. Here, B1 or B2 receptors show distinct affinity for different bradykinin compounds. Naturally, Bradykinin B2 receptors have high affinity for bradykinin and kallidin (lys-bradykinin). In contrast, the Bradykinin receptor 1 exhibits a high affinity for des-Arg9-bradykinin and des-Arg9-kallidin. These natural bradykinin receptor ligands are subjected to rapid inactivation by tissue and plasma enzymes, which limit their stability. However, many bradykinin compounds have been designed with improved properties for clinical intervention. For example, stimulation by orally active and selective bradykinin 2 receptor ligands for clinical intervention in different disease models was tested for the non-peptide compounds FR-190997 and FR-191413 (Fujisawa). Such studies might encourage the required efforts to identify more suited candidates.

Figure 6:
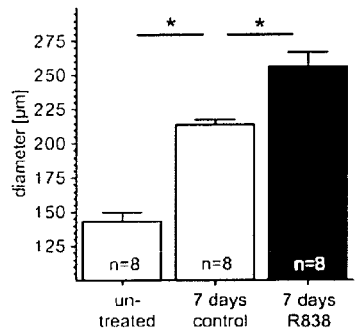
Figure 6:
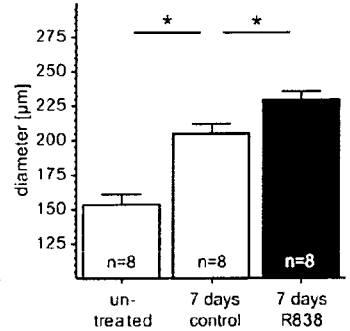
Figure 6:
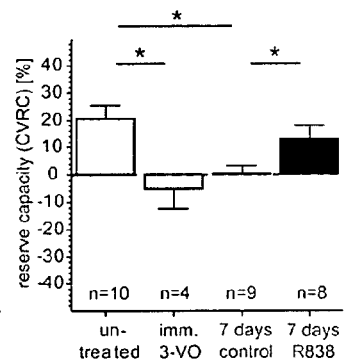
Figure 6:
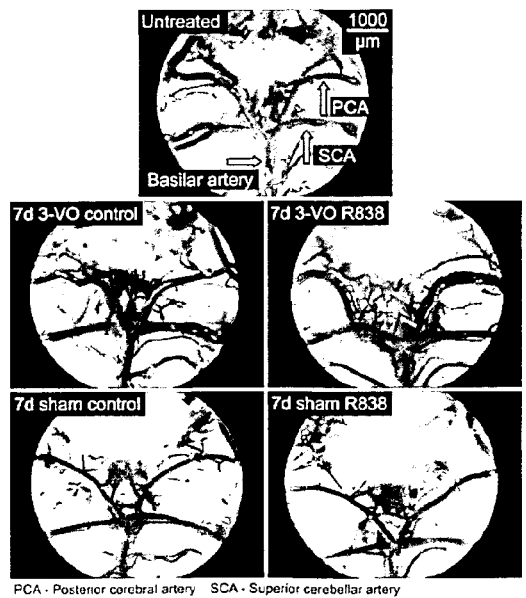

The best-characterized ligand for the Bradykinin receptor 1 signaling peptide, Sar[DPhe8]desArg9BK, exhibits a lower susceptibility toward proteolysis and a moderate affinity and potency (about 11- and 2-fold less, respectively) relative to the natural ligand Lys-desArg-bradykinin (Coté, 2009). FIG. 6 shows how cerebral arteriogenesis can be therapeutically enhanced by stimulation with Sar[DPhe8]desArg-bradykinin. Here it is demonstrated that B1R agonists bearing optimized pharmacological features (high potency, selectivity and stability toward proteolysis) hold promise as valuable therapeutic agents in the treatment of ischemic diseases.

Tables 1 and 2 provide a list of bradykinin receptor ligands for use in modulating (inhibit/activate) arteriogenesis. Table 3 provides a list of publications, which are incorporated by reference in their entireties, in which bradykinin receptor modulators are disclosed that can be used for modulating arteriogenesis via bradykinin receptor modulation.

TABLE 1

List of bradykinin receptor signaling agonists that can be used to modulate arteriogenesis.

| Agonist | B-Receptor | Substance |
|---|---|---|
| Bradykinin/H-1970 natural peptide | B2 | Peptide |
| Des-Arg9-Bradykinin natural peptide | B1 | Peptide |
| Kallidin/Lys-Bradykinin/H-2180 natural peptide | B2 | Peptide |
| (Des-Arg10)-Kallidin/Lys-(Des-Arg9)-Bradykinin natural peptide | B1 | Peptide |
| Sar-[D-Phe8]-des-Arg9-Bradykinin potent, selective, resistant to degradation | B1 | Modified Peptide |
| SarLys[Hyp3, Cha5, DPhe8]desArg9BK potent, selective, resistant to degradation | B1 | Modified Peptide |
| SarLys[Hyp3, Igl5, DPhe8]desArg9BK potent, selective, resistant to degradation | B1 | Modified Peptide |
| SarLys[Hyp3, Cpg5, DPhe8]desArg9BK potent, selective, resistant to degradation | B1 | Modified Peptide |
| RMP-7 lobradamil/Cereport potent, selective, resistant to degradation | B2 | Modified Peptide |
| JMV-1116 potent, selective, resistant to degradation | B2 | Modified Peptide |
| Ile-Ser-BK (B 1643) | B2 | Modified Peptide |

TABLE 1-continued

List of bradykinin receptor signaling agonists
that can be used to modulate arteriogenesis.

| Agonist | B-Receptor | Substance |
|---|---|---|
| [Phe8-(ψ-CH2NH)-Arg9]-BK | B2 | Modified Peptide |
| Hyp3,Tyr(Me)8]-BK | B2 | Modified Peptide |
| JMV1116 and analogues | B2 | Modified Peptide |
| [Hyp3]-BK (B 7775) | B2 | Modified Peptide |
| FR-190997 4-(2-pyridylmethoxy)-substituted quinoline | B2 | Non-Peptide |
| FR-191413 3-(2-pyridylmethyl)-substituted benzimidazole | B2 | Non-Peptide |

TABLE 2

List of bradykinin receptor signaling antagonists
that can be used to modulate arteriogenesis.

| Antagonist | B-Receptor | Substance |
|---|---|---|
| AC-Lys-Arg-Pro-Pro-Gly-Phe-Ser-DβNal-Iie R 715 | B1 | Modified Peptide |
| AC-Lys-Arg-Pro-Pro-Gly-(αMe)Phe-Ser-DβN al-Iie R892 | B1 | Modified Peptide |
| (Des-Arg9,Leu8)-Bradykinin | B1 | Peptide |
| [Leu8,des-Arg9]-BK | B1 | Modified Peptide |
| [Leu9,des-Arg10]-Kallidin (CP0298) | B1 | Modified Peptide |
| [des-Arg10]-HOE140 | B1 | Modified Peptide |
| Lys-[Leu8,desArg9]-BK | B1 | Modified Peptide |
| (B9858: H-Lys-Lys-Arg-Pro-Hyp-Gly-Igl-Ser-D-Igl-Oic-OH) | B1 | Modified Peptide |
| B-9430 (H-D-Arg-Arg-Pro-Hyp-Gly-Igl-Ser-D-Igl-Oic-Arg-OH) | B2 + B1 | Modified Peptide |
| Icatibant/Hoe140/H157 FIRAZYR | B2 | Modified Peptide |
| FR-167344 | B2 | Non-Peptide |
| FR-173657 | B2 | Non-Peptide |
| D-Arg[Hyp3,Thi5,HypE(trans-propyl)7,Oic8]-BK NPC17731 | B2 | Modified Peptide |
| WIN 64338 | B2 | Non-Peptide |
| Bradyzide | B2 | Non-Peptide |

TABLE 3

List of bradykinin receptor modulators that
can be used in the in the present invention.

| Inventor | Patent; year | B receptor Antagonist |
|---|---|---|
| Boehringer Ingelheim Int | WO2006048209; 2006 | B1R |
| Boehringer Ingelheim Int | WO2008022945; 2008 | B1R |
| Boehringer Ingelheim Int | WO2009013299; 2009 | B1R |
| Elan Pharmaceutical, Inc | WO2006071775; 2006 | B1R |
| Elan Pharmaceutical, Inc | WO2006113140; 2006 | B1R |
| Evotec Neurosciences GMBH | WO2008125570; 2008 | B1R |
| Richter Gedeon Nyrt | WO2007072092; 2007 | B1R |
| Richter Gedeon Nyrt | WO2008050167; 2008 | B1R |
| Richter Gedeon Nyrt | WO2008050168; 2008 | B1R |
| Richter Gedeon Nyrt | WO2008068540; 2008 | B1R |
| Grünenthal GMBH | WO2008040492; 2008 | B1R |
| Grünenthal GMBH | WO2008046573; 2008 | B1R |
| Grünenthal GMBH | WO2008131946; 2008 | B1R |
| Jerini AG | WO2007003411; 2007 | both |
| Jerini AG | WO2008116620; 2008 | B2R |
| Menarini | WO2006040004; 2006 | B2R |
| Menarini | WO2003103671; 2003 | B2R |
| Merck & Co | US20050261327; 2005 | B1R |
| Merck & Co | US20060122236; 2006 | B1R |
| Merck & Co | US20060173023; 2006 | B1R |
| Merck & Co | WO2005016886; 2005 | B1R |
| Merck & Co | US20060106011; 2006 | B1R |
| Merck & Co | US20060111392; 2006 | B1R |
| Merck & Co | US20060128765; 2006 | B1R |
| Merck & Co | WO2005004810; 2005 | B1R |
| Neurogen Corporation | WO200701007; 2007 | B1R |
| Neurogen Corporation | WO2007140383; 2007 | B1R |
| Neurogen Corporation | WO2008002849; 2008 | B1R |
| Neurogen Corporation | WO2008024692; 2008 | B1R |
| Neurogen Corporation | WO2008033739; 2008 | B1R |
| Sherbrooke University | WO2006017938; 2006 | B1R |
| Sherbrooke University | U.S. Pat. No. 7,211,566; 2007 | B1R |
| Park Choo | WO2007108566; 2007 | B1R |
| Park Choo | WO2007142431; 2007 | B1R |
| University of Colorado | WO2008124756; 2008 | B1R |

Bradykinin is rapidly hydrolyzed and degraded by ACE. Locally increased kinin concentrations, arising as a consequence of the blockade of ACE as the major kinin-degrading enzyme, significantly contribute to the apparent beneficial effects of ACE inhibitors, including their infarct size-reducing effects. In addition to direct Bradykinin receptor agonists and antagonists, Table 4 provides a comprehensive list of angiotensin converting enzyme (ACE) inhibitors.

TABLE 4

Sample list of ACE-Inhibitors for enhancing modulation
of arteriogenesis via bradykinin receptor signaling

| ACE-Inhibitors | Obtained from |
| --- | --- |
| Ramipril | Roche, AwD-Pharma, Schwarz-Pharma/Sanol, |
| Quinapril | R.A.N.-Pharm, ratiopharm, TAD Pharma, |
| Cilazapril | betapharm, Hennig, Abott, CT |
| Spirapril-HCl 1H2O | Arzneimittel, Wörwag, HEXAL, Winthrop, |
| Catopril | 1 A Pharma, AbZ-Pharma, ALIUD PHARMA, |
| Enalaprilmaleat | Sandoz, STADApharm, Schwarz Pharma |
| Lisinopril | |
| Bencapril-HCl | |
| Perindopril-Erbumin | |
| Trandolapril | |
| Fosinopril-Natrium | |

FIGURES

FIG. 1: Schematic of the flow induced collateral arterial system (arteriogenesis).

FIG. 2a: Relationship between blood flow and artery radius (The Law of Hagen-Poiseuille).

FIG. 2b: Differences between angiogenesis and arteriogenesis

FIG. 3: Schematic representation of the kallikrein-kinin system.

Figure 4A:
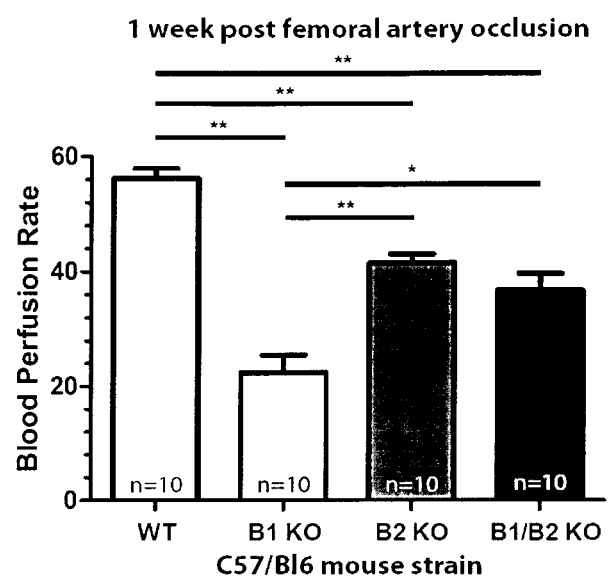

FIG. 4a: Measurement of collateral perfusion in the femoral ligature model in the mouse.

Figure 4B:
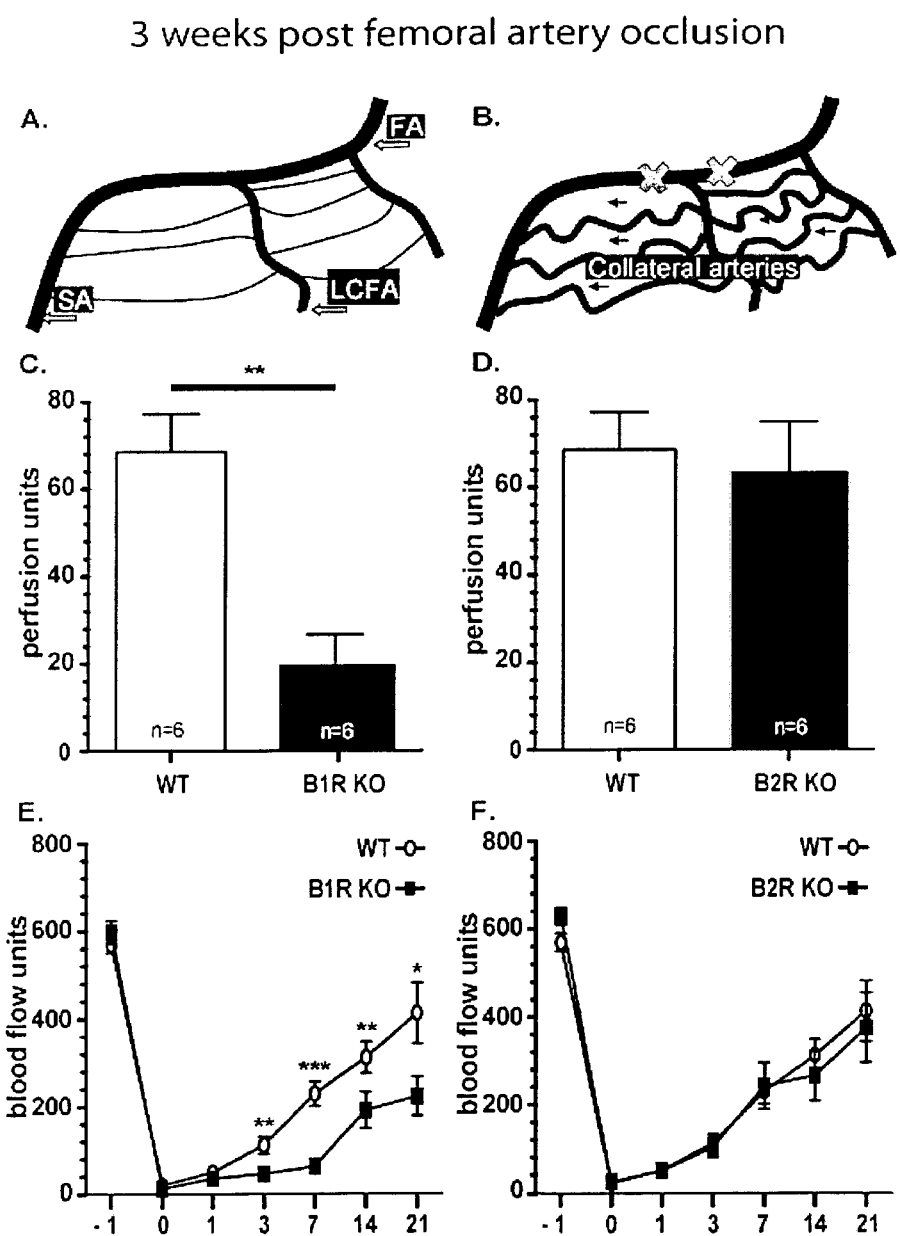

FIG. 4b: Hindlimb perfusion recovery—3 weeks post Femoral Artery Ligation.

Figure 5:
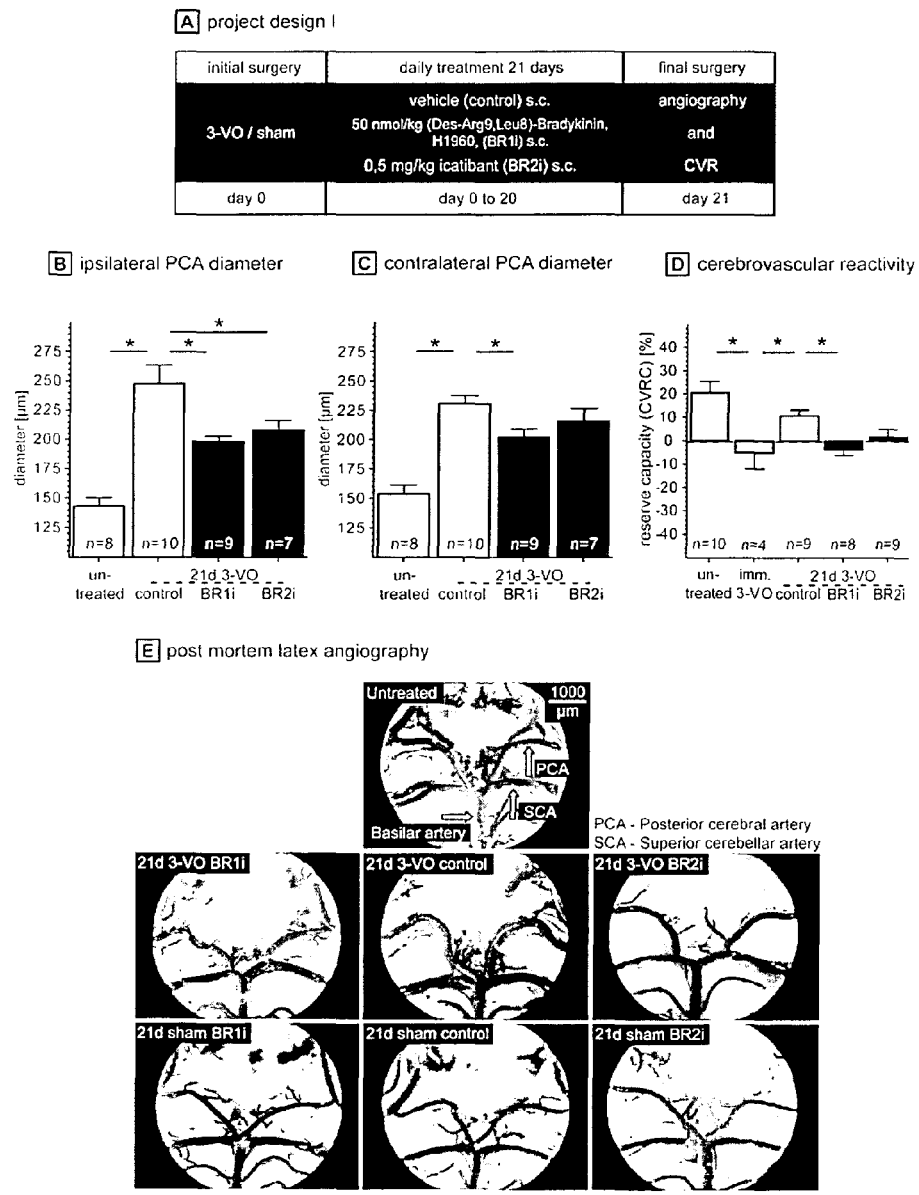

FIG. 5: Pharmacological inhibition of bradykinin receptor 1 and 2 signaling in the 3-vessel occlusion (3-VO) cerebral arteriogenesis model in rat.

FIG. 6: Therapeutic stimulation of arteriogenesis with a selective BR1 agonist in the 3-vessel occlusion (3-VO) cerebral arteriogenesis model in rat.

DETAILED DESCRIPTION OF THE FIGURES

FIG. 1: Schematic of the Flow Induced Collateral Arterial System (Arteriogenesis).

An artery occlusion of a major vessel leads to redistribution of blood flow by the recruitment of pre existing collateral vessels. Upon enhanced blood flow small arteries are remodeled into functional conductance arteries to supply hypoperfusion area with blood (Arteriogenesis—biological bypass).

FIG. 2a: Relationship Between Blood Flow and Artery Radius (the Law of Hagen-Poiseuille).

Equation clarifies the relationship between flow and vessel radius to the power of 4. Flow volume v, viscosity $\eta$, pressure differences $\Delta P$, distance differences (vessel length) $\Delta l$, radius r. A small increase in vessel radius leads to a significant enhancement of blood flow.

FIG. 2b: Differences Between Angiogenesis and Arteriogenesis

Angiogenesis refers to the growth of new small capillaries in the ischemic region downstream of the obstruction of a conductance vessel (driving force ischemia). Arteriogenesis refers to the redistribution of blood flow via the collateral artery network outside the ischemic region in oxygen-rich tissue that bypass the site of occlusion (driving force blood shear stress on vessel). Stimulation of arteriogenesis increases vessel diameter of the bypassing arteries, which produces a new functional conductance vessel to supply the endangered territory with blood.

FIG. 3: Schematic Representation of the Kallikrein-Kinin System.

Kininogen is processed by kallikrein to cleave bradykinin, kallidin and other kinins. Kinins signal via the constitutively expressed B2 receptor and the inducible B1 receptor. Stimulation of bradykinin receptors may activate intracellular signaling pathways in endothelial cells, smooth muscle cells and leucocytes, such as monocytes. This results in cell proliferation, cell migration and leucocyte recruitment, which are features of arteriogenesis. Collateral growth can be modulated by stimulation/inhibition of the bradykinin receptor signaling.

FIG. 4a: Measurement of Collateral Perfusion in the Femoral Ligature Model in the Mouse (7 Days Post Femoral Artery Ligation)

Arteriogenesis was measured in bradykinin receptor 1 knock out (KO) mice, bradykinin receptor 2 KO mice, bradykinin receptor 1 and 2 double KO mice and in wild type (WT) mice. All bradykinin receptor knock out mice exhibit a markedly reduced arteriogenesis. The B1 KO mice have the strongest phenotype and arteriogenesis is severely reduced in comparison with WT mice (more than 50% reduction in blood perfusion rate).

FIG. 4b: Hindlimb Perfusion Recovery—3 Weeks Post Femoral Artery Ligation (A) Schematic representation of the mice hindlimb collateral network. (FA: femoral artery, LCFA: lateral caudal femoral artery, SA: saphenous artery). (B) Occlusion of the femoral artery results in a positive outward remodeling of collateral arteries and recovery of blood flow within 7 days to 21 days. 3 weeks post FAO Hindlimb perfusion (measured by microspheres—in arbitrary units) is still significantly reduced in B1R KO (C) and blood flow does not recover. In contrast 3 weeks post FAO B2R KO mice (D) blood flow recovers and is comparable to WT mice 3 weeks post FAO. *, p<0.05; **, p<0.01.

FIG. 5: Pharmacological Inhibition of Bradykinin Receptor 1 and 2 Signaling in the 3-Vessel Occlusion (3-VO) Cerebral Arteriogenesis Model in Rat.

A. project design I. H-1960 is used as bradykinin receptor 1 (BR1) antagonist, Icatibant is used as BR2 antagonist. B,C. Diameters of the collateral pathway (posterior cerebral artery) ipsilateral (B) and contralateral (B) of the carotid artery ligation. D. Cerebrovascular reactivity. Collateral diameters (B,C) and cerebrovascular reactivities (D) are given for untreated animals (without 3-VO surgery), for control animals (3 weeks post 3-VO surgery without plus vehicle), for BR1 inhibition (3 weeks post 3-VO plus bradykinin receptor 1 antagonist treatment) and for BR2 inhibition (3 weeks post 3-VO bradykinin receptor 2 antagonist treatment). E. Brain vessel angiographies of untreated animals, post 3-VO and sham controls.

FIG. 6: Therapeutic Stimulation of Arteriogenesis with a Selective BR1 Agonist in the 3-Vessel Occlusion (3-VO) Cerebral Arteriogenesis Model in Rat.

A. project design II. R838 is used as bradykinin receptor 1 (BR1) agonist. B,C. Diameters of the collateral pathway (posterior cerebral artery) ipsilateral (B) and contralateral (B) of the carotid artery ligation. B,C. Diameters of the collateral pathway (posterior cerebral artery) ipsilateral (B) and contralateral (B) of the carotid artery ligation. D. Cerebrovascular reactivity. Collateral diameters (B,C) and cerebrovascular reactivities (D) are given for untreated animals (without 3-VO surgery), for control animals (1 weeks post 3-VO surgery plus vehicle), and for BR1 stimulation (1 weeks post 3-VO plus R838 treatment) E. Brain vessel angiographies of untreated animals, post 3-VO and sham controls.

EXAMPLES

Example 1

Measurement of Collateral Perfusion in the Femoral Ligature Model in the Mouse

Arteriogenesis was examined in an arteriogenesis model (ligation of the femoral artery) on the hind leg of C57/Bl6 mice. The ligature of the femoral artery in hind leg of a mouse is an established model for examining arteriogenesis (Hoefer, van Royen et al. 2001). Here arteriogenesis is measured through the collateral perfusion rate of the hind leg arteries by pressure controlled perfusion with fluorescent microspheres (Molecular Probes) of various sizes (Bergmann, Hoefer et al. 2006). In brief, a number of fluorescent microspheres where normalized against a reference number of blue microspheres. Values are expressed as percent perfusion by comparing the ligated vs. the unligated leg. Calculating collateral perfusion rate is a functional measurement to evaluate collateral growth (arteriogenesis). Finally arteriogenesis can be estimated by a count of microspheres using flow cytometry (MACS Quant, Miltenyi). Of all the functional measurements, the measurement of collateral growth by microsphere perfusion is considered to be the gold standard in evaluating arteriogenesis (Schaper 2009).

Collateral blood vessel growth is inhibited in BR1, BR2 and BR1/BR2 double-receptor knock out (KO) mice in comparison to wild type mice (WT) (FIGS. 4a and 4b). Arteriogenesis is significantly inhibited in BR2-receptor knock out and particular, bradykinin receptor BR1 KO mice (22.41 units) exhibit a more than 50% reduced collateral perfusion rate as compared to WT mice (56.17 units). In conclusion it was shown that the bradykinin receptor signaling pathway has a significant relevance for the modulation of arteriogenesis (molecular biological demonstration).

Example 2

Pharmacological Inhibition of Bradykinin Receptor 1 and 2 Signaling in the 3-Vessel Occlusion (3-VO) Cerebral Arteriogenesis Model in Rat Pharmacological modulation of arteriogenesis was analyzed using a 3 vessel occlusion (3-VO) model for cerebral arteriogenesis in the rat (Occlusion of both vertebral arteries and one carotid artery). Upon occlusion of three of four blood-supplying arteries to the brain, blood flow is redistributed by the recruitment of collateral pathways such as the posterior cerebral artery to supply the hypoperfusion area with blood. The 3-VO model in the rat has been established since 2003 and is acknowledged as a hypoperfusion model for testing cerebral arteriogenesis (Busch, Buschmann et al. 2003). By using the 3-VO model, relevant therapeutic stimulation of arteriogenesis was shown for instance by the application of GM-CSF (Buschmann, Circulation 2003).

Either by inhibition or stimulation of the bradykinin receptor signaling pathways, arteriogenesis was determined and physiological parameters of the brain were tested. Here, pharmacological modulation of collateral growth in the 3-VO model demonstrate that arteriogenesis can be inhibited through the selective B1 antagonists (Des-Arg$^9$, Leu$^8$)-bradykinin (H1960) and the selective B2-receptor antagonist HOE-140 (Icatibant) (FIG. 5). It is additionally demonstrated that cerebral arteriogenesis can be stimulated the selective BR1 agonist Sar-[D-Phe]des-Arg$^9$-bradykinin (R838) (FIG. 6).

The characterization of arteriogenesis was carried out via measurement of the artery or blood vessel diameter (posterior cerebral artery—PCA) in addition to via a measurement of the cerebrovascular reactivity (perfusion reserves in the brain). Cerebrovascular anatomy was studied after maximal vasodilation by a modification of the postmortem latex perfusion method of Maeda et al (Maeda, Hata et al. 1998). Through a measurement of the cerebrovascular reactivity the CO2 partial pressure in the blood was artificially increased (by means of a carboanhydrase-inhibitor acetazolamide) and the reaction of the artery was measured via a measurement of blood flow via laser-doppler cytometry.

FIGS. 5B and 5C demonstrate that collateral arterial growth is strongly reduced in response to the selective inhibition of the bradykinin receptor 1 signaling pathway and slightly in response to the selective inhibition of the bradykinin receptor 2 signaling. In the case of previous treatment with a bradykinin receptor B1 antagonist, it is demonstrated that the arteries increase in diameter to a lesser extent than in the untreated controls. Here collateral growth is reduced in both collateral pathways (ipsilateral and contralateral of the occluded carotide artery). Experiments which examine the diameter changes after application of a bradykinin receptor B2 antagonist demonstrate reduced collateral growth.

CVR is reduced through selective inhibition of the bradykinin B1 and B2 signaling pathways. Negative CVR values are based on the Steal phenomenon (Kuwabara, Ichiya et al. 1995). (FIG. 5D). Upon increase of the CO2 partial pressure under normal conditions, vessels in the brain are capable of increasing blood flow to around 20% of the normal blood flow. Directly after the 3-VO experiment no cerebrovascular reactivity is detectable anymore. Blood flow recovers within 3 weeks post 3-VO and the perfusion reserve is restored to around 10%. In contrast, three weeks after 3-VO, no increase in blood flow is detected in animals treated with bradykinin receptor inhibitors (BR1i, BR2i); thereby demonstrating that arteriogenesis has been effectively inhibited.

Example 3

Therapeutic Stimulation of Arteriogenesis with a Selective BR1 Agonist in the 3-Vessel Occlusion (3-VO) Cerebral Arteriogenesis Model in Rat FIG. 6 demonstrates therapeutic stimulation of arteriogenesis by using a selective bradykinin receptor 1 agonist Sar-[D-Phe]des-Arg$^9$-bradykinin (R838). In the case of simultaneous application of the bradykinin receptor 1 agonist R838, it is demonstrated that seven days after 3-VO the diameter of the posterior cerebral artery (PCA) is significantly greater than the diameter in untreated rats after 3-VO (FIG. 6B,C). Furthermore FIG. 6D. shows that CVR is significantly increased through stimulation with a selective bradykinin receptor 1 agonist R838 (Sar-[D-Phe]des-Arg$^9$-bradykinin). Arteriogenesis can by stimulated therapeutically by application of R838 for 1 week.

In summary the examples demonstrate that cerebral arteriogenesis is significantly inhibited by antagonists via blocking the bradykinin receptors (FIG. 5). Stimulation with a selective B1R agonist demonstrates that the cerebral arteriogenesis can also be stimulated (FIG. 6). Rats have been used in the present examples as a model for mammals. The present invention including products and methods described herein therefore also encompass the application of said products and methods in the treatment of all mammals, especially humans.

The invention claimed is:

1. A method for modulating collateral blood vessel growth of collateral arteries and/or non-collateral blood vessels of pre-existing arterial networks comprising
administering, to a patient at risk of cardiovascular ischemic disease a bradykinin receptor 1 (B1R) agonist in an amount effective to modulate collateral blood vessel growth of (a) collateral arteries and/or (b) non-collateral blood vessels of pre-existing arterial networks, wherein said patient:

(a) shows symptoms of being at risk of developing said cardiovascular ischemic disease, wherein said symptoms are:
a blood pressure and/or a cholesterol level that affords an at least 10% higher risk of developing said cardiovascular ischemic disease than an average risk of developing said cardiovascular ischemic disease throughout a population,
smoking,
atherosclerosis, thrombosis,
embolism, and/or
restenosis;
(b) shows a risk marker for cardiovascular ischemic disease in ex vivo tests; and/or
(c) has a genetic predisposition of developing a cardiovascular ischemic disease.

2. The method of claim 1, wherein said cardiovascular ischemic disease is
myocardial ischemia.

3. The method of claim 1, wherein said patient previously had been exposed to or is going to be exposed to
(a) a pharmaceutical or medical treatment damaging one or more arteries;
(b) a radiation treatment damaging one or more arteries; and/or
(c) a surgical treatment damaging one or more arteries.

4. The method of claim 1, wherein said patient is tested for arteriogenesis.

5. The method of claim 1, wherein said B1R agonist is administered in a long-term application.

6. The method of claim 5, wherein said long-term application is administrating said B1R agonist to the patient for at least one week, at least two weeks, at least three weeks, at least four weeks, at least one month, at least two months, at least three months, at least four months, at least five months, at least six months, at least seven months, at least eight months, at least nine months, at least ten months, at least eleven months, at least one year, at least two years, at least three years or enduringly.

7. The method of claim 1, wherein said B1R agonist is selected from the group consisting of
Sar-[D-Phe8]-des-Arg9-bradykinin (R838);
Lys-(Des-Arg9)-bradykinin;
T-kinin;
kallidin;
des-Arg9-bradykinin;
des-Arg10-kallidin;
Bradykinin;
bradykinin/H1970;
kallidin/Lys-bradykinin/H2180;
SarLys[Hyp3,Cha5,D-Phe8]desArg9-bradykinin;
SarLys[Hyp3,Igl5,D-Phe8]desArg9-bradykinin;
SarLys[Hyp3,Cpg5,D-Phe8]desArg9-bradykinin;
Ile-Ser-bradykinin (B1643);
[Phe8-ψ-CH2NH)-Arg9]-bradykinin;
[Hyp3,Tyr(Me)8]-bradykinin;
[Hyp3]-bradykinin (B7775); and
a combination of two or more thereof
and is administered optionally together with an agent increasing a concentration or a half-life of a bradykinin receptor agonist.

8. The method of claim 7, wherein said bradykinin receptor agonist is selected from the group consisting of R838, T-kinin, kallidin, des-Arg9-bradykinin and des-Arg10-kallidin, and is administered together with an agent increasing a concentration or a half-life of the bradykinin receptor agonist.

9. The method of claim 7, wherein said agent increasing the concentration or the half-life of a bradykinin receptor agonist is an enzyme inhibitor.

10. The method of claim 9, wherein said enzyme inhibitor is an angiotensin-converting enzyme (ACE) inhibitor, an amino peptidase P (APP) inhibitor and/or a carboxypeptidase N (CPN) inhibitor.

11. The method of claim 10, wherein said ACE inhibitor is selected from the group consisting of ramipril, quinapril, ciiazapril, spirapril-HCl 1H20, catopril, enalaprilmaleat, lisinopril, perindopril-erbumin, trandolapril, fosinopril-sodium and a combination of two or more thereof.

12. The method of claim 1, wherein said B1R agonist further induces migration of leukocyte cells and/or leucocyte precursor cells.

13. The method of claim 1, further comprising administering
(a) one or more colony stimulating factor(s) (CSF(s)); or
(b) one or more eicosanoid(s).

14. The method of claim 13, wherein the one or more eicosanoid(s) is one or more prostaglandin(s).

15. The method of claim 2, wherein
the myocardial ischemia is a coronary heart disease and/or myocardial infarction.

16. The method of claim 8, wherein the bradykinin receptor agonist is R838, T-kinin and/or kallidin.

* * * * *